(12) United States Patent
Capra et al.

(10) Patent No.: US 9,516,923 B2
(45) Date of Patent: Dec. 13, 2016

(54) COUPLING MEMBERS FOR CLOSURE DEVICES AND SYSTEMS

(71) Applicant: Boa Technology Inc., Denver, CO (US)

(72) Inventors: James Capra, Steamboat Springs, CO (US); Michael Nickel, Golden, CO (US); Robert Burns, Denver, CO (US); Tamara White, Denver, CO (US); Gary Hammerslag, Mondsee (AT)

(73) Assignee: Boa Technology Inc., Denver, CO (US)

( * ) Notice: Subject to any disclaimer, the term of this patent is extended or adjusted under 35 U.S.C. 154(b) by 169 days.

(21) Appl. No.: 14/071,435

(22) Filed: Nov. 4, 2013

(65) Prior Publication Data

US 2014/0123440 A1 May 8, 2014

Related U.S. Application Data

(60) Provisional application No. 61/722,022, filed on Nov. 2, 2012.

(51) Int. Cl.
*A61F 5/00* (2006.01)
*A44B 11/25* (2006.01)
(Continued)

(52) U.S. Cl.
CPC ............... *A44B 11/25* (2013.01); *A43B 3/122* (2013.01); *A43B 5/0401* (2013.01);
(Continued)

(58) Field of Classification Search
CPC ...... A47B 21/0073; B60P 3/34; A61F 5/0123; A61F 5/0118; A61F 5/3738; A61F 2250/001; A61F 5/0102; A61F 5/0111; A61F 5/022; A61F 5/3723; A61F 2005/0137; A61F 2005/0165; A61F 2005/0167; A61F 2005/0179; A61F 5/0125; A61F 5/013; A61F 2005/0139; A61F 2005/0174; A61F 2005/0181; A61F 5/0113; A61F 5/0193; A61F 5/028; A61F 5/01
(Continued)

(56) References Cited

U.S. PATENT DOCUMENTS 59,332 A 10/1866 White et al.
80,834 A 8/1868 Prussia
(Continued)

FOREIGN PATENT DOCUMENTS

CA 2112789 8/1994
CA 2114387 8/1994
(Continued)

OTHER PUBLICATIONS

"Strength of materials used to make my Safety Harnesses." Elaine, Inc. Jul. 9, 2012. Retrieved from <https://web.archive.org/web/20120709002720/http://www.childharness.ca/strength_data.html> on Mar. 17, 2014; 2 pages.
(Continued)

*Primary Examiner* — Michael Brown
(74) *Attorney, Agent, or Firm* — Kilpatrick Townsend & Stockton LLP

(57) ABSTRACT

According to one embodiment, a coupling component includes a female component and a male component. The female component includes a main body portion and a coupling aperture. Similarly, the male component includes a main body portion and a coupling member. The coupling member that is mateable with the coupling aperture of the female component to couple the male and female components together. The main body portion of the male component includes a top surface and a relatively planar bottom surface. The coupling member includes a relatively planar top surface and a bottom surface. The relatively planar top
(Continued)

surface of the coupling member is offset from the relatively planar bottom surface of the male component. The male and female components are non-releasable from a coupled engagement while under tension via a tension member.

16 Claims, 42 Drawing Sheets

(51) Int. Cl.
*B21D 53/46* (2006.01)
*A43C 11/16* (2006.01)
*A61F 5/01* (2006.01)
*A43B 3/12* (2006.01)
*A43B 5/04* (2006.01)

(52) U.S. Cl.
CPC ........ *A43C 11/165* (2013.01); *A44B 11/2588* (2013.01); *A61F 5/01* (2013.01); *B21D 53/46* (2013.01); *Y10T 24/40* (2015.01); *Y10T 29/12* (2015.01)

(58) Field of Classification Search
USPC ............................ 602/6, 16, 20–28; 128/882
See application file for complete search history.

(56) References Cited

U.S. PATENT DOCUMENTS

| 117,530 | A | 8/1871 | Foote |
|---|---|---|---|
| 228,946 | A | 6/1880 | Schulz |
| 230,759 | A | 8/1880 | Drummond |
| 379,113 | A | 3/1888 | Hibberd |
| 746,563 | A | 12/1903 | McMahon |
| 819,993 | A | 5/1906 | Haws et al. |
| 908,704 | A | 1/1909 | Sprinkle |
| 1,060,422 | A | 4/1913 | Bowdish |
| 1,062,511 | A | 5/1913 | Short |
| 1,083,775 | A | 1/1914 | Thomas |
| 1,090,438 | A | 3/1914 | Worth et al. |
| 1,170,472 | A | 2/1916 | Barber |
| 1,288,859 | A | 12/1918 | Feller et al. |
| 1,390,991 | A | 9/1921 | Fotchuk |
| 1,393,188 | A | 10/1921 | Whiteman |
| 1,469,661 | A | 2/1922 | Migita |
| 1,412,486 | A | 4/1922 | Paine |
| 1,416,203 | A | 5/1922 | Hobson |
| 1,429,657 | A | 9/1922 | Trawinski |
| 1,481,903 | A | 4/1923 | Hart |
| 1,466,673 | A | 9/1923 | Solomon et al. |
| 1,530,713 | A | 2/1924 | Clark |
| 1,502,919 | A | 7/1924 | Seib |
| 1,862,047 | A | 6/1932 | Boulet et al. |
| 1,995,243 | A | 6/1934 | Clarke |
| 2,088,851 | A | 8/1937 | Gantenbein |
| 2,109,751 | A | 3/1938 | Matthias et al. |
| 2,124,310 | A | 9/1938 | Murr, Jr. |
| 2,316,102 | A | 4/1943 | Preston |
| 2,539,026 | A | 1/1951 | Mangold |
| 2,611,940 | A | 9/1952 | Cairns |
| 2,673,381 | A | 3/1954 | Dueker |
| 2,907,086 | A | 10/1959 | Ord |
| 2,991,523 | A | 7/1961 | Del Conte |
| 3,028,602 | A | 4/1962 | Miller |
| 3,035,319 | A | 5/1962 | Wolff |
| 3,106,003 | A | 10/1963 | Herdman |
| 3,112,545 | A | 12/1963 | Williams |
| 3,122,810 | A | 3/1964 | Lawrence et al. |
| 3,163,900 | A | 1/1965 | Martin |
| D200,394 | S | 2/1965 | Hakim |
| 3,169,325 | A | 2/1965 | Fesl |
| 3,193,950 | A | 7/1965 | Liou |
| 3,197,155 | A | 7/1965 | Chow |
| 3,221,384 | A | 12/1965 | Aufenacker |
| 3,276,090 | A | 10/1966 | Nigon |
| D206,146 | S | 11/1966 | Hendershot |
| 3,345,707 | A | 10/1967 | Rita |
| D210,649 | S | 4/1968 | Getgay |
| 3,401,437 | A | 9/1968 | Christpohersen |
| 3,430,303 | A | 3/1969 | Perrin et al. |
| 3,491,465 | A | 1/1970 | Martin |
| 3,545,106 | A | 12/1970 | Martin |
| 3,618,232 | A | 11/1971 | Shnuriwsky |
| 3,668,791 | A | 6/1972 | Salzman et al. |
| 3,678,539 | A | 7/1972 | Graup |
| 3,703,775 | A | 11/1972 | Gatti |
| 3,729,779 | A | 5/1973 | Porth |
| 3,738,027 | A | 6/1973 | Schoch |
| 3,793,749 | A | 2/1974 | Gertsch et al. |
| 3,808,644 | A | 5/1974 | Schoch |
| 3,934,346 | A | 1/1976 | Sasaki et al. |
| 3,975,838 | A | 8/1976 | Martin |
| 4,084,267 | A * | 4/1978 | Zadina ............... A61F 2/54 602/22 |
| 4,130,949 | A | 12/1978 | Seidel |
| 4,142,307 | A | 3/1979 | Martin |
| 4,227,322 | A | 10/1980 | Annovi |
| 4,261,081 | A | 4/1981 | Lott |
| 4,267,622 | A | 5/1981 | Burnett-Johnston |
| 4,408,403 | A | 10/1983 | Martin |
| 4,417,703 | A | 11/1983 | Weinhold |
| 4,433,456 | A | 2/1984 | Baggio |
| 4,463,761 | A | 8/1984 | Pols et al. |
| 4,480,395 | A | 11/1984 | Schoch |
| 4,507,878 | A | 4/1985 | Semouha |
| 4,516,576 | A | 5/1985 | Kirchner |
| 4,551,932 | A | 11/1985 | Schoch |
| 4,555,830 | A | 12/1985 | Petrini et al. |
| 4,574,500 | A | 3/1986 | Aldinio et al. |
| 4,616,432 | A | 10/1986 | Bunch et al. |
| 4,616,524 | A | 10/1986 | Bidoia |
| 4,619,057 | A | 10/1986 | Sartor et al. |
| 4,620,378 | A | 11/1986 | Sartor |
| 4,631,839 | A | 12/1986 | Bonetti et al. |
| 4,631,840 | A | 12/1986 | Gamm |
| 4,633,599 | A | 1/1987 | Morell et al. |
| 4,644,938 | A | 2/1987 | Yates et al. |
| 4,654,985 | A | 4/1987 | Chalmers |
| 4,660,300 | A | 4/1987 | Morell et al. |
| 4,660,302 | A | 4/1987 | Arieh et al. |
| 4,680,878 | A | 7/1987 | Pozzobon et al. |
| 4,719,670 | A | 1/1988 | Kurt |
| 4,719,709 | A | 1/1988 | Vaccari |
| 4,719,710 | A | 1/1988 | Pozzobon |
| 4,722,477 | A | 2/1988 | Floyd |
| 4,741,115 | A | 5/1988 | Pozzobon |
| 4,748,726 | A | 6/1988 | Schoch |
| 4,760,653 | A | 8/1988 | Baggio |
| 4,780,969 | A | 11/1988 | White, Jr. |
| 4,787,124 | A | 11/1988 | Pozzobon et al. |
| 4,790,081 | A | 12/1988 | Benoit et al. |
| 4,796,829 | A | 1/1989 | Pozzobon et al. |
| 4,799,297 | A | 1/1989 | Baggio et al. |
| 4,802,291 | A | 2/1989 | Sartor |
| 4,811,503 | A | 3/1989 | Iwama |
| 4,826,098 | A | 5/1989 | Pozzobon et al. |
| 4,841,649 | A | 6/1989 | Baggio et al. |
| 4,856,207 | A | 8/1989 | Datson |
| 4,862,878 | A * | 9/1989 | Davison ............... A61F 5/0118 2/44 |
| 4,870,723 | A | 10/1989 | Pozzobon et al. |
| 4,870,761 | A | 10/1989 | Tracy |
| 4,884,760 | A | 12/1989 | Baggio et al. |
| 4,901,938 | A | 2/1990 | Cantley et al. |
| 4,924,605 | A | 5/1990 | Spademan |
| D308,282 | S | 6/1990 | Bergman et al. |
| 4,937,953 | A | 7/1990 | Walkhoff |
| 4,961,544 | A | 10/1990 | Bidoia |
| 4,979,953 | A | 12/1990 | Spence |
| 4,989,805 | A | 2/1991 | Burke |
| 5,001,817 | A | 3/1991 | De Bortoli et al. |
| 5,016,327 | A | 5/1991 | Klausner |
| 5,042,177 | A | 8/1991 | Schoch |
| 5,062,225 | A | 11/1991 | Gorza |

(56) References Cited

U.S. PATENT DOCUMENTS

| | | |
|---|---|---|
| 5,065,480 A | 11/1991 | DeBortoli |
| 5,065,481 A | 11/1991 | Walkhoff |
| 5,108,216 A | 4/1992 | Geyer et al. |
| 5,117,567 A | 6/1992 | Berger |
| 5,152,038 A | 10/1992 | Schoch |
| 5,157,813 A | 10/1992 | Carroll |
| 5,158,428 A | 10/1992 | Gessner et al. |
| 5,177,882 A | 1/1993 | Berger |
| 5,181,331 A | 1/1993 | Berger |
| 5,184,378 A | 2/1993 | Batra |
| D333,552 S | 3/1993 | Berger et al. |
| 5,205,055 A | 4/1993 | Harrell |
| 5,233,767 A | 8/1993 | Kramer |
| 5,249,377 A | 10/1993 | Walkhoff |
| 5,259,094 A | 11/1993 | Zepeda |
| 5,315,741 A | 5/1994 | Dubberke |
| 5,319,868 A | 6/1994 | Hallenbeck |
| 5,319,869 A | 6/1994 | McDonald et al. |
| 5,325,613 A | 7/1994 | Sussmann |
| 5,327,662 A | 7/1994 | Hallenbeck |
| 5,335,401 A | 8/1994 | Hanson |
| 5,341,583 A | 8/1994 | Hallenbeck |
| 5,345,697 A | 9/1994 | Quellais |
| 5,355,596 A | 10/1994 | Sussmann |
| 5,357,654 A | 10/1994 | Hsing-Chi |
| 5,371,957 A | 12/1994 | Gaudio |
| 5,381,609 A | 1/1995 | Hieblinger |
| 5,392,535 A | 2/1995 | Van Noy et al. |
| D357,576 S | 4/1995 | Steinweis |
| 5,425,161 A | 6/1995 | Schoch |
| 5,425,185 A | 6/1995 | Gansler |
| 5,430,960 A | 7/1995 | Richardson |
| 5,433,648 A | 7/1995 | Frydman |
| 5,463,822 A | 11/1995 | Miller |
| 5,477,593 A | 12/1995 | Leick |
| D367,755 S | 3/1996 | Jones |
| D367,954 S | 3/1996 | Dion |
| 5,502,902 A | 4/1996 | Sussmann |
| 5,511,325 A | 4/1996 | Hieblinger |
| 5,526,585 A | 6/1996 | Brown et al. |
| 5,535,531 A | 7/1996 | Karabed et al. |
| 5,537,763 A | 7/1996 | Donnadieu et al. |
| 5,557,864 A | 9/1996 | Marks |
| 5,566,474 A | 10/1996 | Leick et al. |
| D375,831 S | 11/1996 | Perry |
| 5,596,820 A | 1/1997 | Edauw et al. |
| 5,599,000 A | 2/1997 | Bennett |
| 5,599,288 A | 2/1997 | Shirley et al. |
| 5,600,874 A | 2/1997 | Jungkind |
| 5,606,778 A | 3/1997 | Jungkind |
| 5,607,448 A | 3/1997 | Stahl et al. |
| D379,113 S | 5/1997 | McDonald et al. |
| 5,638,588 A | 6/1997 | Jungkind |
| 5,640,785 A | 6/1997 | Egelja |
| 5,647,104 A | 7/1997 | James |
| 5,651,198 A | 7/1997 | Sussmann |
| 5,669,116 A | 9/1997 | Jungkind |
| 5,692,319 A | 12/1997 | Parker et al. |
| 5,718,021 A | 2/1998 | Tatum |
| 5,718,065 A | 2/1998 | Locker |
| 5,720,084 A | 2/1998 | Chen |
| 5,732,483 A | 3/1998 | Cagliari |
| 5,732,648 A | 3/1998 | Aragon |
| 5,736,696 A | 4/1998 | Del Rosso |
| 5,737,854 A | 4/1998 | Sussmann |
| 5,755,044 A | 5/1998 | Veylupek |
| 5,756,298 A | 5/1998 | Burczak |
| 5,761,777 A | 6/1998 | Leick |
| 5,772,146 A | 6/1998 | Kawamoto et al. |
| 5,784,809 A | 7/1998 | McDonald |
| 5,791,068 A | 8/1998 | Bernier et al. |
| 5,819,378 A | 10/1998 | Doyle |
| 5,833,640 A | 11/1998 | Vazquez, Jr. et al. |
| 5,839,210 A | 11/1998 | Bernier et al. |
| 5,845,371 A | 12/1998 | Chen |
| 5,909,946 A | 6/1999 | Okajima |
| D413,197 S | 8/1999 | Faye |
| 5,934,599 A | 8/1999 | Hammerslag |
| 5,937,542 A | 8/1999 | Bourdeau |
| 5,956,823 A | 9/1999 | Borel |
| 5,971,946 A | 10/1999 | Quinn et al. |
| 6,015,110 A | 1/2000 | Lai |
| 6,038,791 A | 3/2000 | Cornelius et al. |
| 6,052,921 A | 4/2000 | Oreck |
| 6,070,886 A | 6/2000 | Cornelius et al. |
| 6,070,887 A | 6/2000 | Cornelius et al. |
| 6,083,857 A | 7/2000 | Bottger |
| 6,088,936 A | 7/2000 | Bahl |
| 6,102,412 A | 8/2000 | Staffaroni |
| D430,724 S | 9/2000 | Matis et al. |
| 6,119,318 A | 9/2000 | Maurer |
| 6,119,372 A | 9/2000 | Okajima |
| 6,128,835 A | 10/2000 | Ritter et al. |
| 6,128,836 A | 10/2000 | Barret |
| 6,148,489 A | 11/2000 | Dickie et al. |
| 6,202,953 B1 | 3/2001 | Hammerslag |
| 6,219,891 B1 | 4/2001 | Maurer et al. |
| 6,240,657 B1 | 6/2001 | Weber et al. |
| 6,256,798 B1 | 7/2001 | Egolf et al. |
| 6,267,390 B1 | 7/2001 | Maravetz et al. |
| 6,286,233 B1 | 9/2001 | Gaither |
| 6,289,558 B1 | 9/2001 | Hammerslag |
| 6,311,633 B1 | 11/2001 | Keire |
| D456,130 S | 4/2002 | Towns |
| 6,370,743 B2 | 4/2002 | Choe |
| 6,401,364 B1 | 6/2002 | Burt |
| 6,416,074 B1 | 7/2002 | Maravetz et al. |
| 6,467,195 B2 | 10/2002 | Pierre et al. |
| 6,477,793 B1 | 11/2002 | Pruitt et al. |
| 6,502,286 B1 | 1/2003 | Dubberke |
| 6,543,159 B1 | 4/2003 | Carpenter et al. |
| 6,568,103 B2 | 5/2003 | Durocher |
| 6,606,804 B2 | 8/2003 | Kaneko et al. |
| 6,694,643 B1 | 2/2004 | Hsu |
| 6,708,376 B1 | 3/2004 | Landry |
| 6,711,787 B2 | 3/2004 | Jungkind et al. |
| 6,735,829 B2 | 5/2004 | Hsu |
| 6,757,991 B2 | 7/2004 | Sussmann |
| 6,775,928 B2 | 8/2004 | Grande et al. |
| 6,792,702 B2 | 9/2004 | Borsoi et al. |
| 6,802,439 B2 | 10/2004 | Azam et al. |
| 6,823,610 B1 | 11/2004 | Ashley |
| 6,871,812 B1 | 3/2005 | Chang |
| 6,877,256 B2 | 4/2005 | Martin et al. |
| 6,899,720 B1 | 5/2005 | McMillan |
| 6,922,917 B2 | 8/2005 | Kerns et al. |
| 6,938,913 B2 | 9/2005 | Elkington |
| 6,945,543 B2 | 9/2005 | De Bortoli et al. |
| D510,183 S | 10/2005 | Tresser |
| 6,976,972 B2 | 12/2005 | Bradshaw |
| 6,993,859 B2 | 2/2006 | Martin et al. |
| D521,226 S | 5/2006 | Douglas et al. |
| 7,073,279 B2 | 7/2006 | Min |
| 7,076,843 B2 | 7/2006 | Sakabayashi |
| 7,082,701 B2 | 8/2006 | Dalgaard et al. |
| 7,096,559 B2 | 8/2006 | Johnson et al. |
| 7,134,224 B2 | 11/2006 | Elkington et al. |
| 7,266,911 B2 | 9/2007 | Holzer et al. |
| 7,281,341 B2 | 10/2007 | Reagan et al. |
| 7,293,373 B2 | 11/2007 | Reagan et al. |
| 7,331,126 B2 | 2/2008 | Johnson |
| 7,343,701 B2 | 3/2008 | Pare et al. |
| 7,367,522 B2 | 5/2008 | Chen |
| 7,386,947 B2 | 6/2008 | Martin et al. |
| 7,392,602 B2 | 7/2008 | Reagan et al. |
| 7,401,423 B2 | 7/2008 | Reagan et al. |
| 7,490,458 B2 | 2/2009 | Ford |
| 7,568,298 B2 | 8/2009 | Kerns |
| 7,582,102 B2 | 9/2009 | Heinz et al. |
| 7,584,528 B2 | 9/2009 | Hu |
| 7,591,050 B2 | 9/2009 | Hammerslag |
| 7,597,675 B2 | 10/2009 | Ingimundarson et al. |
| 7,600,660 B2 | 10/2009 | Kasper et al. |
| 7,617,573 B2 | 11/2009 | Chen |

(56) References Cited

U.S. PATENT DOCUMENTS

| | | |
|---|---|---|
| 7,624,517 B2 | 12/2009 | Smith |
| 7,648,404 B1 | 1/2010 | Martin |
| 7,650,705 B2 | 1/2010 | Donnadieu et al. |
| 7,694,354 B2 | 4/2010 | Philpott et al. |
| 7,752,774 B2 | 7/2010 | Ussher |
| 7,757,412 B2 | 7/2010 | Farys |
| 7,774,956 B2 | 8/2010 | Dua et al. |
| D626,322 S | 11/2010 | Servettaz |
| 7,841,106 B2 | 11/2010 | Farys |
| 7,871,334 B2 | 1/2011 | Young et al. |
| 7,877,845 B2 | 2/2011 | Signori |
| 7,900,378 B1 | 3/2011 | Busse |
| 7,908,769 B2 | 3/2011 | Pellegrini |
| 7,947,061 B1 | 5/2011 | Reis |
| 7,950,112 B2 | 5/2011 | Hammerslag et al. |
| 7,954,204 B2 | 6/2011 | Hammerslag et al. |
| 7,963,049 B2 | 6/2011 | Messmer |
| 7,992,261 B2 | 8/2011 | Hammerslag et al. |
| D646,790 S | 10/2011 | Castillo et al. |
| 8,056,150 B2 | 11/2011 | Stokes et al. |
| 8,074,379 B2 | 12/2011 | Robinson, Jr. et al. |
| 8,091,182 B2 | 1/2012 | Hammerslag et al. |
| 8,109,015 B2 | 2/2012 | Signori |
| D663,850 S | 7/2012 | Joseph |
| D663,851 S | 7/2012 | Joseph |
| 8,215,033 B2 | 7/2012 | Carboy et al. |
| 8,231,074 B2 | 7/2012 | Hu et al. |
| D665,088 S | 8/2012 | Joseph |
| 8,235,321 B2 | 8/2012 | Chen |
| 8,245,371 B2 | 8/2012 | Chen |
| 8,257,293 B2 | 9/2012 | Ingimundarson et al. |
| 8,266,827 B2 | 9/2012 | Dojan et al. |
| 8,277,401 B2 | 10/2012 | Hammerslag et al. |
| 8,302,329 B2 | 11/2012 | Hurd et al. |
| 8,303,527 B2 | 11/2012 | Joseph |
| 8,308,098 B2 | 11/2012 | Chen |
| 8,353,087 B2 | 1/2013 | Chen |
| 8,353,088 B2 | 1/2013 | Ha |
| D677,045 S | 3/2013 | Voskuil |
| D679,019 S | 3/2013 | Siddle et al. |
| 8,434,200 B2 | 5/2013 | Chen |
| 8,490,299 B2 | 7/2013 | Dua et al. |
| 8,516,662 B2 | 8/2013 | Goodman et al. |
| 8,578,632 B2 | 11/2013 | Bell et al. |
| 8,652,164 B1 | 2/2014 | Aston |
| 8,713,820 B2 | 5/2014 | Kerns et al. |
| 8,984,719 B2 | 3/2015 | Soderberg et al. |
| 9,072,341 B2 | 7/2015 | Jungkind |
| D735,987 S | 8/2015 | Hsu |
| 9,101,181 B2 | 8/2015 | Soderberg et al. |
| 9,125,455 B2 | 9/2015 | Kerns et al. |
| 9,138,030 B2 | 9/2015 | Soderberg et al. |
| 2002/0050076 A1 | 5/2002 | Borsoi et al. |
| 2002/0062579 A1 | 5/2002 | Caeran |
| 2002/0095750 A1 | 7/2002 | Hammerslag |
| 2002/0129518 A1 | 9/2002 | Borsoi et al. |
| 2002/0148142 A1 | 10/2002 | Oorei et al. |
| 2002/0166260 A1 | 11/2002 | Borsoi |
| 2002/0178548 A1 | 12/2002 | Freed |
| 2003/0079376 A1 | 5/2003 | Oorei et al. |
| 2003/0144620 A1* | 7/2003 | Sieller .................. A61F 5/0125 602/5 |
| 2003/0150135 A1 | 8/2003 | Liu |
| 2003/0177662 A1 | 9/2003 | Elkington et al. |
| 2003/0204938 A1 | 11/2003 | Hammerslag |
| 2004/0041452 A1 | 3/2004 | Williams |
| 2004/0211039 A1 | 10/2004 | Livingston |
| 2005/0054962 A1 | 3/2005 | Bradshaw |
| 2005/0060912 A1 | 3/2005 | Holzer et al. |
| 2005/0081339 A1 | 4/2005 | Sakabayashi |
| 2005/0081403 A1 | 4/2005 | Mathieu |
| 2005/0087115 A1 | 4/2005 | Martin |
| 2005/0098673 A1 | 5/2005 | Huang |
| 2005/0102861 A1 | 5/2005 | Martin |
| 2005/0126043 A1 | 6/2005 | Reagan et al. |
| 2005/0172463 A1 | 8/2005 | Rolla |
| 2005/0184186 A1 | 8/2005 | Tsoi et al. |
| 2005/0198866 A1 | 9/2005 | Wiper et al. |
| 2006/0135901 A1 | 6/2006 | Ingimundarson et al. |
| 2006/0156517 A1 | 7/2006 | Hammerslag et al. |
| 2006/0179685 A1 | 8/2006 | Borel et al. |
| 2006/0185193 A1 | 8/2006 | Pellegrini |
| 2006/0287627 A1 | 12/2006 | Johnson |
| 2007/0006489 A1 | 1/2007 | Case, Jr. et al. |
| 2007/0063459 A1 | 3/2007 | Kavarsky |
| 2007/0068040 A1 | 3/2007 | Farys |
| 2007/0084956 A1 | 4/2007 | Chen |
| 2007/0113524 A1 | 5/2007 | Lander |
| 2007/0128959 A1 | 6/2007 | Cooke |
| 2007/0169378 A1 | 7/2007 | Sodeberg et al. |
| 2008/0016717 A1 | 1/2008 | Ruban |
| 2008/0060167 A1 | 3/2008 | Hammerslag et al. |
| 2008/0060168 A1 | 3/2008 | Hammerslag et al. |
| 2008/0066272 A1 | 3/2008 | Hammerslag et al. |
| 2008/0066345 A1 | 3/2008 | Hammerslag et al. |
| 2008/0066346 A1 | 3/2008 | Hammerslag et al. |
| 2008/0068204 A1 | 3/2008 | Carmen et al. |
| 2008/0083135 A1 | 4/2008 | Hammerslag et al. |
| 2008/0092279 A1 | 4/2008 | Chiang |
| 2008/0172848 A1 | 7/2008 | Chen |
| 2008/0196224 A1 | 8/2008 | Hu |
| 2009/0019734 A1 | 1/2009 | Reagan et al. |
| 2009/0071041 A1 | 3/2009 | Hooper |
| 2009/0090029 A1 | 4/2009 | Kishino |
| 2009/0172928 A1 | 7/2009 | Messmer et al. |
| 2009/0184189 A1 | 7/2009 | Soderberg et al. |
| 2009/0272007 A1 | 11/2009 | Beers et al. |
| 2009/0277043 A1 | 11/2009 | Graser et al. |
| 2010/0064547 A1 | 3/2010 | Kaplan et al. |
| 2010/0101061 A1 | 4/2010 | Ha |
| 2010/0139057 A1 | 6/2010 | Soderberg et al. |
| 2010/0154254 A1 | 6/2010 | Fletcher |
| 2010/0175163 A1 | 7/2010 | Litke |
| 2010/0251524 A1 | 10/2010 | Chen |
| 2010/0299959 A1 | 12/2010 | Hammerslag et al. |
| 2010/0319216 A1 | 12/2010 | Grenzke et al. |
| 2011/0000173 A1 | 1/2011 | Lander |
| 2011/0071647 A1 | 3/2011 | Mahon |
| 2011/0162236 A1 | 7/2011 | Voskuil et al. |
| 2011/0167543 A1 | 7/2011 | Kovacevich et al. |
| 2011/0191992 A1 | 8/2011 | Chen |
| 2011/0197362 A1 | 8/2011 | Chella et al. |
| 2011/0225843 A1 | 9/2011 | Kerns et al. |
| 2011/0258876 A1 | 10/2011 | Baker et al. |
| 2011/0266384 A1 | 11/2011 | Goodman et al. |
| 2012/0000091 A1 | 1/2012 | Cotterman et al. |
| 2012/0004587 A1 | 1/2012 | Nickel et al. |
| 2012/0005995 A1 | 1/2012 | Emery |
| 2012/0023717 A1 | 2/2012 | Chen |
| 2012/0047620 A1 | 3/2012 | Ellis et al. |
| 2012/0101417 A1 | 4/2012 | Joseph |
| 2012/0102783 A1 | 5/2012 | Swigart et al. |
| 2012/0138882 A1 | 6/2012 | Moore et al. |
| 2012/0157902 A1 | 6/2012 | Castillo et al. |
| 2012/0167290 A1 | 7/2012 | Kovacevich et al. |
| 2012/0174437 A1 | 7/2012 | Heard |
| 2012/0228419 A1 | 9/2012 | Chen |
| 2012/0246974 A1 | 10/2012 | Hammerslag et al. |
| 2012/0310273 A1 | 12/2012 | Thorpe |
| 2013/0012856 A1 | 1/2013 | Hammerslag et al. |
| 2013/0014359 A1 | 1/2013 | Chen |
| 2013/0019501 A1 | 1/2013 | Gerber |
| 2013/0025100 A1 | 1/2013 | Ha |
| 2013/0091667 A1 | 4/2013 | Zerfas et al. |
| 2013/0091674 A1 | 4/2013 | Chen |
| 2013/0092780 A1 | 4/2013 | Soderberg et al. |
| 2013/0269219 A1 | 10/2013 | Burns et al. |
| 2013/0277485 A1 | 10/2013 | Soderberg et al. |
| 2013/0340283 A1 | 12/2013 | Bell et al. |
| 2013/0345612 A1 | 12/2013 | Bannister et al. |
| 2014/0082963 A1 | 3/2014 | Beers |
| 2014/0094728 A1 | 4/2014 | Soderberg et al. |
| 2014/0117140 A1 | 5/2014 | Goodman et al. |
| 2014/0123440 A1 | 5/2014 | Capra et al. |

(56) References Cited

U.S. PATENT DOCUMENTS

| | | |
|---|---|---|
| 2014/0123449 A1 | 5/2014 | Soderberg et al. |
| 2014/0208550 A1 | 7/2014 | Neiley |
| 2014/0221889 A1 | 8/2014 | Burns et al. |
| 2014/0257156 A1 | 9/2014 | Capra et al. |
| 2014/0290016 A1 | 10/2014 | Lovett et al. |
| 2014/0359981 A1 | 12/2014 | Cotterman et al. |
| 2015/0007422 A1 | 1/2015 | Cavanagh et al. |
| 2015/0014463 A1 | 1/2015 | Converse et al. |
| 2015/0026936 A1 | 1/2015 | Kerns et al. |
| 2015/0033519 A1 | 2/2015 | Hammerslag et al. |
| 2015/0059206 A1 | 3/2015 | Lovett et al. |
| 2015/0076272 A1 | 3/2015 | Trudel et al. |
| 2015/0089779 A1 | 4/2015 | Lawrence et al. |
| 2015/0089835 A1 | 4/2015 | Hammerslag et al. |
| 2015/0101160 A1 | 4/2015 | Soderberg et al. |
| 2015/0150705 A1 | 6/2015 | Capra et al. |
| 2015/0151070 A1 | 6/2015 | Capra et al. |
| 2015/0190262 A1 | 7/2015 | Capra et al. |
| 2015/0223608 A1 | 8/2015 | Capra et al. |
| 2015/0237962 A1 | 8/2015 | Soderberg et al. |
| 2015/0335458 A1 | 11/2015 | Romo |

FOREIGN PATENT DOCUMENTS

| | | |
|---|---|---|
| CH | 199766 | 9/1938 |
| CH | 204 834 A | 5/1939 |
| CN | 2613167 | 4/2004 |
| CN | 201015448 | 2/2008 |
| DE | 641976 | 2/1937 |
| DE | 23 41 658 | 3/1974 |
| DE | 29 00 077 A1 | 7/1980 |
| DE | 31 01 952 A1 | 9/1982 |
| DE | 38 13 470 | 11/1989 |
| DE | 43 02 401 A1 | 8/1994 |
| DE | 43 05 671 A1 | 9/1994 |
| DE | 9308037 | 10/1994 |
| DE | 43 26 049 A1 | 2/1995 |
| DE | 9315776 | 2/1995 |
| DE | 29503552.8 | 4/1995 |
| DE | 196 24 553 | 1/1998 |
| DE | 19945045 A1 | 3/2001 |
| DE | 20 2010 000 354 U1 | 6/2010 |
| DE | 11 2013 005 273 T5 | 9/2015 |
| EP | 0 056 953 | 8/1982 |
| EP | 0 099 504 | 2/1984 |
| EP | 0 123 050 | 10/1984 |
| EP | 0 155 596 | 9/1985 |
| EP | 0 201 051 | 11/1986 |
| EP | 0 255 869 | 2/1988 |
| EP | 0 393 380 | 10/1990 |
| EP | 0 589 232 A1 | 3/1994 |
| EP | 0 589 233 A1 | 3/1994 |
| EP | 0 614 625 A1 | 9/1994 |
| EP | 0 651 954 A1 | 5/1995 |
| EP | 0 679 346 | 11/1995 |
| EP | 0 693 260 B1 | 1/1996 |
| EP | 0 734 662 A1 | 10/1996 |
| EP | 0 848 917 | 6/1998 |
| EP | 0 923 965 | 6/1999 |
| EP | 0 937 467 | 8/1999 |
| EP | 1163860 | 12/2001 |
| EP | 1 219 195 | 7/2002 |
| EP | 1 236 412 A | 9/2002 |
| EP | 2298107 B1 | 3/2011 |
| EP | 2359708 | 8/2011 |
| FR | 1 404 799 | 7/1965 |
| FR | 2 019 991 A | 7/1970 |
| FR | 2 598 292 A1 | 11/1987 |
| FR | 2 726 440 A1 | 5/1996 |
| FR | 2 770 379 A1 | 5/1999 |
| FR | 2 814 919 A1 | 4/2002 |
| GB | 189911673 | 7/1899 |
| GB | 216400 | 5/1924 |
| GB | 2 449 722 A | 12/2008 |
| IT | 1220811 | 6/1990 |
| IT | PD 2003 A 000197 | 4/2003 |
| IT | PD 2003 A 000198 | 3/2005 |
| JP | 51-121375 | 10/1976 |
| JP | 53-124987 | 3/1977 |
| JP | 54-108125 | 2/1978 |
| JP | H02-236025 | 9/1990 |
| JP | 6-284906 | 2/1996 |
| JP | 3030988 | 11/1996 |
| JP | 3031760 | 12/1996 |
| JP | 10-199366 | 7/1998 |
| JP | 2004-016732 | 1/2004 |
| JP | 2004-041666 | 2/2004 |
| JP | 2009-504210 | 2/2009 |
| KR | 20-0367882 | 11/2004 |
| KR | 20-0400568 | 8/2005 |
| KR | 10-0598627 | 7/2006 |
| KR | 10-0953398 | 4/2010 |
| KR | 10-1025134 B1 | 3/2011 |
| KR | 10-1028468 | 4/2011 |
| KR | 10-1053551 | 7/2011 |
| WO | WO 94/27456 | 12/1994 |
| WO | WO 95/11602 | 5/1995 |
| WO | WO 95/03720 | 9/1995 |
| WO | WO 98/33408 | 8/1998 |
| WO | WO 98/37782 | 9/1998 |
| WO | WO 99/09850 | 3/1999 |
| WO | WO 99/15043 | 4/1999 |
| WO | WO 99/43231 | 9/1999 |
| WO | WO 00/53045 | 9/2000 |
| WO | WO 00/76337 A1 | 12/2000 |
| WO | WO 01/08525 | 2/2001 |
| WO | WO 01/15559 | 3/2001 |
| WO | WO 02/051511 | 7/2002 |
| WO | WO 2004/093569 | 11/2004 |
| WO | WO 2005/013748 A1 | 2/2005 |
| WO | WO/2007/016983 | 2/2007 |
| WO | WO 2008/015214 | 2/2008 |
| WO | WO/2008/033963 | 3/2008 |
| WO | WO/2009/134858 | 11/2009 |
| WO | WO 2010/059989 A2 | 5/2010 |
| WO | WO 2012/165803 A2 | 12/2012 |
| WO | WO/2015/035885 | 3/2015 |
| WO | WO 2015/179332 A1 | 11/2015 |
| WO | WO 2015/181928 A1 | 12/2015 |

OTHER PUBLICATIONS

International Search Report and Written Opinion mailed Apr. 25, 2014 for PCT/US2014/014952 filed Feb. 5, 2014, 17 pages.
International Search Report and Written Opinion mailed Apr. 7, 2014 for PCT/US2013/068342 filed Nov. 4, 2013, 29 pages.
U.S. Appl. No. 09/956,601 Including its prosecution history, filed Sep. 18, 2001, Hammerslag.
Asolo® Boot Brochure Catalog upon information and belief date is as early as Aug. 22, 1997, 12 pages.
La Sportiva, A Technical Lightweight Double Boot for Cold Environments, 1 page. Accessed on May 27, 2015. Retrieved from http://www.sportiva.com/products/footwear/mountain/spantik.
"Strength of materials used to make my Safety Harnesses," Elaine, Inc. Jul. 9, 2012. Retrieved from <https://web.archive.org/web/20120709002720/http://www.childharness.ca/strength_data.html> on Mar. 17, 2014, 2 pages.
International Search Report and Written Opinion for PCT/US2013/032326 mailed Jun. 14, 2013, 27 pages.
International Preliminary Report on Patentability for PCT/US2013/032326 issued Sep. 16, 2014, 6 pages.
International Search Report and Written Opinion for PCT/US2013/057637 mailed Apr. 7, 2014, 34 pages.
International Preliminary Report on Patentability for PCT/US2013/057637 issued Mar. 3, 2015, 9 pages.
International Search Report and Written Opinion for PCT/US2013/068342 mailed Apr. 7, 2014, 29 pages.
International Preliminary Report on Patentability for PCT/US2013/068342 issued May 5, 2015, 9 pages.
International Search Report and Written Opinion for PCT/US2014/014952 mailed Apr. 25, 2014, 17 pages.

(56) References Cited

OTHER PUBLICATIONS

International Preliminary Report on Patentability for PCT/US2014/014952 issued Aug. 11, 2015, 9 pages.
International Search Report and Written Opinion for PCT/US2014/066212 mailed Apr. 22, 2015, 16 pages.
International Search Report and Written Opinion for PCT/US2014/032574 mailed Oct. 31, 2014, 19 pages.
International Search Report and Written Opinion for PCT/US2014/045291 mailed Nov. 6, 2014, 12 pages.
International Search Report and Written Opinion for PCT/US2014/013458 mailed May 19, 2014, 12 pages.
International Preliminary Report on Patentability for PCT/US2014/013458 issued Jul. 28, 2015, 7 pages.
International Search Report and Written Opinion for PCT/US2013/068814 mailed Jun. 9, 2014, 18 pages.
International Preliminary Report on Patentability for PCT/US2013/068814 issued May 12, 2015, 12 pages.
Notice of Reasons for Rejection from the Japanese Patent Office dated Feb. 26, 2015 for design application No. 2014-015570, 4 pages.
Receipt of Certificate of Design Registration No. 1529678 from the Japanese Patent Office for design application No. 2014-015570 dated Jun. 26, 2015, 1 page.
International Search Report and Written Opinion for PCT/US2014/055710 mailed Jul. 6, 2015, 19 pages.
International Search Report and Written Opinion for PCT/US2014/054420 mailed Jul. 6, 2015, 21 pages.
The Preliminary Rejections from the Korean Intellectual Property Office for Application No. 30-201434959 received Aug. 7, 2015, is not translated into English. The document requests a renaming of the application to be in accordance with Korean patent law, 5 pages total.
The Preliminary Rejections from the Korean Intellectual Property Office for Application No. 30-201434959 received Apr. 7, 2015, is not translated into English. The document requests a revision of the drawings to be in accordance with Korean patent law, 6 pages total.
Certificate of Design Registration No. 30-809409 on Aug. 3, 2015 from the Korean Intellectual Property Office for Appln No. 30-2015-11475, 2 pages.
Certificate of Design Registration No. 30-809410 on Aug. 3, 2015 from the Korean Intellectual Property Office for Appln No. 30-2015-11476, 2 pages.
European Search Report for EP 14168879 mailed Oct. 29, 2014, 9 pages.
International Search Report and Written Opinion for PCT/US2014/020894 mailed Jun. 20, 2014, 12 pages.
International Preliminary Report on Patentability for PCT/US2014/020894 issued Sep. 8, 2015, 7 pages.
International Search Report and Written Opinion for PCT/US2014/041144 mailed Dec. 10, 2014, 13 pages.
International Preliminary Report on Patentability for PCT/US2014/032574 issued Oct. 6, 2015, 12 pages.
International Search Report and Written Opinion for PCT/US2014/046238 mailed Nov. 21, 2014, 17 pages.
Office Action received Oct. 8, 2015 from the German Patent and Trademark Office for Appln No. 402015100191.2, regarding the title of the invention, 2 pages.
Anonymous, "Shore durometer," Wikipedia, the free encyclopedia, Mar. 10, 2012, XP002747470, Retrieved from the Internet: URL: https://en.wikipedia.org/w/index.php?title=Shore_durometer&oldid=481128180 [retrieved on Oct. 20, 2015] * shore A, shore D, durometer, polymer, rubber, gel; the whole document *, 6 pages.
Notice of Reasons for Rejection from the Japanese Patent Office dated Oct. 5, 2015 for design application No. 2015-004923, 4 pages.
"Save Tourniquet," 3 pages. Copyright 2015. Accessed on Dec. 11, 2015. Retrieved from http://www.savetourniquet.com/.
International Preliminary Report on Patentability for PCT/US2014/041144 issued Dec. 8, 2015, all pages.
Supplementary European Search Report for EP 13761841 dated Oct. 21, 2015, all pages.

\* cited by examiner

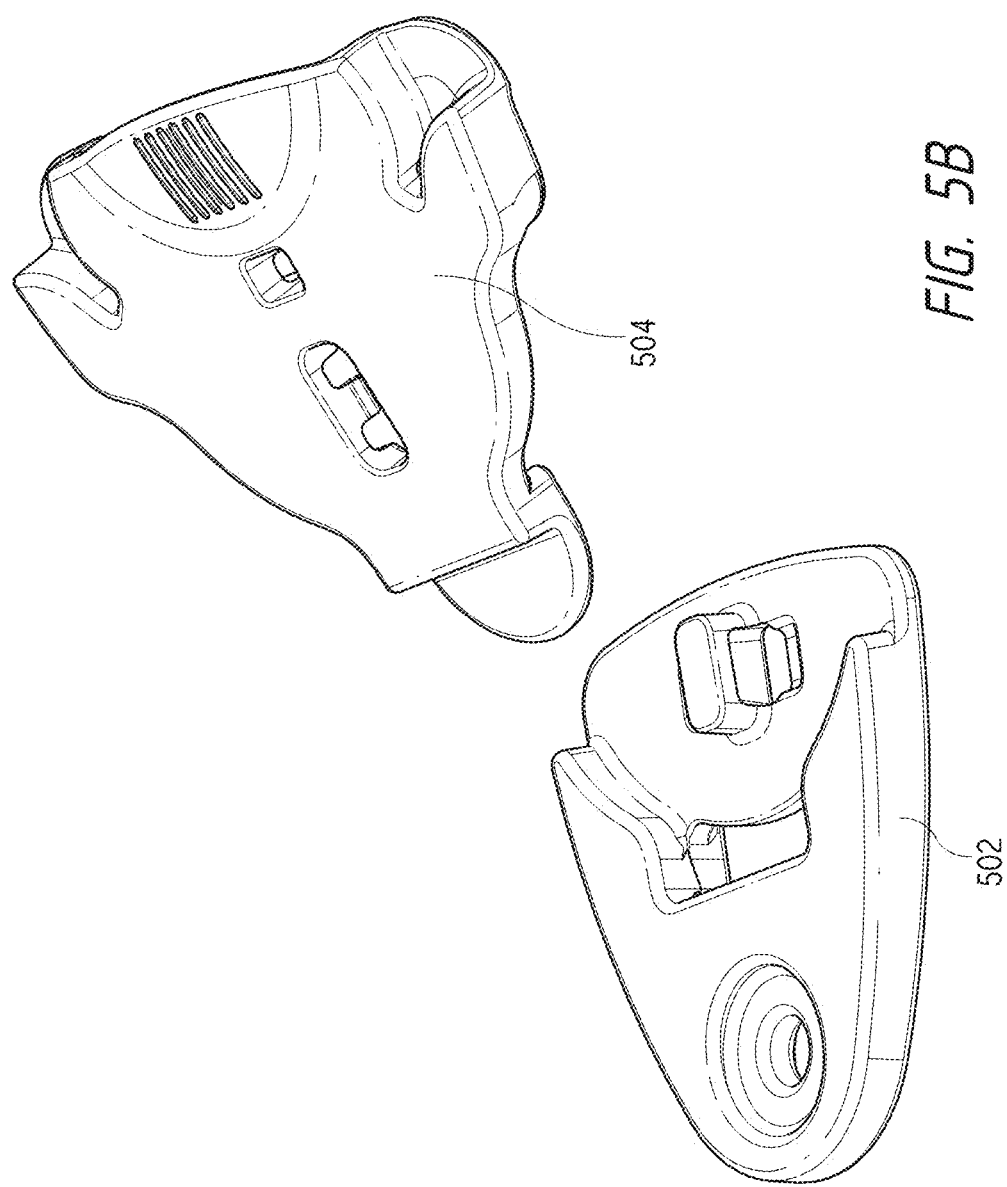

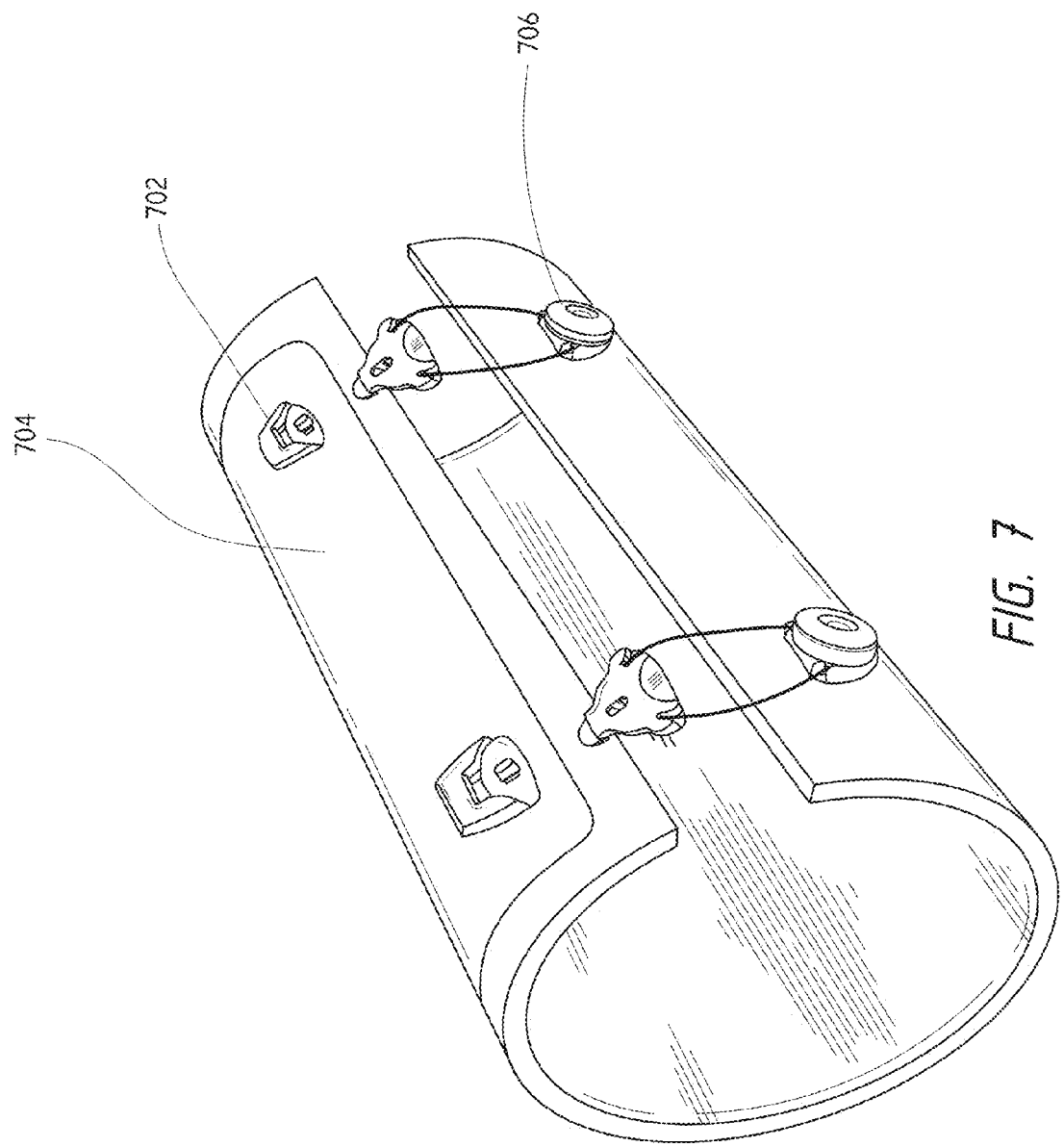

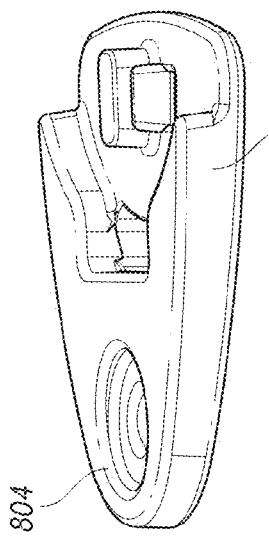
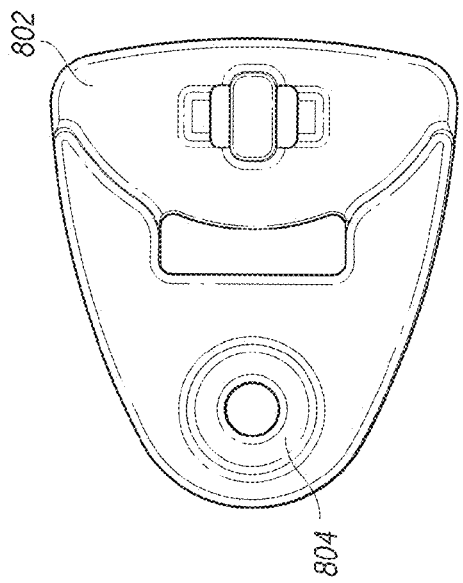
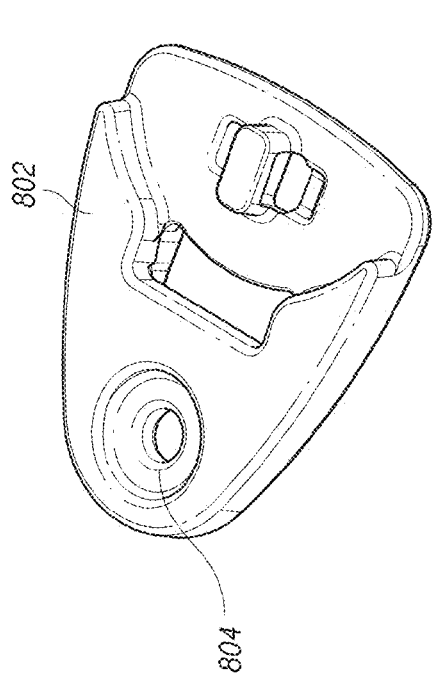
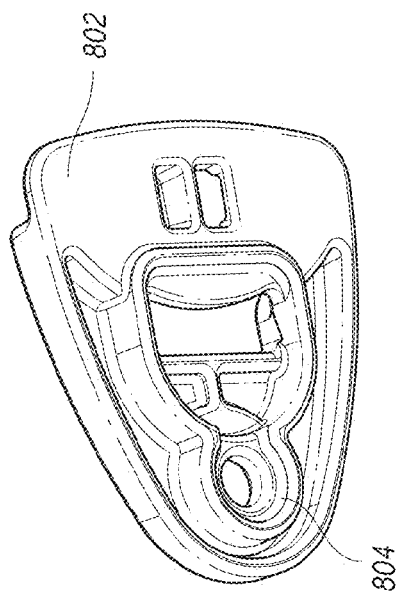

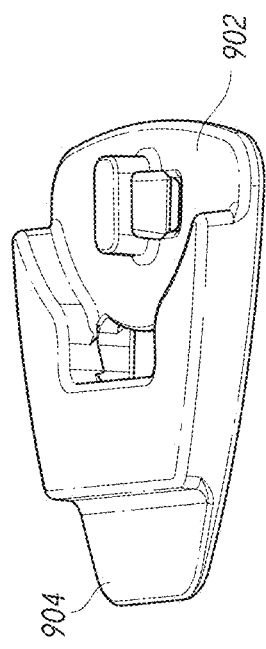
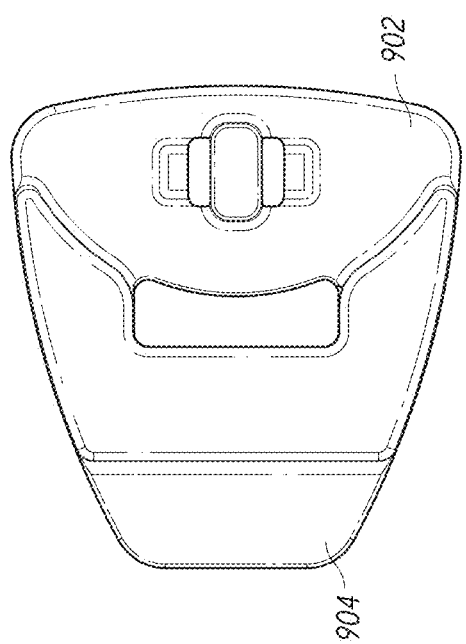
FIG. 9C
FIG. 9D
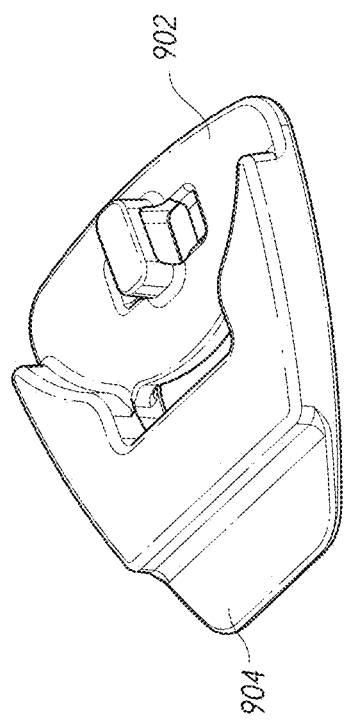
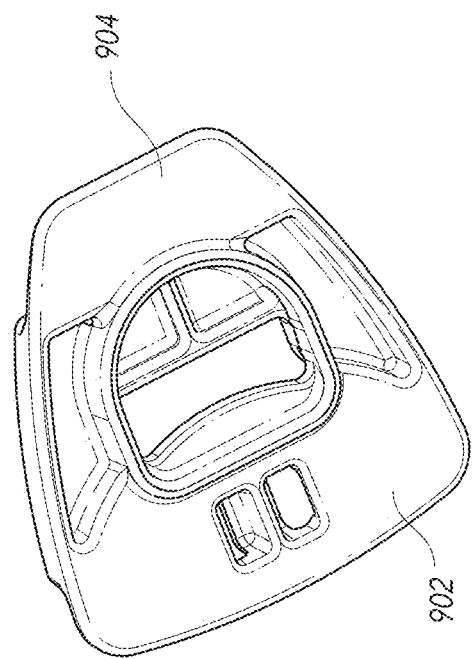
FIG. 9A
FIG. 9B

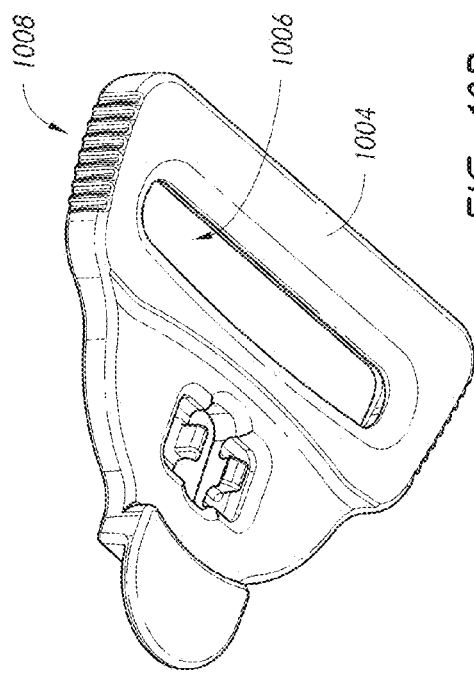
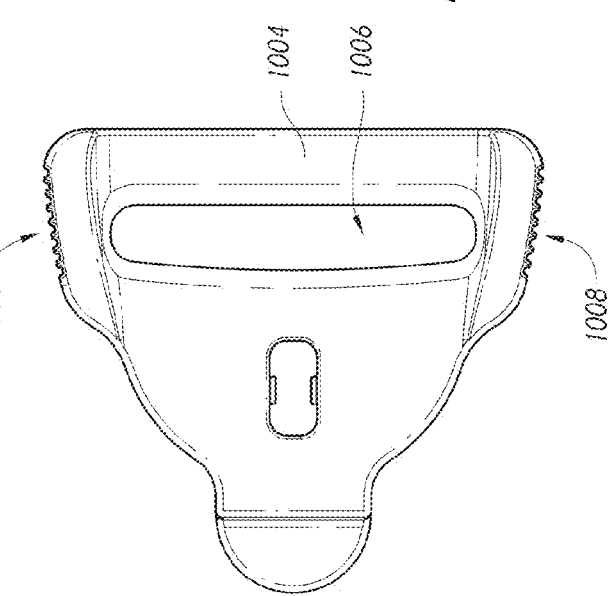
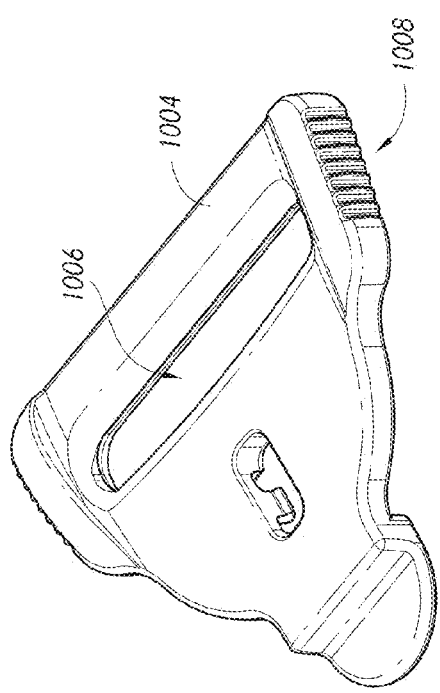
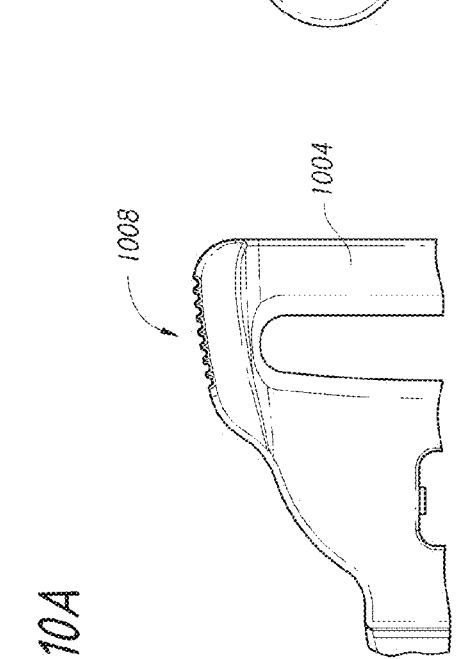

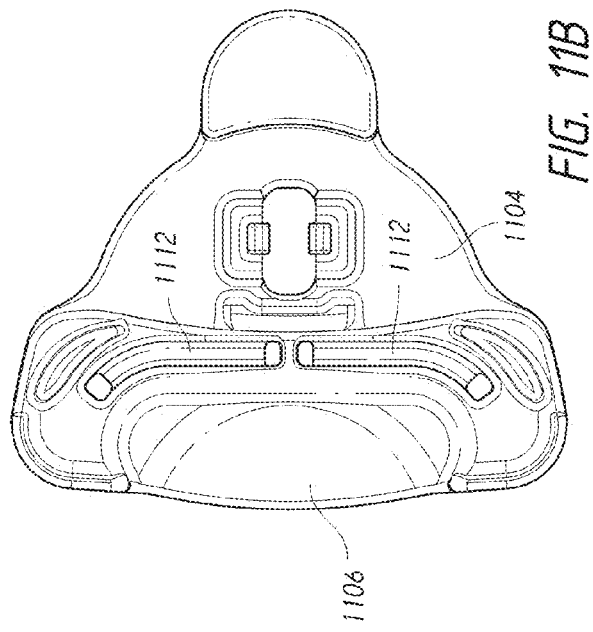
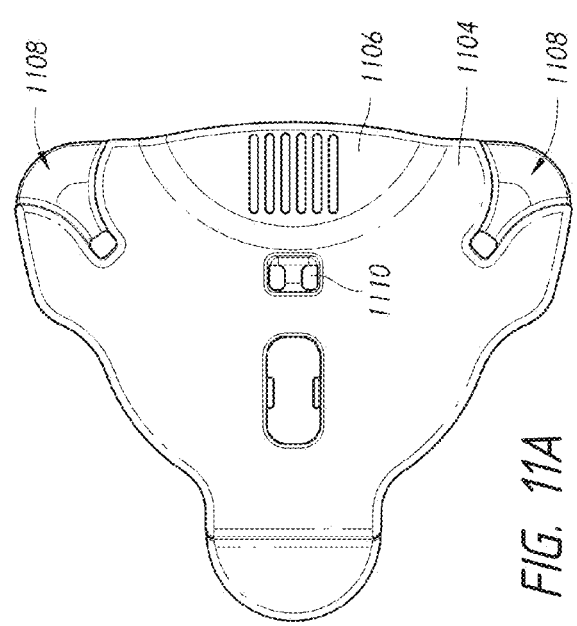
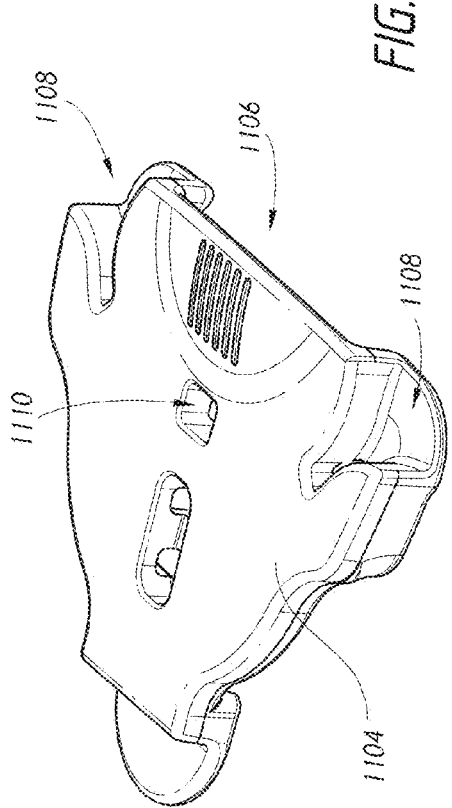
FIG. 11B
FIG. 11C
FIG. 11A

COUPLING MEMBERS FOR CLOSURE DEVICES AND SYSTEMS

CROSS-REFERENCES TO RELATED APPLICATIONS

This application claims priority to U.S. Patent Application No. 61/722,022 filed Nov. 2, 2012 entitled "COUPLING MEMBERS FOR CLOSURE DEVICES AND SYSTEMS," the entire disclosure of which is hereby incorporated by reference, for all purposes, as if fully set forth herein.

BACKGROUND OF THE INVENTION

The present invention is related to coupling devices for various articles, such as braces, medical devices, shoes, clothing, apparel, and the like. Such articles often include coupling devices, such as buckles, straps, and the like, that allow the article to be placed and roughly fit about a limb. Conventional buckles and/or other closure devices, however, often are limited in there usefulness. For example, Velcro® straps and/or components are often employed in coupling devices. A common example invovles straps that may include Velcro® surfaces that allow the straps to be tensioned and folded back and coupled on itself. Such Velcro® surfaces, however, often get filled or cluttered with dirt and/or debris, which limits the usefulness and/or life of such straps. Additionally, various buckles that are used in coupling devices often allow a user to uncouple or release the buckle with the article is fully tensioned. The uncoupling of the buckle may be purposeful or accidental, such as when the buckle contacts nearby objects. Releasing the tensioned article may cause the limb to be unsupported, which may subject the limb to damage, and/or may cause the user to trip, fall, or otherwise lose concentration during an activity. Due to the limitation of conventional buckles and closure devices, improved closure devices are desired.

BRIEF SUMMARY OF THE INVENTION

The present invention generally provides improved closure devices that may be used for closure various articles, such as braces, medical devices, shoes, clothing, apparel, and the like. According to one aspect, a coupling device for coupling opposing portions of an article is provided. The coupling device includes a female component having a main body portion and a coupling aperture that includes a recessed portion. The coupling device also includes a male component having a main body portion and a coupling member. The main body portion of the male component has a proximal end and a distal end. The coupling member of the male component is positioned on the distal end of the main body.

The coupling member includes a tab that extends from the main body portion and a flange that extends from the tab. The tab and/or flange are insertable within the coupling aperture of the female component to couple the male and female components together. The male and female components are coupled via engagement of a surface of the tab and a lip of the coupling aperture. When the male and female components are coupled together, the flange is positionable within the recessed portion of the female component to maintain a coupled engagement of the male and female components.

The closure device further includes a tension member component that is configured to couple a tension member with the proximal end of the male component. The tension member is configured to tension the male and female components. The male and female components are not releasable from the coupled engagement while under tension via the tension member. The coupled male and female components have a cross sectional area and the coupled components exhibit a failure strength of between about 560 and 840 Newtons per square centimeter of cross sectional area.

In some embodiments, the tension member is a strap and the proximal end of the main body includes a D-ring around which the strap is positioned. In other embodiments, the tension member is a lace and the proximal end of the main body includes a channel throughwhich the lace is inserted or otherwise disposed. In such embodiments, a proximal end of the lace is coupled with a reel assembly. The lace is tensionable by operation of the reel assembly to tension the male and female components. In some embodiments, the tension member is a lace and a reel assembly is coupled with a top surface of the male component. In such embodiments, the lace is coupled with the reel assembly and is tensionable thereby.

In some embodiments, the article is a brace and the female component is coupled with one side of the brace while the male component is coupled with an opposing side of the brace. Such a configuration allows the brace to be opened and closed about a limb of a patient by coupling and uncoupling the male and female components. The female and/or male component may be coupled with the brace via one or more of the following attachment methods: stitching a flange of the main body to the brace, inserting a rivet through an aperture of the main body and into the brace, injection molding the female component into the brace, adhesive bonding the main body to the brace, RF welding the main body to the brace, heat welding the main body to the brace, and the like. When coupled together, the male and female components have a low profile about a surface of the brace so as to minimize contact between the male and female components and surrounding objects. In some embodiments, the male and female components are lockable in the coupled engagement to prevent uncoupling of the male and female components.

In some embodiments, the female component has an arcuate configuration that corresponds to a shape of the article (e.g., brace). In such embodiments, the male component may have a generally planar configuration. Tensioning of the male and female components via the tension member may cause the male component to rotate into an increased engagement with the female component. In some embodiments, the coupling component includes an audible feedback mechanism that provides audible feedback to a user that indicates coupling or uncoupling of the male and female components. The audible feedback mechanism may include a post that is coupled with the main body of the female component and a flange member that is coupled with the main body of the male component. The flange member may snap into engagement with the post to produce the audible feedback as the male and female components are coupled together. In some embodiments, the proximal end of the main body of the male component may include an arcuate recess that allows the male component to be gripped by a user during coupling or uncoupling of the male and female components.

According to another aspect, a coupling device is provided. The coupling device includes a female component that includes a main body portion having a top surface and a bottom surface and a coupling aperture. The coupling device also includes a male component that includes a main body portion having a top surface and a bottom surface and a coupling member. The coupling member also includes a top surface and a bottom surface. The top surface of the coupling member is offset from the bottom surface of the main body portion and the coupling member is insertable within the coupling aperture of the female component to couple the male and female components together. The male and female components are tensionable via a tension member and are non-releasable from a coupled engagement while under tension. When the male and female components are coupled together, the top surface of the male component is aligned with the top surface of the female component and the bottom surface of the coupling member and/or male component is aligned with the bottom surface of the female component. The coupled male and female components have a cross sectional area and the coupled components exhibit a failure strength of between about 560 and 840 Newtons per square centimeter of cross sectional area.

The male and female components are coupled together by engagement of a surface of the coupling member with a lip of the coupling aperture. In some embodiments, a proximal end of the male component is coupled with the tension member. In some embodiments, the tension member is lace and the proximal end of the main body includes a channel throughwhich the lace is inserted, or the proximal end of the main body includes a reel assembly that couples with the lace and is operable to tension the lace.

In some embodiments, the coupling device is attached to a brace to allow the brace to be opened and closed about a limb of a patient by coupling and uncoupling the male and female components. In such embodiments, the female component is coupled with a side of an opening of the brace and the male component is coupled with an opposing side of the opening of the brace. In some embodiments, the main body of the female component includes a post and the main body of the male component includes a flange member. The flange member is configured to snap into engagement with the post as the male and female components are coupled together to produce audible feedback.

According to another aspect, another coupling device is provided. The coupling device includes a female component having a main body portion and a coupling aperture. The coupling device also includes a male component having a main body portion that includes a top surface and a relatively planar bottom surface and a coupling member that is mateable with the coupling aperture of the female component to couple the male and female components together. The coupling member includes a relatively planar top surface and a bottom surface. The relatively planar top surface of the coupling member is offset from the relatively planar bottom surface.

The male and female components are not releasable from a coupled engagement while under tension via a tension member. The coupled male and female components have a cross sectional area and exhibit a failure strength of between about 560 and 840 Newtons per square centimeter of cross sectional area. In some embodiments, the coupling aperture includes a recessed portion having a bottom surface. In such embodiments, the relatively planar top surface of the coupling member may be positioned adjacent the bottom surface of the recessed portion when the male and female components are coupled together.

According to another aspect, a method for coupling male and female coupling components is provided. The method includes mating a coupling member of a male component with a coupling aperture of a female component to couple the male and female components together. The coupling member extends from a main body of the male component and the coupling aperture is disposed within a main body of the female component. Mating of the coupling member with the coupling aperture includes: a translation movement of the male component relative to the female component and a rotational movement of the male component relative to the female component.

In some embodiments, mating of the coupling member with the coupling aperture may be performed with a single hand. In some embodiments, the male and female components may be coupled with an article and a proximal end of the male component may be coupled with a tension member that is configured to tension the male and female components upon operation of a reel assembly. In such embodiments, the method may further include tensioning the tension member via the reel assembly to tension the male and female components and thereby tighten the article about a limb of an individual. In such embodiments, the method may additionally include: releasing tension in the tension member via the reel assembly and uncoupling the male component from the female component to allow the article to be removed from the limb. The male component may not be uncouplable or releasable from the female component while some amount of tension remains in the tension member.

In some embodiments, the method may additionally include: positioning the article about the limb, folding a first side of the article over the limb with the male component being coupled with the first side of the article, and coupling the male component with the female component to close the article about the limb with the female component being coupled with a second side of the article. The method may additionally include locking the male and female components in the coupled engagement to prevent uncoupling of the male and female components. In some embodiments, the article may be a brace.

In some embodiments, the translation movement may include inserting a flange portion of the coupling member within the coupling aperture and the rotational movement may include rotating the male component so that a top surface of the flange portion is positioned adjacent a bottom surface of the female component. In such embodiments, the translational movement may include a movement in a first direction without a significant movement in an opposite direction. In some embodiments, the translation movement may be along an axis of a plane that bisects the male and female components and the rotational movement may be about an axis that is orthogonal to the plane bisecting the male and female components.

BRIEF DESCRIPTION OF THE DRAWINGS

The present invention is described in conjunction with the appended figures:

FIGS. 4A-4M illustrate various aspects and features of a closure device that may be used to close various articles.

FIGS. 5A-5E illustrate various aspects and features of another closure device that may be used to close various articles.

FIG. 6I illustrates a link or bridge component that may be used to link male and female components of a closure device together.

FIG. 7 illustrates a brace having a pair of closure devices and reel assemblies as described herein.

FIGS. 8A-9D illustrate various views of female components of a closure device.

FIGS. 10A-11E illustrate various views of male components of a closure device.

Figure 1:
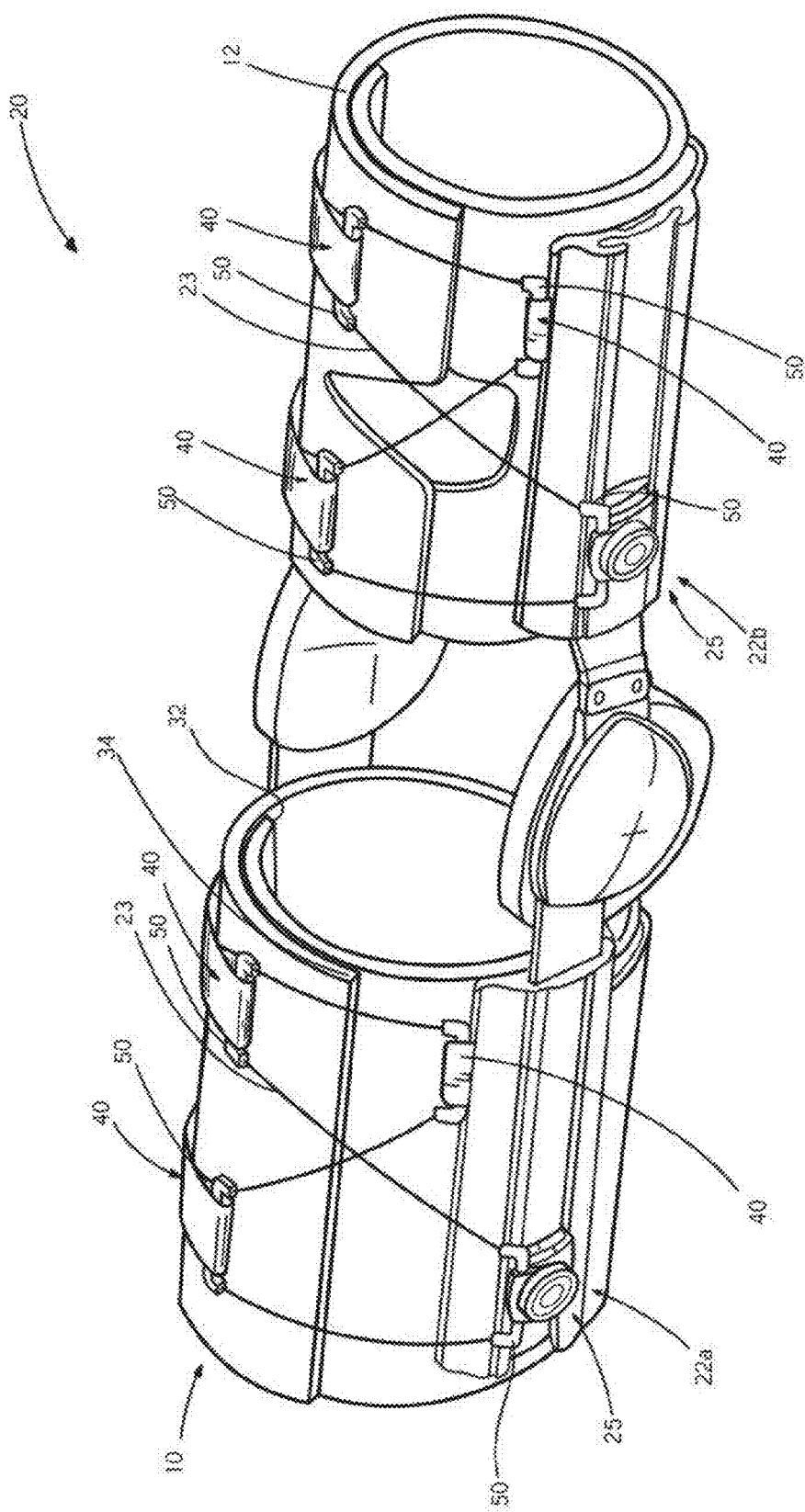
FIGS. 1-3 illustrate embodiments of a closure device being used with a brace to allow the brace to be fit about a limb of an individual.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

Embodiments described herein provide various closure devices or mechanisms (hereinafter detachable guides) that may be used to close various articles, such as braces, footwear, hats, gloves, or other apparel to allow a user to don and doff the article. For convenience in describing the embodiments, the detachable guides will be described generally as being coupled with braces to allow the braces to be quickly donned/doffed and/or tightened about a user's limb. Although the disclosure will focus mainly on braces, it should be realized that the detachable guides may be used for or with various other articles.

In some embodiments, the detachable guides may be used with lacing systems that include reel assemblies that close and tighten the brace about the user's limb. The detachable guides provide various improvements over conventional closure systems including: having a low profile when male and female components are coupled together; being intuitive and easy to use, being able to be closed without requiring the user to look at the components, being intentionally un- releasable while under load, providing audible and visual engagement, preventing accidental release (e.g., especially if used in sports bracing), working consistently when mounted on soft (e.g., stitched) and hard (e.g., molded) braces, working on flat and curved surfaces, and the like.

Most braces are designed to wrap around a part of the body and thus must be opened and closed over the body. The detachable guides described herein are placed on the brace to allow patients to quickly and easily wrap and close the brace around the body. To tighten the brace around a limb or body part, a proximal end of the detachable guide is typically coupled with a tension member, such as straps, cords, lace, and the like. For convenience in describing the various embodiments, the disclosure generally describes the tension member (e.g., straps, lace, and the like) being tensioned via a reel or dial assembly (hereinafter reel assembly). The reel assembly typically closes the article or brace, or one or more components thereof, by tensioning the tension member. For example, a knob of the reel assembly may be twisted to wind lace within a spool housing and about a spool. Although the disclosure generally describes the tension member being tensioned via a reel assembly, it should be realized that any tightening mechanism may be used and the disclosure is not limited to only those embodiments described herein. For example, in some embodiment, the tightening mechanism may include a pull-cord type device where the user grasps and pulls the pull-cord to tension the tension member. Other embodiments may use ratchet-type mechanisms that include straps or other components having ratchet teeth that interact with the ratchet device to tension the tension member.

Referring now to FIG. 1, a general description of an orthopedic brace and reel assembly closure device is illustrated. The orthopedic brace 20 illustrated in FIG. 1 is a knee brace that is tightened around a user's leg such that the knee brace substantially surrounds and protects the user's knee. Brace 20 may be tightened using a lacing configuration comprising two lacing systems 22a, 22b. The orthopedic brace 20 of the illustrated embodiment is particularly concerned with relieving and/or supporting the knee joint. Although this illustrated embodiment shows the lacing systems applied to knee braces, it is to be understood that the principles discussed herein are readily applicable to any of a variety of orthopedic braces, including ankle braces, wrist braces, foot braces, elbow braces and many other types of orthopedic braces well known to those of skill in the art.

In some embodiments, the lacing configuration of closure system comprises two distinct lacing systems 22a, 22b. In some embodiments, each lacing system 22 includes a lace or cable 23 that is threaded through portions of the orthopedic brace and attached at opposite ends to a reel assembly 25, which includes a control such as a lever, crank or knob that can be manipulated to retract the lace 23 within a spool housing (not shown) and about a spool (not shown). The reel assembly 25 may include a mechanism of release, such as a button or lever, for disengaging the reel assembly 25, to permit the lace 23 to be withdrawn freely. In other embodiments, the reel assembly 25 may be pulled upward to allow an internal spool to spin and the lace to be pulled freely. In yet another embodiment, the reel assembly 25 may be unwound (e.g., counterclockwise) to release the spool and allow the lace to be pulled, or to unwind the lace. As shown in FIG. 1, the lace 23 may be threaded in a crossing pattern along a generally forward-facing portion of the brace 20, between two generally parallel rows of side retaining members or straps 40. In another embodiment, the lace 23 may be threaded or run laterally across the brace 20. The straps 40 may consist of a strip of material attached to the brace 20 so as to define a space in which guides 50 are positioned. The lace 23 may slide through the guides 50 during tightening and untightening of the lace 23. A more thorough description of the brace 20 and lacing systems, 22a & 22b, is provided in U.S. Pat. No. 8,277,401, the entire disclosure of which is incorporated by reference herein.

The orthopedic brace 20 shown in FIG. 1 is constructed to fit a user's leg. The upper cuff 10 is formed to fit the user's thigh and curves around the thigh, generally conforming to the user's musculature. The lower cuff 12 is similar in construction to the upper cuff 10, and is formed to fit and curve around the user's calf. In some embodiments, the upper and lower cuffs 10, 12 are formed from a relatively lightweight, breathable material. In some embodiments, the cuffs 10, 12 are manufactured from a cloth, fabric, or foam-like material, or a thermoformable or non-thermoformable plastic material as would be well-known to those skilled in the art.

As shown, each of the cuffs 10, 12 are generally formed from a single piece of material that is wrapped around itself, forming two ends 32, 34 that are drawn towards each other and, in fact, may overlap. Although the ends 32, 34 are shown in an overlapping position, it should be understood that these ends might also be sized to be separated by some distance when the orthopedic brace 20 is tightened. Generally, the lace 23 may be tensioned to draw the ends 32, 34 past each other and thereby tighten the orthopedic brace 20 about the user's limbs. As is readily understood in the art, the two ends 32, 34 of brace 20 are designed to be open and fit about the user's leg. The two ends 32, 34 are then positioned over the leg and brace 20 is tightened as described above.

Figure 2:
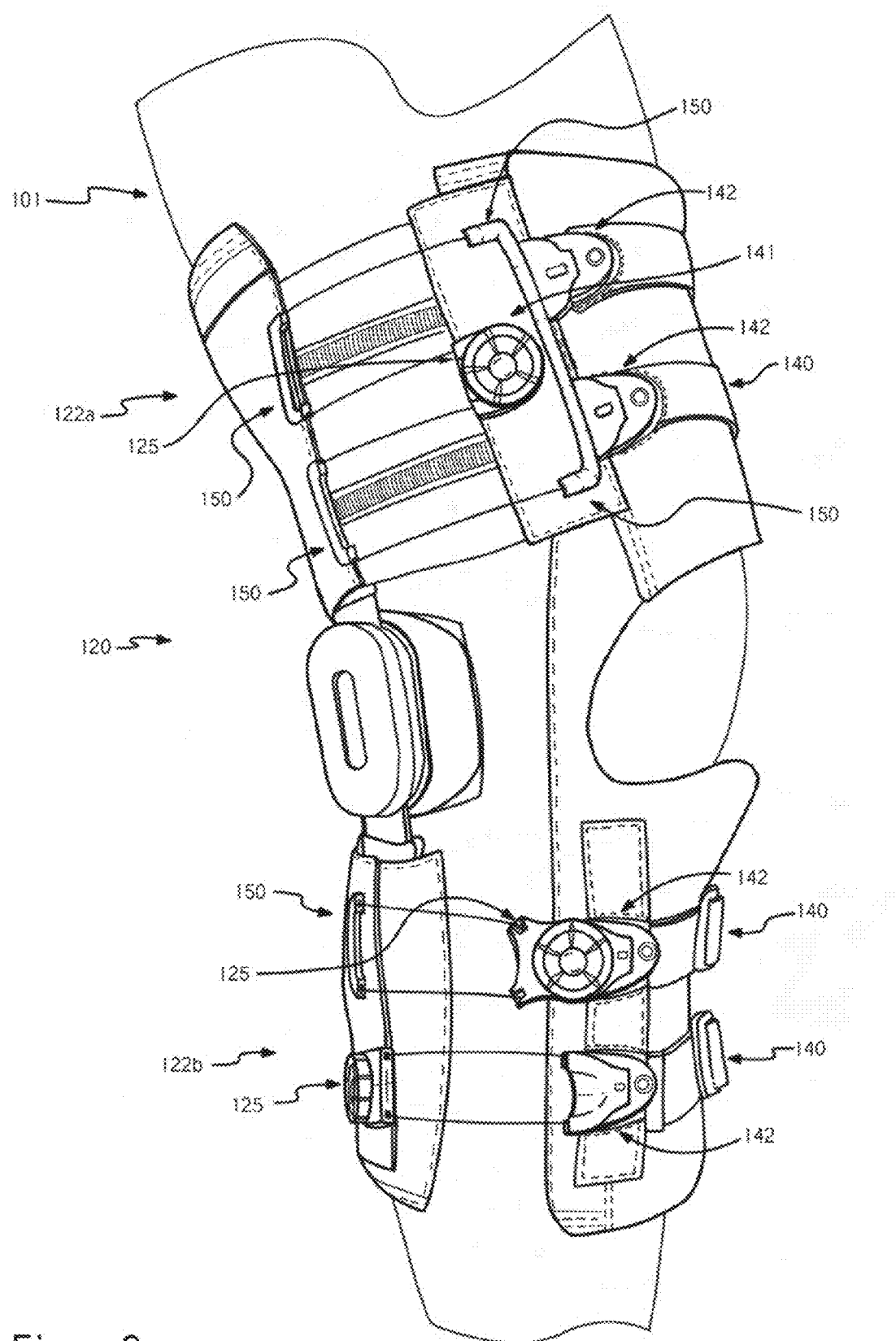
Figure 3:
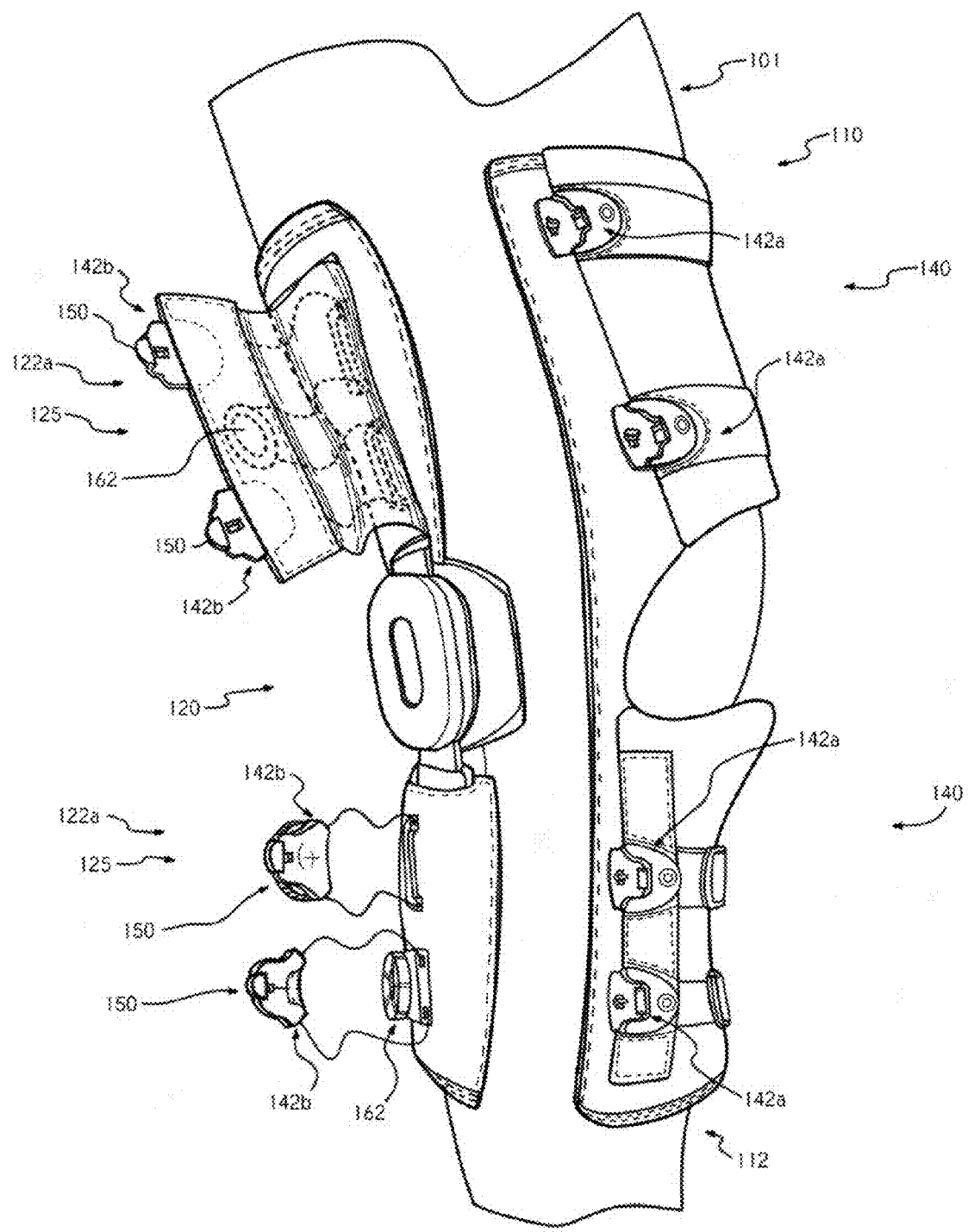

FIGS. 2 and 3 illustrate another brace 120 being fit over a user's leg 101. Brace 120 includes a closure system (e.g., 122a and 122b) that is described in more detail in U.S. Pat. No. 8,277,401 incorporated by reference herein. Brace 120 also includes a gross or macro adjustment feature that permits further opening of the brace 120 to facilitate attachment of the brace 120 to the user's leg 101, while still providing the reel assembly 125 for final tightening. The gross/macro adjustment feature may be variable length retaining members 140 that allow brace 120 to fit a wider variety of user's legs. In one embodiment, the variable length retaining member 140 includes adjustable straps. In other embodiments, a panel 141, such as those described herein, may be used. The panel 141 may be coupled with the reel assembly 125 to provide gross or macro adjustment of the brace 120.

In some embodiments, the retaining members 140 are configured to be releasably engaged with guides 150 opposite the reel assembly 125. The engagement may be by way of a quick release mechanism 142, for example the detachable guides described herein. In other embodiments, Fastex® buckles (not shown), Velcro® or other similar mechanisms known to those of skill in the art may be used. As shown in greater detail in FIG. 3, each quick release mechanism 142 may include a female component 142a and a male component 142b that are coupled together over the user's leg 101 or uncoupled therefrom in donning and doffing the brace 120 respectively. Exemplary embodiments of male and female components, 142b and 142a, are described in the applications incorporated herein by reference. In some embodiments, the female component 142a may be attached to the guide 150 while the male component 142b is attached to the retaining member, though the arrangement of components may be switched as desired. The opposite end of the retaining member 140 may be attached to the brace 120 such that tension in the lacing system 122 tensions the retaining member 140 when the quick released mechanism 142 is engaged, thereby compressing the cuffs around the user's limb.

Closure system 122 may include additional gross adjustment features in combination with the quick release mechanism 142 to provide a gross or macro adjustment of the brace 120 (and/or adjustment of a closing pressure of the brace) prior to use of the reel assembly 125 to tighten the brace about the limb. For example, the closure system 122 may include ladder locks (e.g., Fastex Slider®) which allow the retaining members 140 to be lengthened or shortened as needed. Though shown with two retaining members 140, as with the other embodiments disclosed herein in some embodiments, the number of retaining members 140 may be varied. In some embodiments, three, four, five, six or more retaining members 140 may be desirable.

FIG. 3 shows one embodiment of the brace 120 in a partially open configuration. The quick release mechanism 142 have been disconnected leaving the guides 150 attached to the brace and releasing one end of the retaining member 140. To remove the brace 120, the user may then open the cuffs 110, 112 and slide the brace from the user's leg 101. Prior to releasing the quick release mechanism 142, the user may release tension in the closure system 122 by releasing the reel assembly 125 by, for example, pulling outwards on the reel assemblies 162.

On advantage of using the above described braces is the increased ability of the brace to fit a conical shape and/or adjusting shape, such as a leg, arm, or any other part of a user's body. The ability of the brace to fit a conical shape is provided by the lacing system. For example, as the brace is fit about a conical shape (e.g., the leg) and the lace wound via the reel assembly, an upper portion of the brace contacts the conically shaped object. As the lace is wound, the lace adjusts until the lower portion of the brace also contacts the conically shaped object (e.g., the leg). Additional winding of the lace will result in an approximately equal tension throughout the lace since the lace is able to slide relative to the lace guides, which provides a relative even pressure of the brace about the conically shaped object. Accordingly, the brace 20 fits well on the conical shape.

Similarly, the brace is able to adjust to changes in the shape of the object, such as changes in the shape of a leg (or other body part) due to flexing and/or relaxing of the muscle. For example, as a leg is flexed and assumes a more cylindrical shape, the lace is able to slide relative to the lace guides so that a bottom portion of the brace opens or widens as a top portion contracts or shrinks. Conventional braces typically do not adjust in this manner and thus, when a patient flexes their leg (or other body part) the brace is typically forced or encouraged to move, such as downward against the knee. Because the lace is able to slide relative to the brace and guides and the brace is able to adjust to changes in shape, the fit or hold of the brace about the body part is increased.

The detachable guides similarly provide several advantages over conventional brace closure technology. For example, the use of buckles, Velcro®, or other similar mechanisms often require the user to use both hands in opening and/or closing the brace. For example, to couple the male and female components of a buckle, the user is often required to grasp the female component with one hand while the male component is being inserted into the female component to ensure that the female component will remain in position during coupling of the components. Similarly, in closing Velcro® straps, the user often must thread a distal end of the strap through a d-ring or hook before tensioning and folding the strap back on itself. The user often must hold the d-ring or hook while the strap is being threaded through the d-ring. Requiring the use of both hands is often inconvenient, frustrating, and/or annoying to the user, and potentially not an option for dexterity compromised or handicapped individuals. Likewise, donning and doffing the brace in this manner may be needlessly time consuming.

The use of buckles, Velcro®, or other similar mechanisms also allows the brace to be uncoupled while tension remains in a strap and/or while tension is being applied to a tension member via a reel assembly or other tightening mechanism. For example, the brace may be fit about the user's limb and a reel assembly used to tighten the brace about the limb. Without releasing tension in a strap or lace of the brace, the user may unbuckle or unstrap the brace to release brace pressure and/or remove the brace, such as for adjustment. Upon refitting the brace about the limb, the reel assembly may again be used to retighten the brace about the limb. Continual retightening of the brace in this manner causes an increased amount of the lace to be wound about the reel assembly's spool, which limits the amount of lace that is available for tightening the brace. Continual winding of the lace about the reel assembly's spool also results in overstorage of the lace within the reel assembly's housing, which may negatively affect the performance of the reel assembly.

The detachable guides described herein remedy these and other issues associated with conventional braces as described hereinbelow. For example, the detachable guides have relatively low profile in a closed configuration that helps avoid snagging or catching of objects close to the user. In some embodiments, the detachable guides may be configured to lie nicely under an individual's clothing to allow the brace to be worn without being noticed by others. The detachable guides may also be aesthetically pleasing compared with conventional guides and have a lower profile that offers a lighter and more sleek look and/or feel. The detachable guides also may be coupled and/or uncoupled with one hand to allow the user to don and doff a brace or other article relatively easily. The detachable guides also remain coupled while under tension or load (e.g., via the tension member) to avoid problems of over storage of the lace within the reel assembly or other tightening mechanism, such as by continual shortening of the lace as described above. The detachable guides further allow the male component to be fully disengaged from one side of the brace, which allows the brace to be fully opened and laid flat.

Figure 4A:
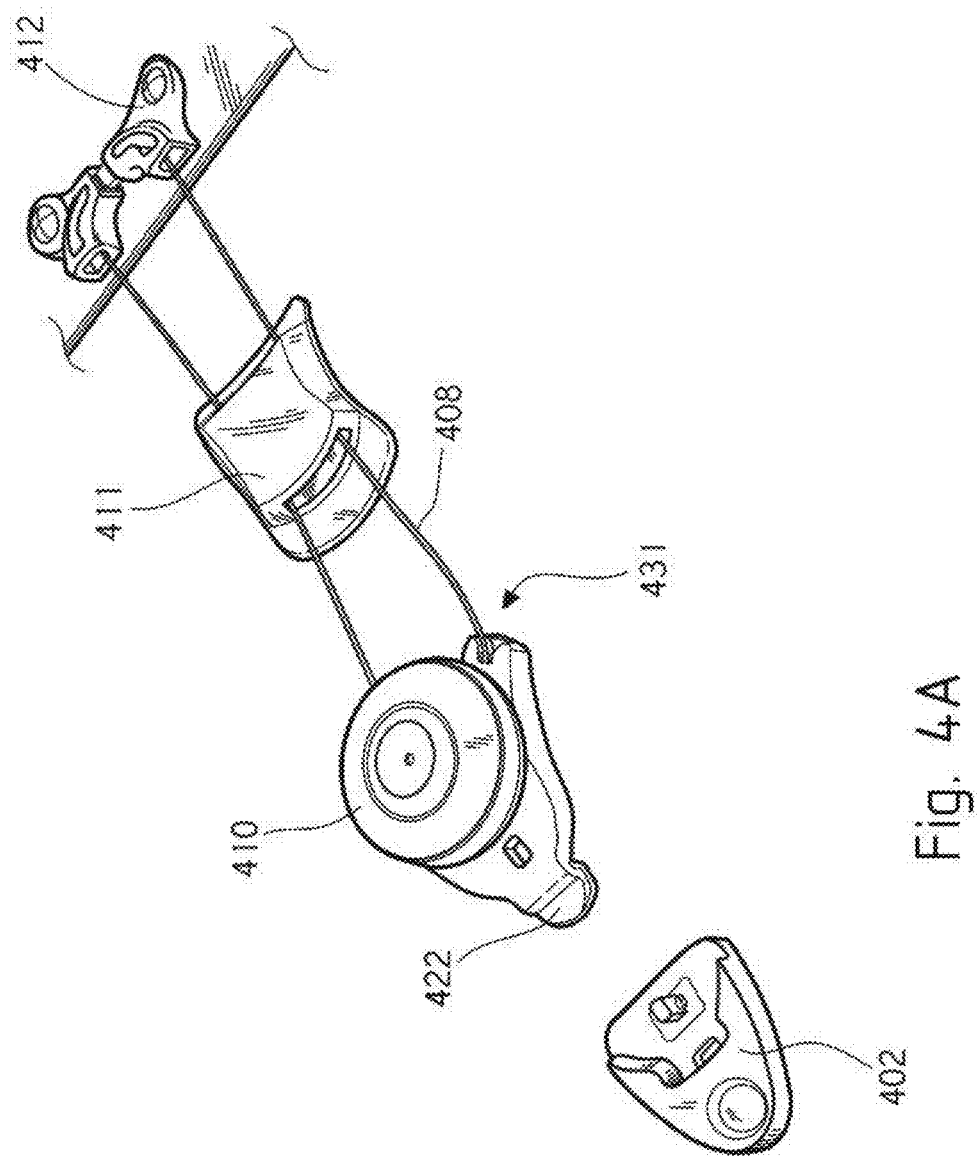
Figure 4B:
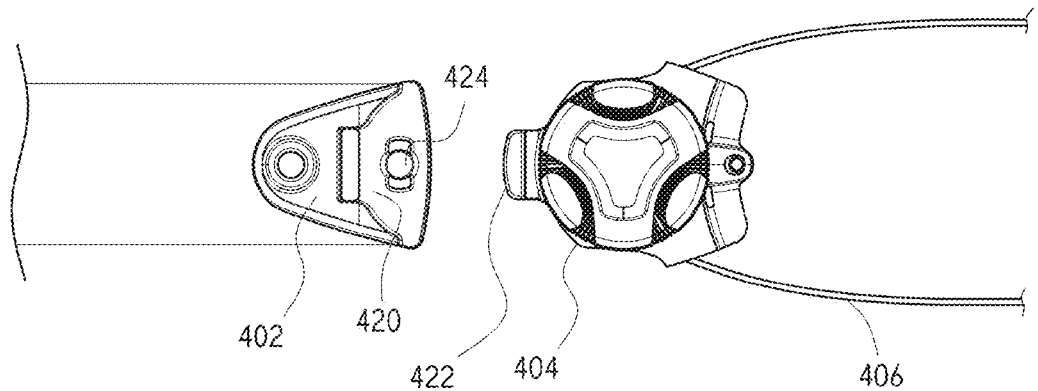
Figure 4C:
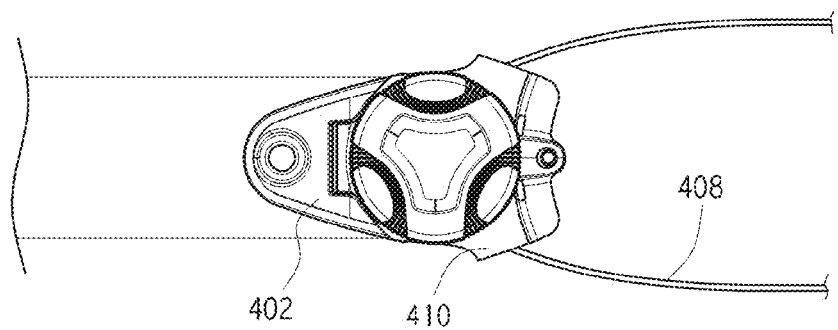
Figure 4D:
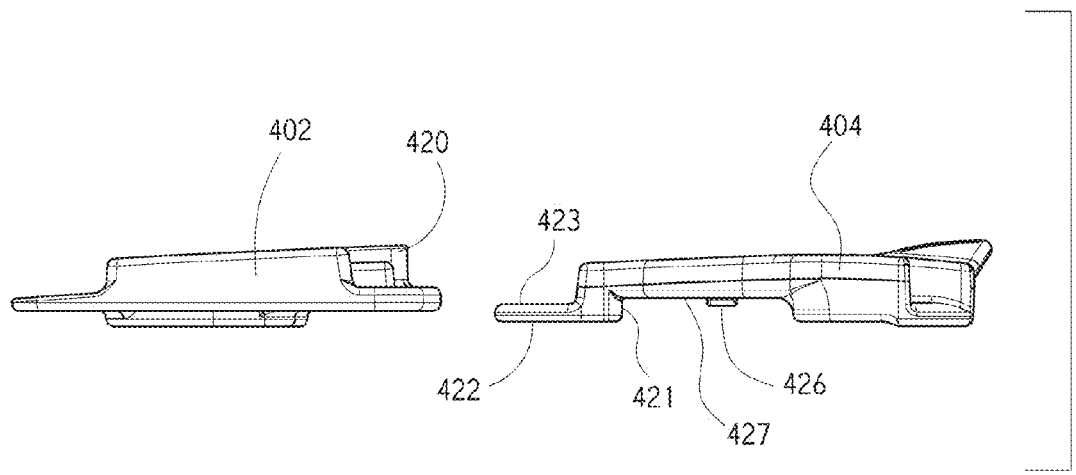
Figure 4E:
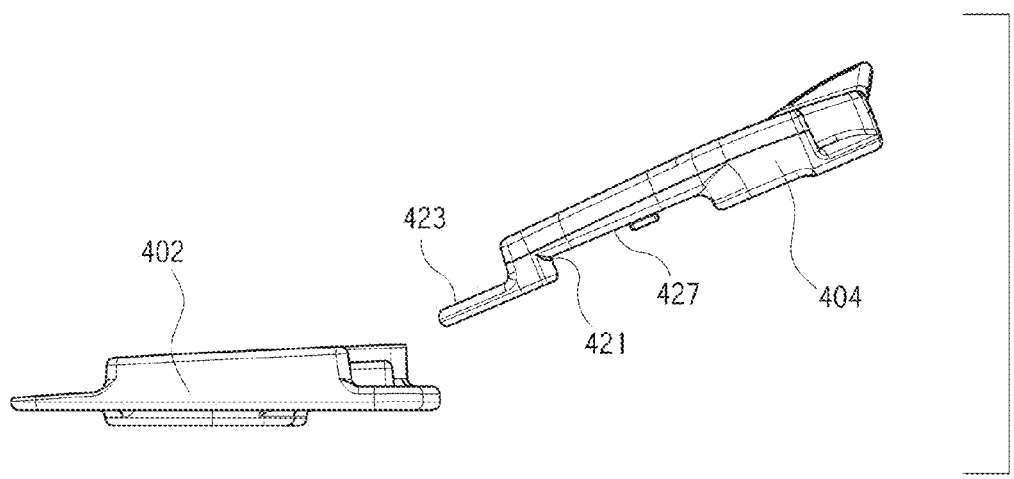
Figure 4F:
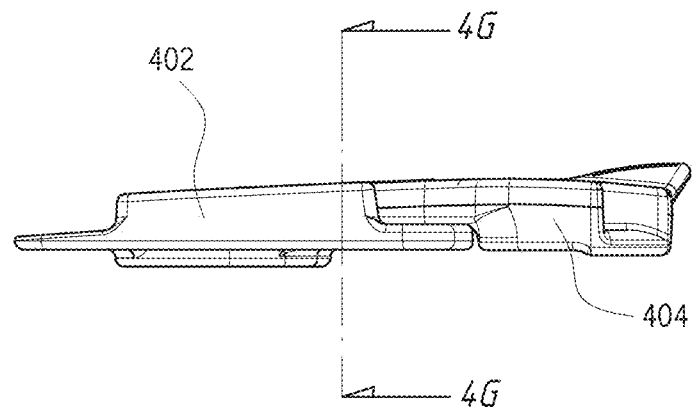
Figure 4G:
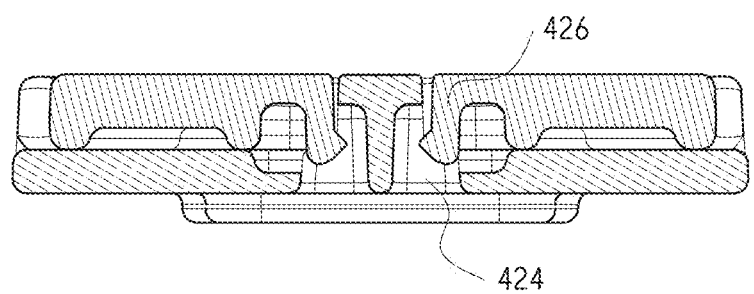
Figure 4H:
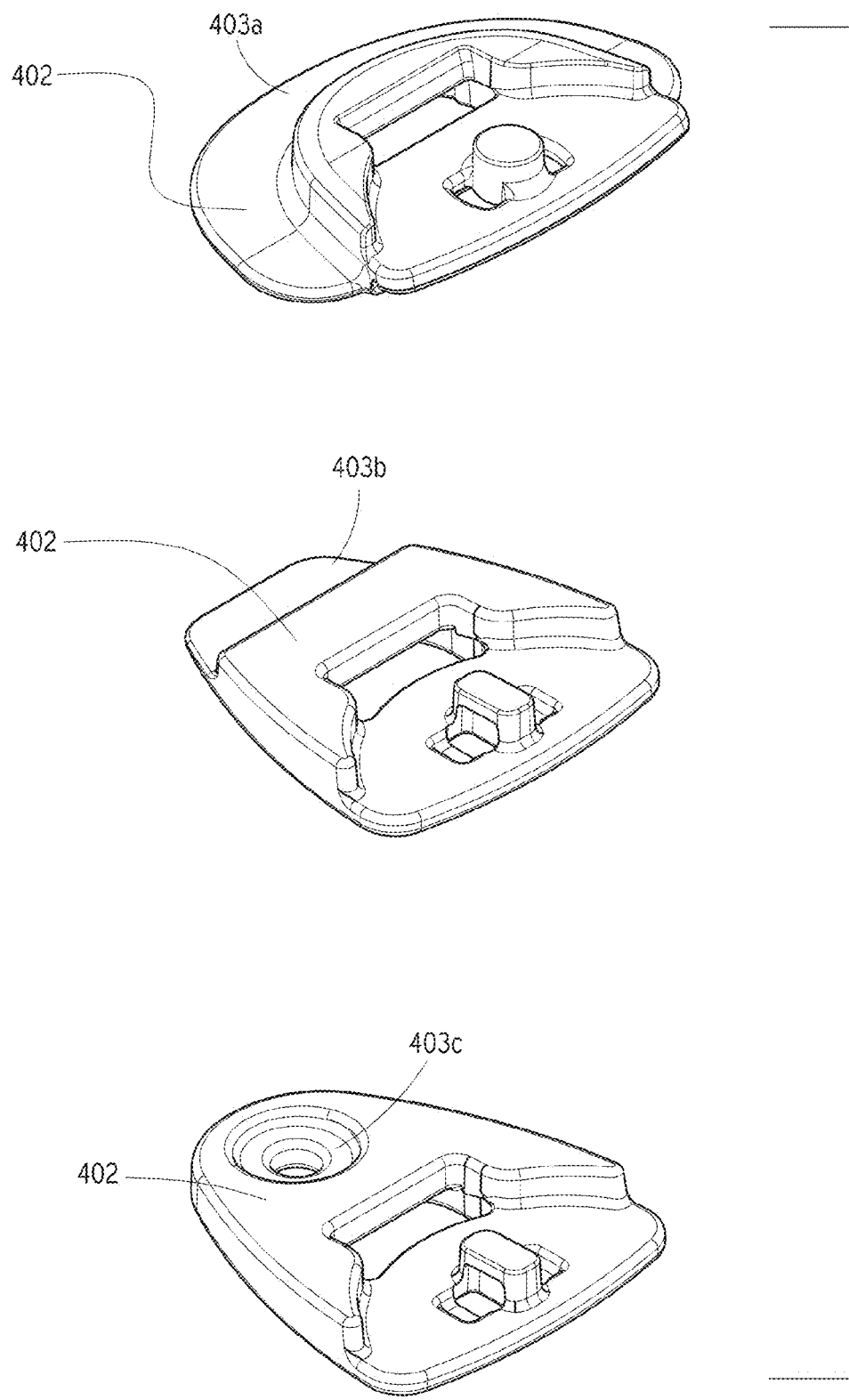
Figure 41:
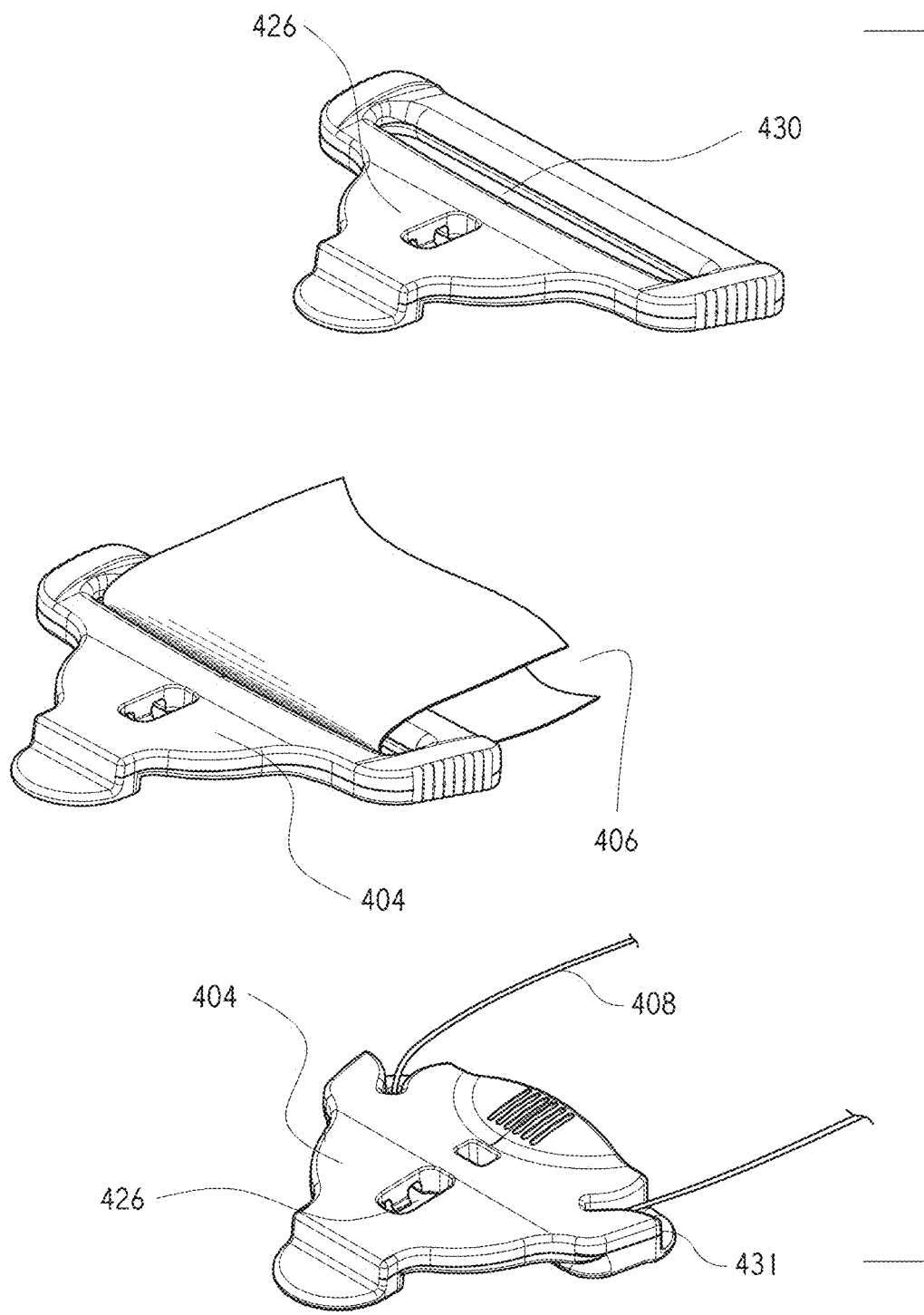
Figure 4J:
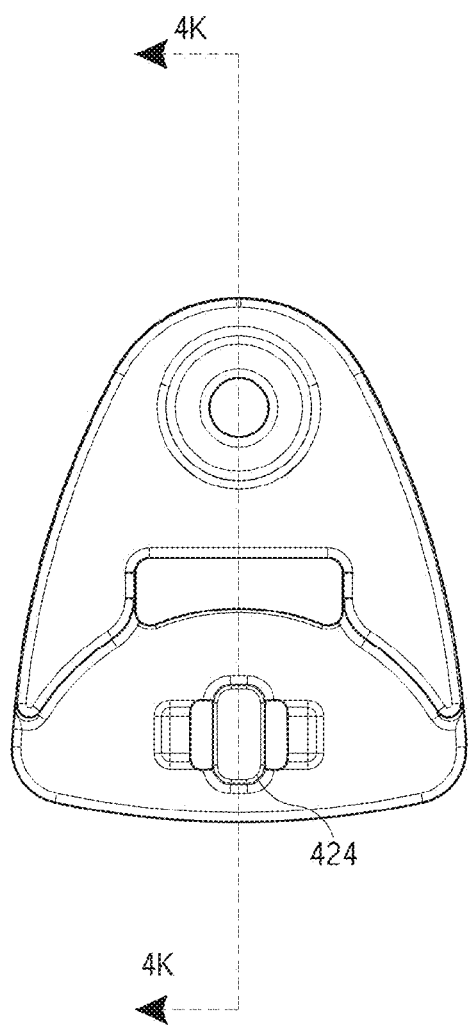
Figure 4K:
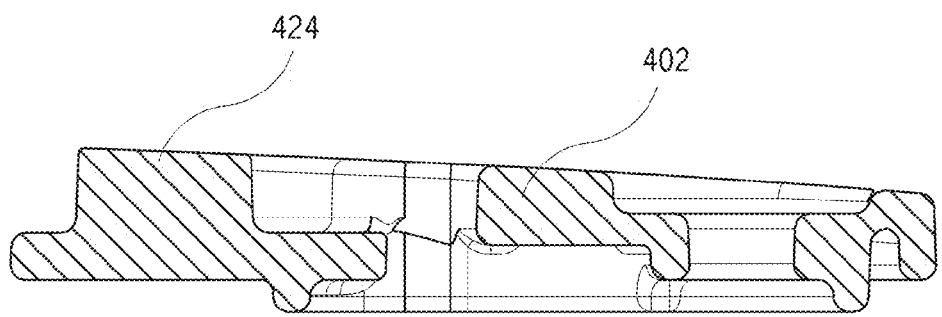
Figure 4L:
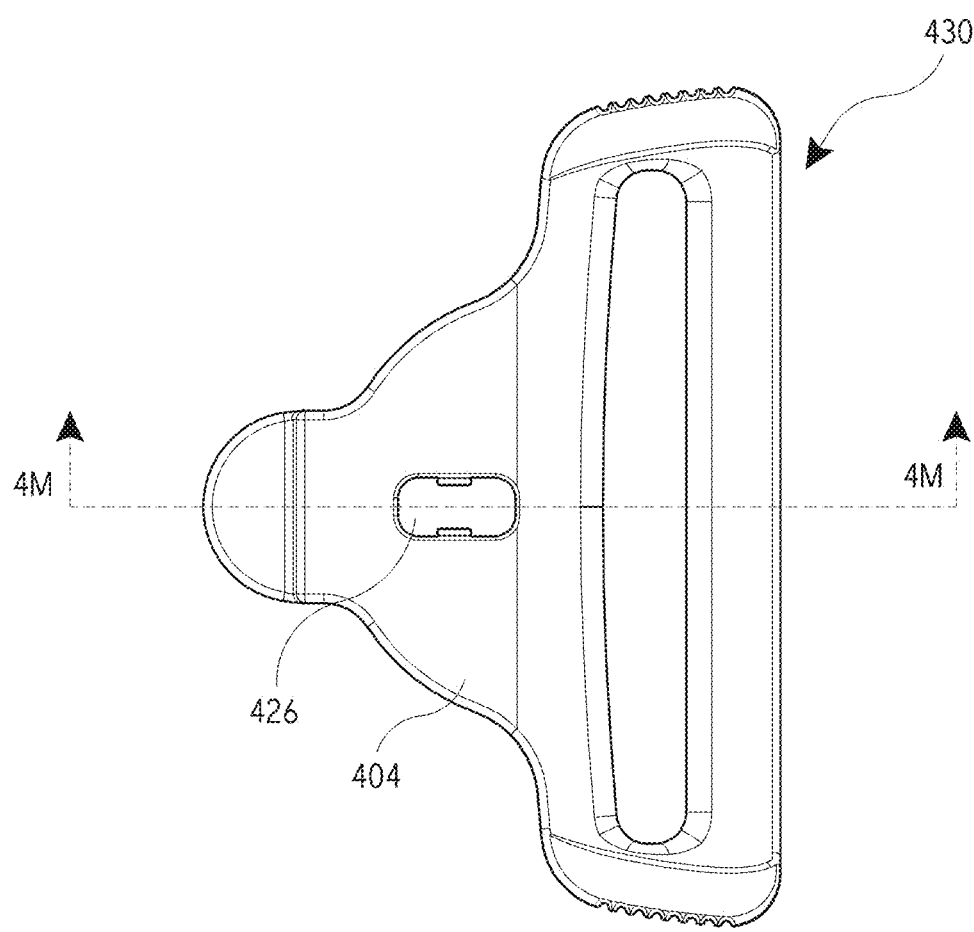
Figure 4M:
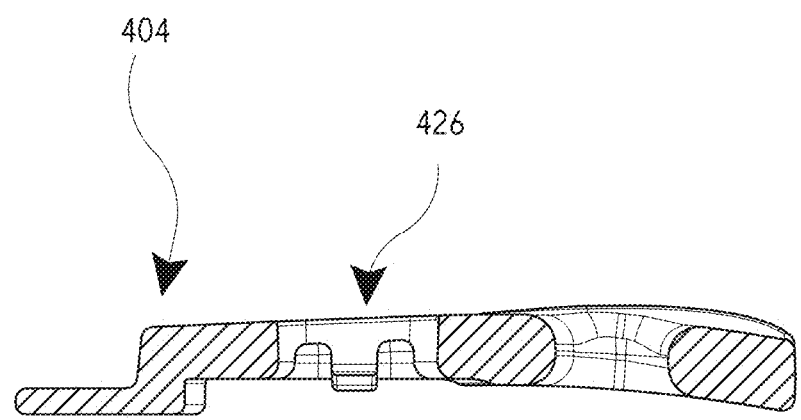
Figure 4N:
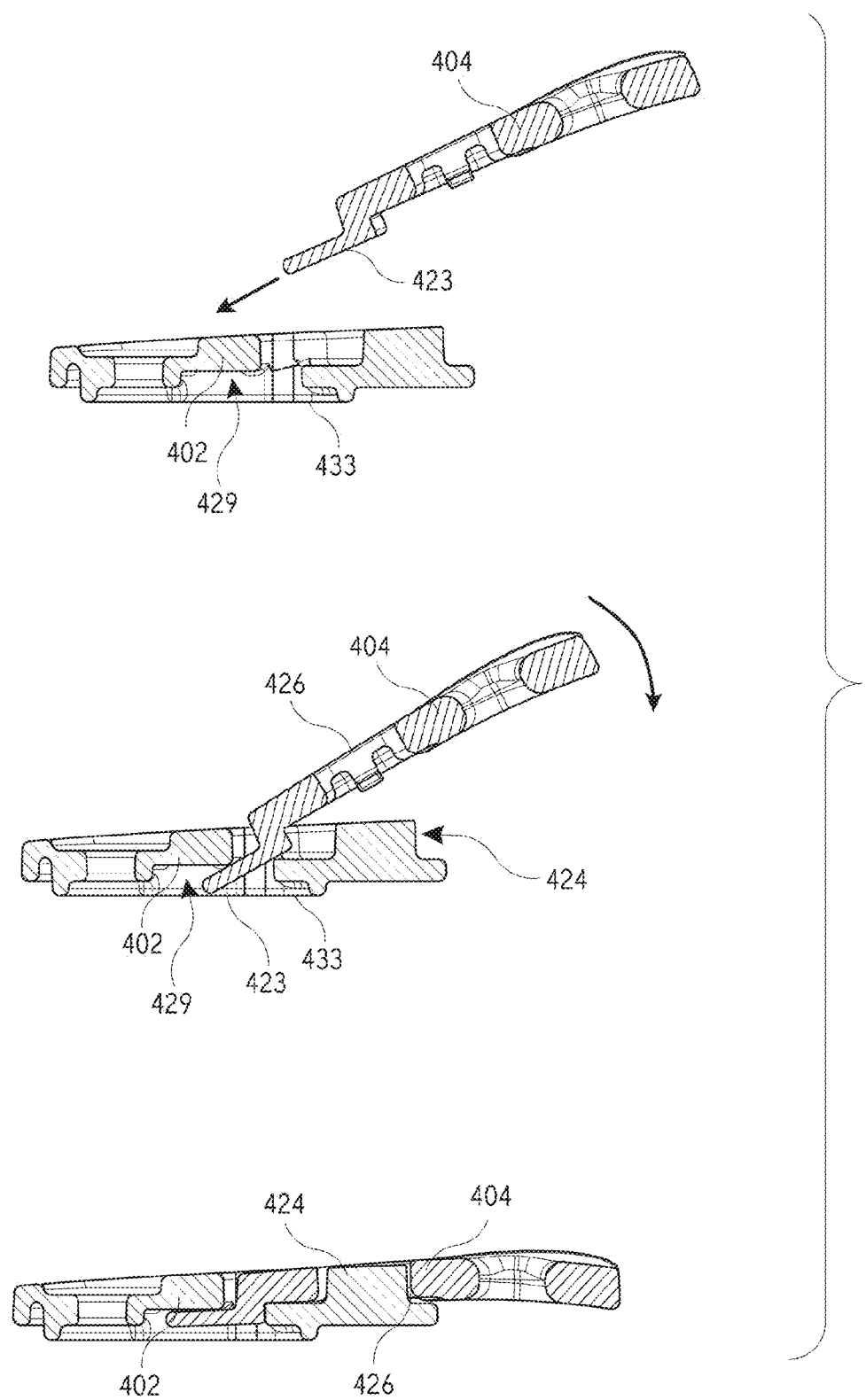
FIG. 4N illustrates a process of coupling a male component of a closure device with a female component of the closure device.

Referring now to FIGS. 4A-4N, illustrated are various embodiments of a detachable guide. FIGS. 4A-C shows a female component 402 and a male component 404 of the detachable guide. The male component 404 is inserted within the female component 402 to couple the two components together. Specifically, a coupling member 422 of the male component 404 is mated with a coupling aperture 420 of the female component 402 to couple or mate the two components. In some embodiments, the coupling member 422 includes a stepped protrusion 422 that is positioned at a distal end of a main body of male component 404. As shown in greater detail in FIGS. 4D-E, the stepped protrusion 422 includes a tab 421 that extends orthogonally downward from the main body of male component 404. A flange 423 extends orthogonally from a distal end of tab 421 such that the coupling member 422 has a generally L-shaped or Z-shaped profile. The flange 423 has a relatively planar top surface that is offset from a relatively bottom surface 427 of the main body of male component 404. The term "relatively planar surface" as used herein means that the surface is generally flat, but may include surfaces that are slightly curved (e.g., up to 5-10%) and/or include other surface irregularities. The tab 421 and flange 423 will be referred to generally hereinafter as stepped protrusion 422.

As shown in greater detail in FIG. 4N, the coupling aperture 420 of the female component 402 includes an aperture and a recessed portion 429 that is positioned immediately adjacent the aperture. The recessed portion 429 is typically a recess within a bottom portion of the main body of female component 402. In coupling the male component 404 and the female component 402, the flange 423 and/or tab 421 are insertable within the coupling aperture 422 such that the relatively planar top surface of flange 423 is positioned immediately adjacent and under the recessed portion 429 of female component 402. When the components are coupled together, a proximal or rear surface of the tab 421 engages with a lip or distal surface of the coupling aperture 420. Engagement of the rear surface of the tab 421 and the lip of coupling aperture 420 maintains a coupled engagement of the male and female components, 404 and 402, when tension is applied between the components, such as when a tension member is tensioned via a reel assembly and the like. Further, the configuration of the coupling member/stepped protrusion 422 and the coupling aperture 420 results in a shear force being applied to these components as the male and female components, 404 and 402, are tensioned, rather than a bending force being applied as in conventional buckles. As described hereinbelow, the application of the shear force rather than a bending force allows the male and female components, 404 and 402, to withstand far greater tension loads before failure than those achievable by conventional buckles. For convenience in describing the embodiments, the coupling aperture 420 will be generally referred to hereinafter as a stepped recess 420.

In some embodiments, the male component 404 may include an audible feedback mechanism that provides audible feedback to a user that indicates coupling and/or uncoupling of the male and female components, 404 and 402. For example, in some embodiments the male component includes a flange member or pair of snap tabs 426 that fit over, or otherwise engage, a grooved post 424 of the female component 402 when the male and female components, 404 and 402, are mated together. The snap tabs 426 may make an audible "snap" sound when mated with the grooved post 424 to audible alert the user that the male and female components, 404 and 402, are coupled together. For example, the snap tabs 426 may snap into engagement with the grooved post 424 to produce the audible feedback during coupling of the components. The snap tabs 426 may also provide tactile feedback that coupling of the components has occurred so that the user is able to tactually recognize when coupling occurs.

The male component 404 typically includes a tension member component that allows a proximal end of the male component 404 to be coupled with a tension member, such as a strap or lace. The tension member (e.g., strap, lace, and the like) may be tensioned via a tensioning or tightening mechanism to apply tension to the male and female components, 404 and 402. The configuration of the stepped protrusion 422 and the stepped recess 420 of the male and female components, 404 and 402, prevents the male and female components from being released or uncoupled while an appreciable amount of tension exists in the tension member. For example, as described herein, to couple the male component 404 with the female component 402, the stepped protrusion 422 is typically inserted within the stepped recess 420 at an angle and then the male component 404 is rotated downward relative to the female component 402 to position the flange 423 adjacent the recessed portion 429 of the stepped protrusion. Tensioning of the male and female components, 404 and 402, pulls the stepped protrusion 422 proximally to engage the stepped protrusion 422 with the lip of stepped recess 420. An appreciable amount of tension in the tension member prevents the male component 404 from being counter-rotated (i.e., rotated upward), which is typically necessary for uncoupling of the male and female components, 404 and 402. Accordingly, the male and female components, 404 and 402, are not releasable while an appreciable amount of tension remains in the tension member. The reference to an appreciable amount of tension means that some minimal amount of tension may exists in the tension member while the components are uncoupled, but the tension is far less than a tension that is normally applied to close an article about a limb.

As shown in FIGS. 4A-C, in some embodiments the male component 404 may include a tightening mechanism or reel assembly 410 that is coupled or attached with a top surface of the male component 404. Lace 408, which in the illustrated embodiment is the tension member, may be inserted or disposed within a channel 431 of the male component 404. The channel 431 may connect with a similar channel or an aperture of the reel assembly 410 to allow the lace to be wound within a spool housing (not shown) and about a spool (not shown) of reel assembly 410. The reel assembly 410 is used to tension the lace 408 and/or release tension therefrom as described above. In such embodiments, a user is able to easily don and doff a brace and tighten the brace with one hand. For example, a user may easily place the brace over a leg or other body part, grasp the male component 404 and reel 410 with a single hand, pull the male component and reel over the leg or body part with the same hand, couple the male component with the female component 402 by inserting the stepped protrusion 422 into the stepped recess 420, and subsequently tension the lace 408 by rotating the reel 410. In this manner, the detachable guide is significantly easier and quicker to use than other closure systems.

A distal end of the lace 408 may pass through and/or around a guide 412 that is coupled with an opposite side of the brace. Similarly, a floating or mid-point guide 411 may be positioned between the reel assembly 410 and guide 412. The lace may be inserted through channels of the floating guide 411 for lace management purposes and/or to keep the lace 408 aligned about a desired lace path.

FIGS. 4D-F illustrate side views of the male and female components, 404 and 402. The stepped protrusion 422, which is inserted into the stepped recess 420 of female component 402, is evident in the side views of FIGS. 4D-F. FIG. 4D-F also illustrate the coupling process of the male and female component, 404 and 402. FIG. 4F further illustrates that when coupled, the mated components have a low profile. The profile of the mated components may be approximately continuous. Stated differently, the top surface of the male component 404 may be roughly aligned and/or match a contour of the top surface of the female component 402 as illustrated. The bottom surfaces of the two components may similarly be aligned and/or contour matched. As can be readily understood with reference to FIG. 4F, the mated components may lie flat against the brace and thus, be virtually free from snagging nearby objects that the user may pass.

Figure 4O:
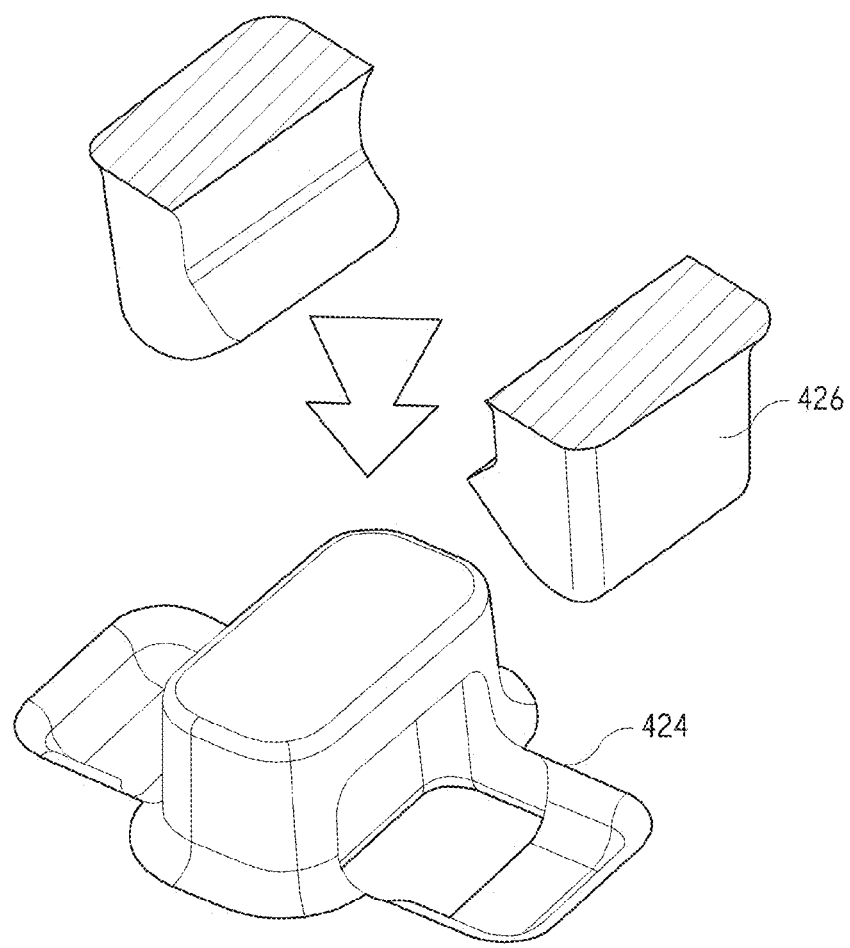
FIGS. 4O and 4P illustrate enlarged perspective views of snap tabs of a male component and a grooved post of female component of a coupling device.
Figure 4P:
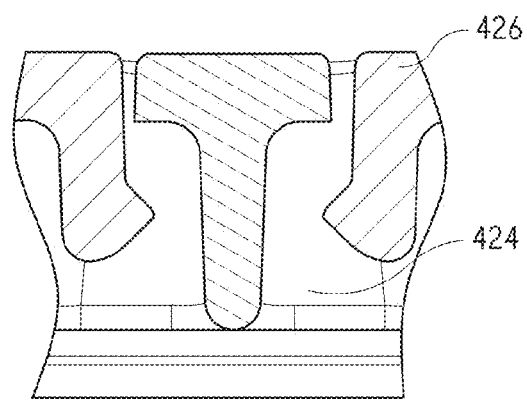

FIG. 4O illustrates a close up perspective view of the snap tabs 426 and grooved post 424 in an uncoupled state while FIG. 4P illustrates a side view of the snap tabs and post in a coupled state. Each snap tab 426 includes an inward facing flange that fits within the groove of grooved post 424 when coupled together. A spacing between the inward facing flanges is smaller than the outer diameter of the grooved post 424. As such, as the snap tabs 426 are pressed onto grooved post 424 and around an enlarge top end, the snap tabs flex outward slightly. The snap tabs 426 then snap back into an un-flexed position as the tabs 426 slide past the enlarged top end and encounter the grooves of post 424. The outward flexing and inward snap of the tabs 426 produces the audible snap sound and tactile feel previously described. In some embodiments, the snap tabs 426 and grooved post 424 may releasably hold or lock the male component 404 and female component 402 in the low profile mated configuration.

FIG. 4H illustrates various embodiments of female component 402. As shown, female component 402 may include a relatively small flange 403b that extends around one or more sides of its perimeter, or a large flange 403a that extends around a majority of its entire perimeter. The flange, 403a and/or 403b, may be stitched into fabric or other material of the brace. In some embodiments, the female component 402 may include an aperture 403c that allows the female component to be riveted or snapped onto the brace. In other embodiments, the female component 402 may be adhered, heat welded, RF welded, injection molding, and the like onto the brace or article, or onto a portion or component thereof. For example, the female component 402 may be injection molded to the brace or to a strap that is ultimately coupled to the brace. The male component 404 may similarly be attached to the brace or a component thereof, such as a strap and the like.

FIG. 4I illustrates that in some embodiments, the proximal end of the male component 404 may include a d-ring or hook 430 through which a strap 406 is inserted. The strap 406 may be adjustable and/or tensionable as previously described. In other embodiments, the proximal end of the male component 404 may include a channel 431 through which lace 408 is inserted or disposed. In such embodiments, the proximal end of the male component 404 may function as a guide for the lace 408.

FIGS. 4J-N illustrates other embodiments of a detachable guide. The detachable guide includes a male component 404 and a female component 402 that are similar in configuration to those previously described. For example, the male component 404 includes a stepped protrusion that is insertable within a recess of the female component to couple the two components together. In this embodiment, however, the audible and tactile feedback is provided via a capped post 424 of female component 402 and a corresponding aperture 425 of male component 404. The aperture 426 includes a pair of inward facing flanges that are pressed and snap over a cap of post 424. The post 424 and aperture 426 releasably hold or lock the male component 404 and female component 402 in the low profile mated configuration. FIG. 4K illustrates a cross-section view of the female component 402 illustrated in FIG. 4J while FIG. 4M illustrates a cross-section view of the male component 404 illustrated in FIG. 4L.

FIG. 4N illustrates a process of coupling the male and female components, 404 and 402. FIG. 4N illustrates a cross-section view of the components taken along a plane that bisects both components. Coupling or mating of the components essentially includes a two-step and/or two movement process. Specifically, mating of the components involves a translation movement of the male component 404 relative to the female component 402 and a rotational movement of the male component 404 relative to the female component 402. The translation movement includes inserting the flange 423 of the male component's coupling member or stepped protrusion 422 within the coupling aperture or stepped recess 420. The translation movement may be along or diagonal to an axis of the plane bisecting the male and female components as shown by the arrow. The rotational movement includes rotating the male component 404 after the flange 423 is inserted within the coupling aperture or stepped recess 420 so that a top surface of the flange 423 is positioned adjacent a bottom surface (i.e., recessed portion 429) of the female component 402. The rotational movement of the male component 404 is about an axis that is orthogonal to the bisecting plane (i.e., an axis into the FIG) as shown by the rotational arrow. The aperture 426 and post 424 may couple as the male component 404 is pressed downward onto the female component 402 and an audible snap sound and tactile sensation may be produced.

The configuration of the stepped protrusion 422 and stepped recess 420 allows the male and female components, 404 and 402, to be coupled or mated with essentially a single translational movement. Stated differently, the translational movement of the male component 404 relative to the female component 402 may include a movement in a first direction (i.e., in the direction of the arrow) without a significant movement in an opposite direction since the flange 423 is inserted within the coupling aperture and then merely rotated into position within the coupling aperture. The term "significant movement" in describing the reverse movement means that some small reverse movement may occur, but it such movement is relatively minor compared to the movement of inserting the flange 423 within the stepped recess. Because the male and female components, 404 and 402, may be coupled via essentially a forward movement and little to no reverse or backward movement, the amount of slack needed in the lace, strap, or other tension member is greatly reduced. Stated differently, slack is not needed in the lace, strap, or tension member since the male component 404 does not travel beyond the female component 402 and then retract relative thereto. As such, the amount of lace, strap, or other tension member used may be reduced and additional tightening of the brace is not needed to wind lace and/or remove unneeded slack.

The configuration of the stepped protrusion 422 and stepped recess 420 also allows the flange 423 to be inserted within the coupling aperture at relatively low angles, such as at less than 45°, less than 30°, and in some embodiments less than 25° or 20°. Because the flange 423 is insertable within the coupling aperture at relatively low angles, a distal tip of the flange 423 need not break a plane of the bottom surface 433 of female component 402. In such embodiments, the distal tip of flange 423 need not poke or contact the brace which is positioned below and coupled with the female component 402 and thus, need not poke or job the user's limb around which the brace is positioned. As such, the user may couple the male and female components, 404 and 402, and close the brace about a limb without poking or jabbing the limb.

Further, as described above, the coupling or mating process illustrated in FIG. 4N may be performed with a single hand. In some embodiments, the proximal end of the male component may be coupled with a tension member (i.e., lace, strap, and the like) that is configured to tension the male and female components upon operation of a reel assembly or other tightening mechanism. In such embodiments, the reel assembly or other tightening mechanism may be operated to tension the tension member and the male and female components and thereby tighten the brace/article about a limb of an individual. The brace may be positioned about the limb, and a first side of the brace may be folded over the limb. The male component, which is coupled with the first side of the brace, maybe coupled with the female component, which is coupled with a second side of the brace, to close the brace about the limb. In some embodiments, the male and female components may be locked in the coupled engagement to prevent uncoupling of the male and female components.

In other embodiments, the male and female components may be uncoupled in a reverse manner to that describe above for FIG. 4N. Specifically, tension may be released tension in the tension member via a reel assembly or other tightening mechanism. The male component may then be uncoupled from the female component to allow the article to be removed from the limb by counter-rotating the male component relative to the female component and removing the flange from the coupling aperture. As described previously, the male component is not decouplable, releasable, or otherwise removable from the female component while some amount of tension remains in the tension member.

As can be readily understood, when the mated components are placed in tension the stepped protrusion and stepped recess prevent the male and female components from uncoupling. Uncoupling of the components occurs in a manner opposite of that described to couple the components. Specifically, the male component is lifted vertically to rotate the male component relative to the female component. The stepped protrusion of the male component is then withdrawn from the stepped recess of the female component. Because the male and female components are uncoupled in this manner, it is difficult to uncouple the components while they are in tension. Accordingly, a user must usually untension the lace winding system in order to uncouple the two components, which reduces or prevents lace shortening and over storage of the lace within the tightening mechanism as described herein.

Referring to FIGS. 5A-5E, illustrated is another embodiment of a detachable guide that shows the coupling process. Specifically, a male component 504 is coupled with a female component 502 by inserting a stepped protrusion 522 of male component 504 into a stepped recess 520 of female component 502. After the stepped protrusion 522 is inserted into the stepped recess 520, the rear portion of the male component is pressed downward so that the stepped protrusion 522 rotates within the stepped recess 520 and the snap mechanism 526 of male component 504 is forced over a post 524 of female component 502.

Figure 5A:
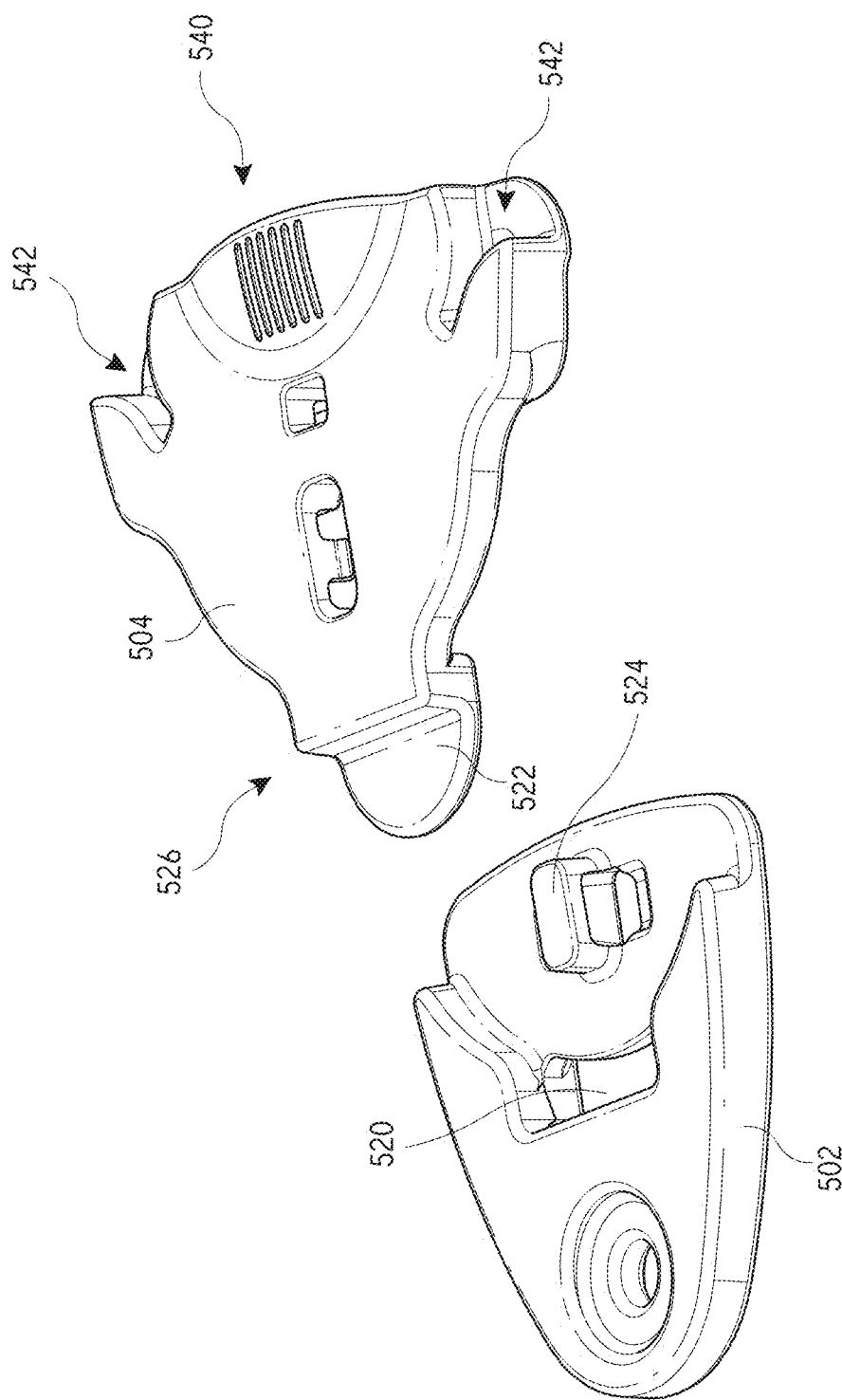
Figure 5C:
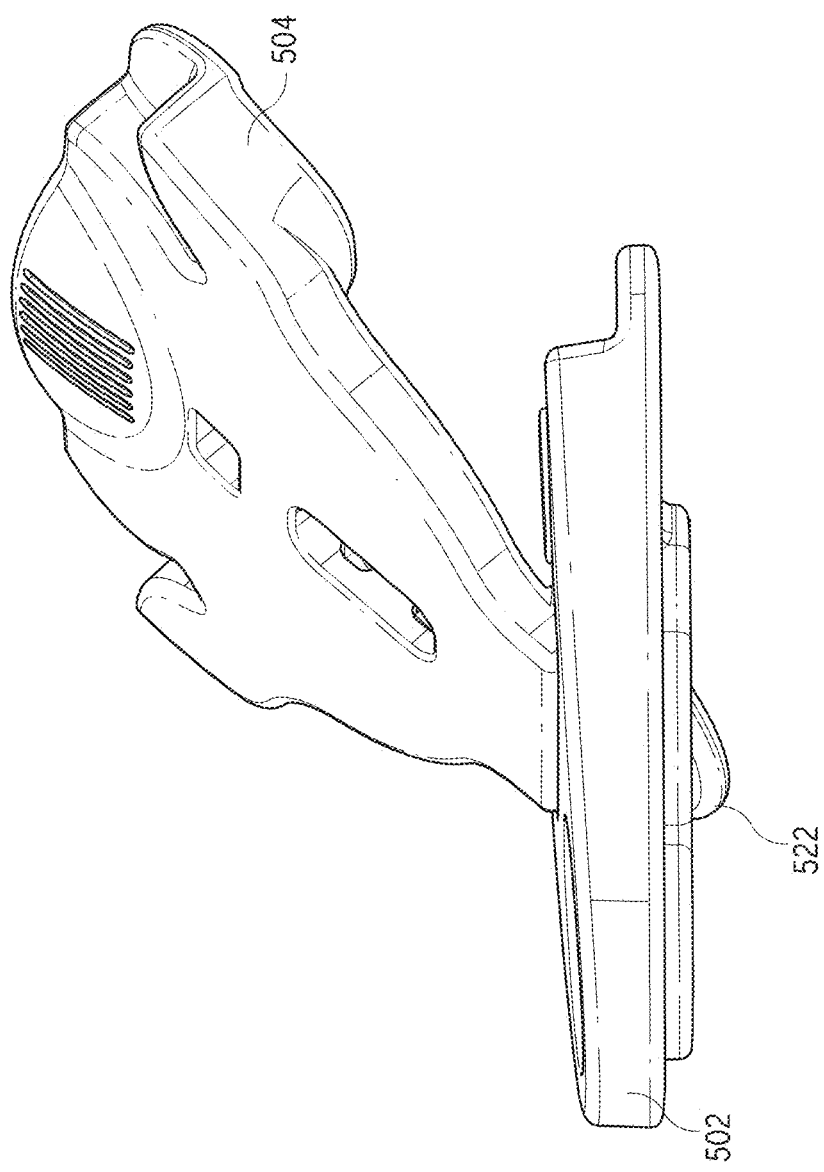
Figure 5D:
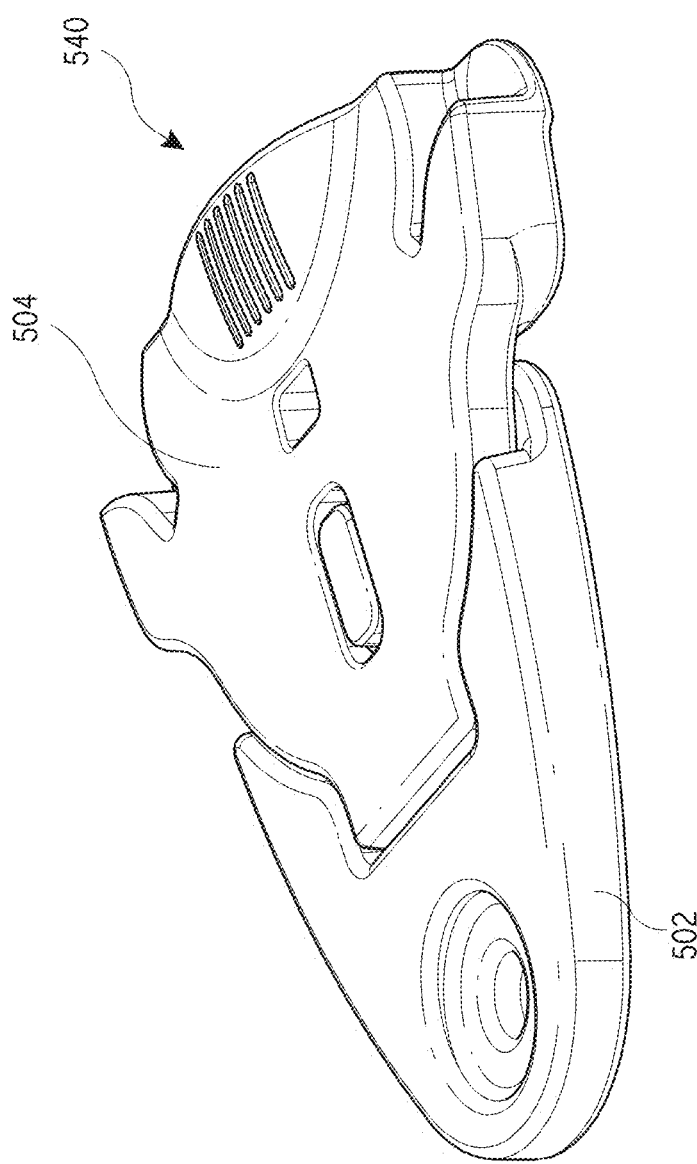
Figure 5E:
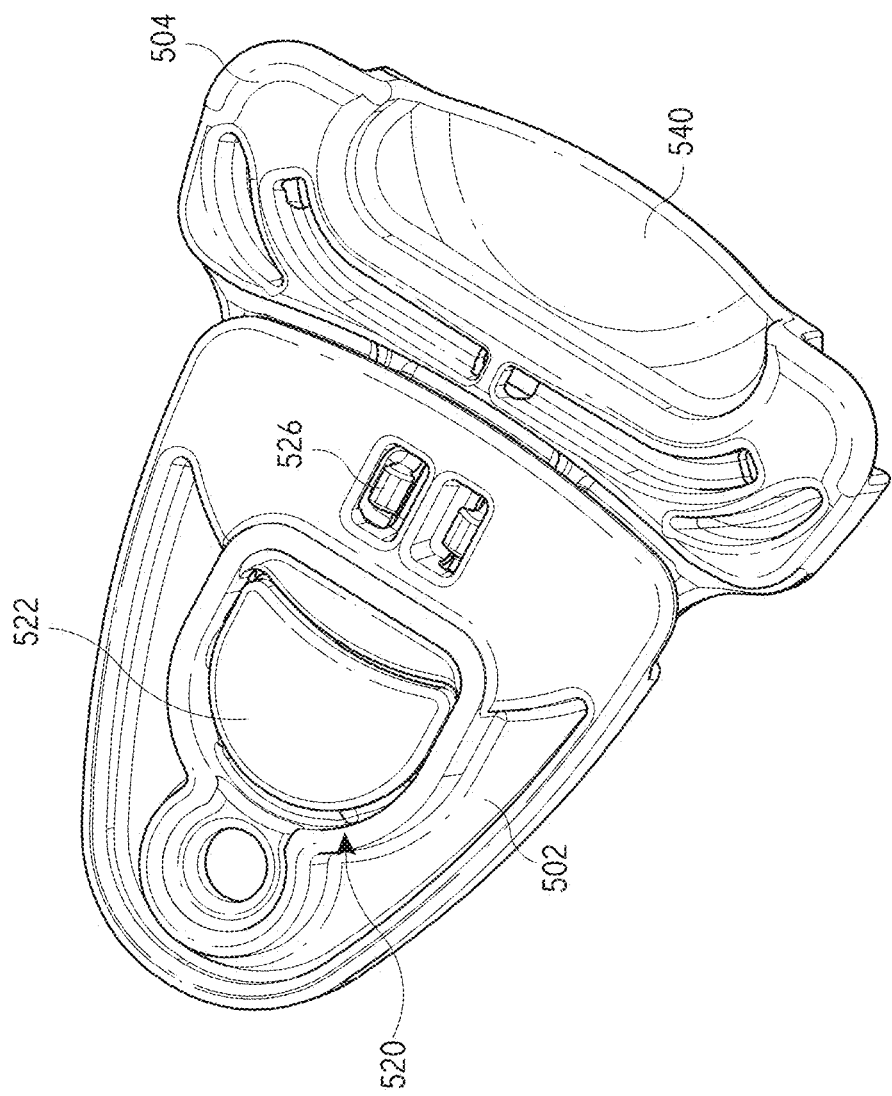

The proximal end of male component 504 may include a raised portion or arcuate recess 540 that facilitates in coupling and uncoupling of the components by allowing a user to place one or more fingers under the raised portion 540 and grasp a bottom surface of the male component 504. The user may position a thumb on the upper surface of the male component and a finger or fingers under the raised portion 540 and thereby grasp the male component with the thumb and fingers. In this manner, the user may easily couple and uncouple the two components. FIG. 5D shows the low profile of the detachable guide when the components are coupled. FIG. 5E shows a bottom perspective view of the coupled components and shows the stepped protrusion 522 mated with the correspondingly shaped stepped recess 520.

In some embodiments, the male component and female components described herein may include magnets or other features that facilitate in coupling the two components. For example, the stepped protrusion may include a magnet and the stepped recess may include a magnet to allow the stepped protrusion to "self-find" the stepped recess. Stated differently, the magnets may attract the stepped protrusion toward the coupled position within the stepped recess and/or guide the stepped protrusion toward the stepped recess. Such embodiments may make coupling the components with a single hand even easier. In another embodiment, adjacent stepped protrusions on a brace may have magnets that are oppositely polarized. Similarly, adjacent stepped recesses may also have magnets that are oppositely polarized. In such embodiments, cross connecting of male and female components, or in other words wrongful connecting of male and female components, is reduced since male and female components having magnets with the same polarization will be repelled.

Figure 6A:
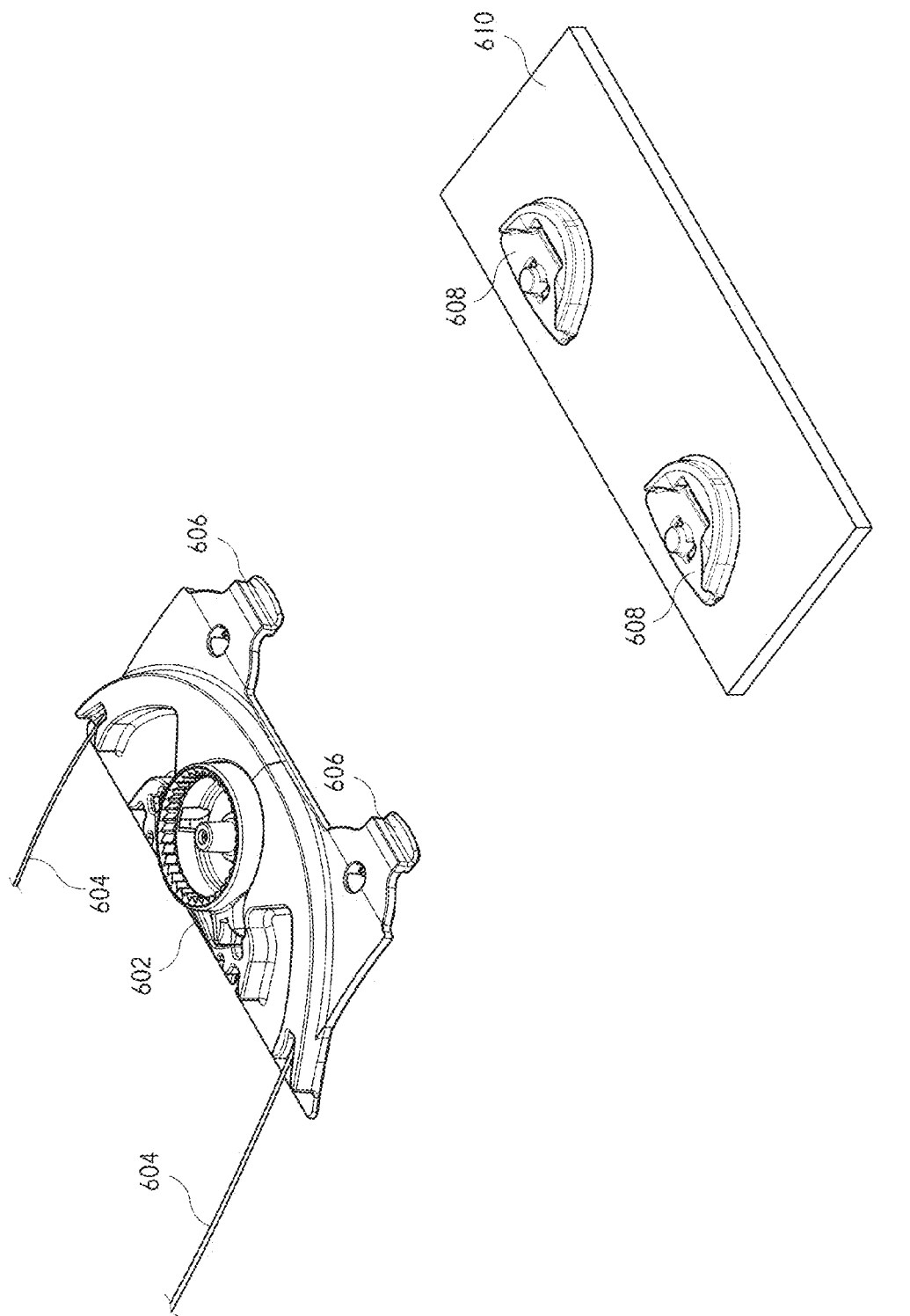
FIGS. 6A-6E illustrate various embodiments of closure panels that may be used to provide gross or macro adjustment of an article, such as a brace.

Referring to FIG. 6A, illustrated is an embodiment of a guide panel 602 having a plurality of male components and/or stepped protrusions 606 on a front edge of the guide panel that may be inserted into corresponding female components and/or stepped recesses 608 on an opposite surface 610 of the brace. The guide panel 602 includes straps or lace 604 that are coupled with a rear edge of the panel 602 and that are attached to the brace. In some embodiments, the guide panel 602 may be integrally formed with the brace so as not to include straps and/or stiffeners. The guide panel 602 may also include a tightening mechanism or reel assembly that allows the brace to be tightened when the male and female components, 606 and 608, are coupled together. The female components or stepped recesses 608 may be integrally formed with the opposite surface 610 of the brace or attached via stitching, adhesive bonding, riveting, heat welding, RF welding, injection molding, and the like. The guide panel 602 allows the user to grasp one side of the brace with a single hand (or both hands if desired), wrap the brace around the body, couple the male and female components, 606 and 608, and tension the tension member via a reel assembly or other tightening mechanism.

Figures 6C, 6D:
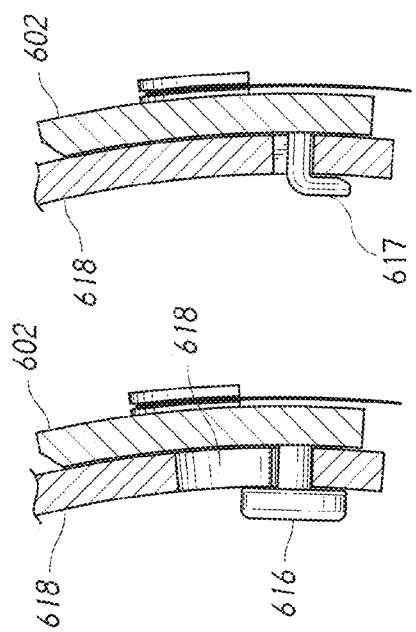
Figure 6B:
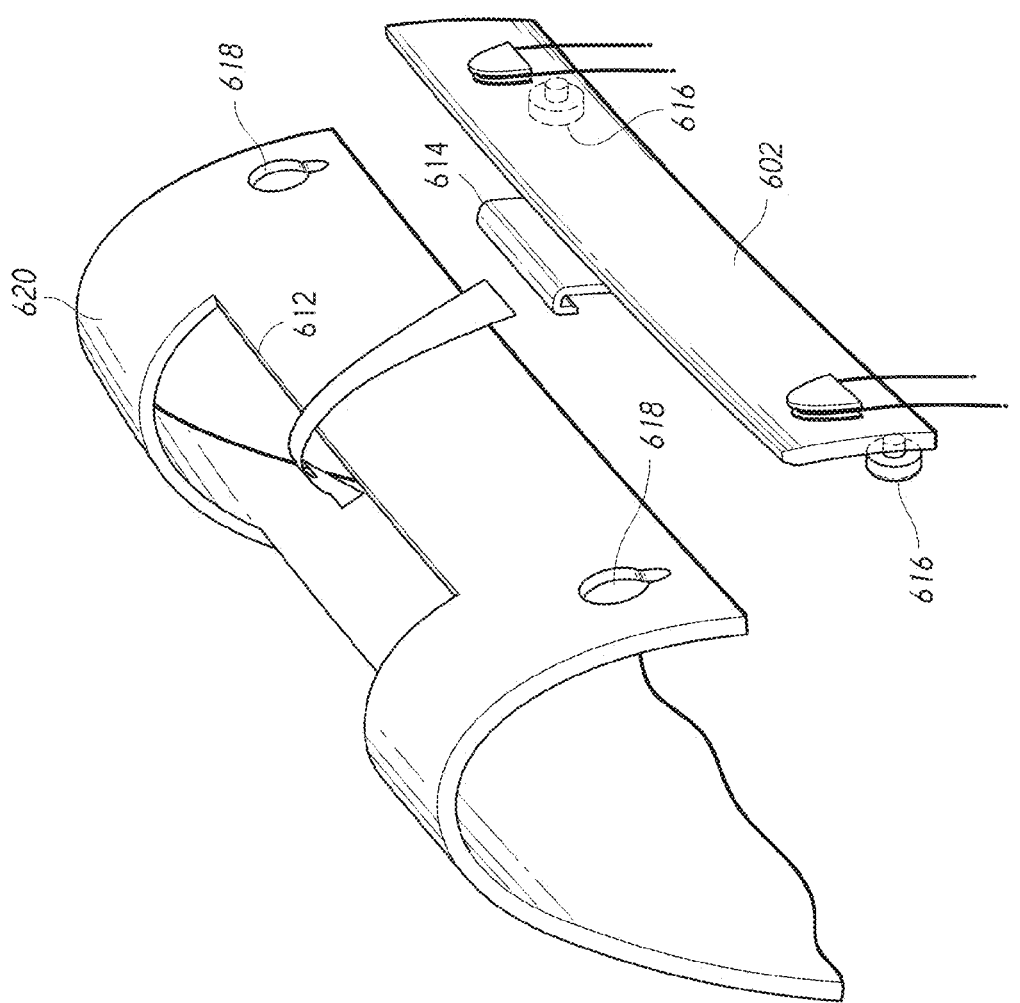

FIGS. 6B-D illustrate another embodiment of a guide panel 612 having stepped protrusions or hooks 616 that may be inserted within apertures 618. The apertures 618 may have a wide top portion that allows the hooks 616 to be inserted into the aperture and a narrow bottom portion into which the hooks may be slid, which prevents withdrawal of the hooks 616. The panel 612 may also include a hooked portion 614 that hooks onto a lip 612 of the brace. FIG. 6C illustrates a side cross sectional view of the hooks 616 and aperture 618. FIG. 6D illustrates another embodiment of a hook 617 that may be positioned within an aperture to couple opposing sides of a brace.

Figure 6E:
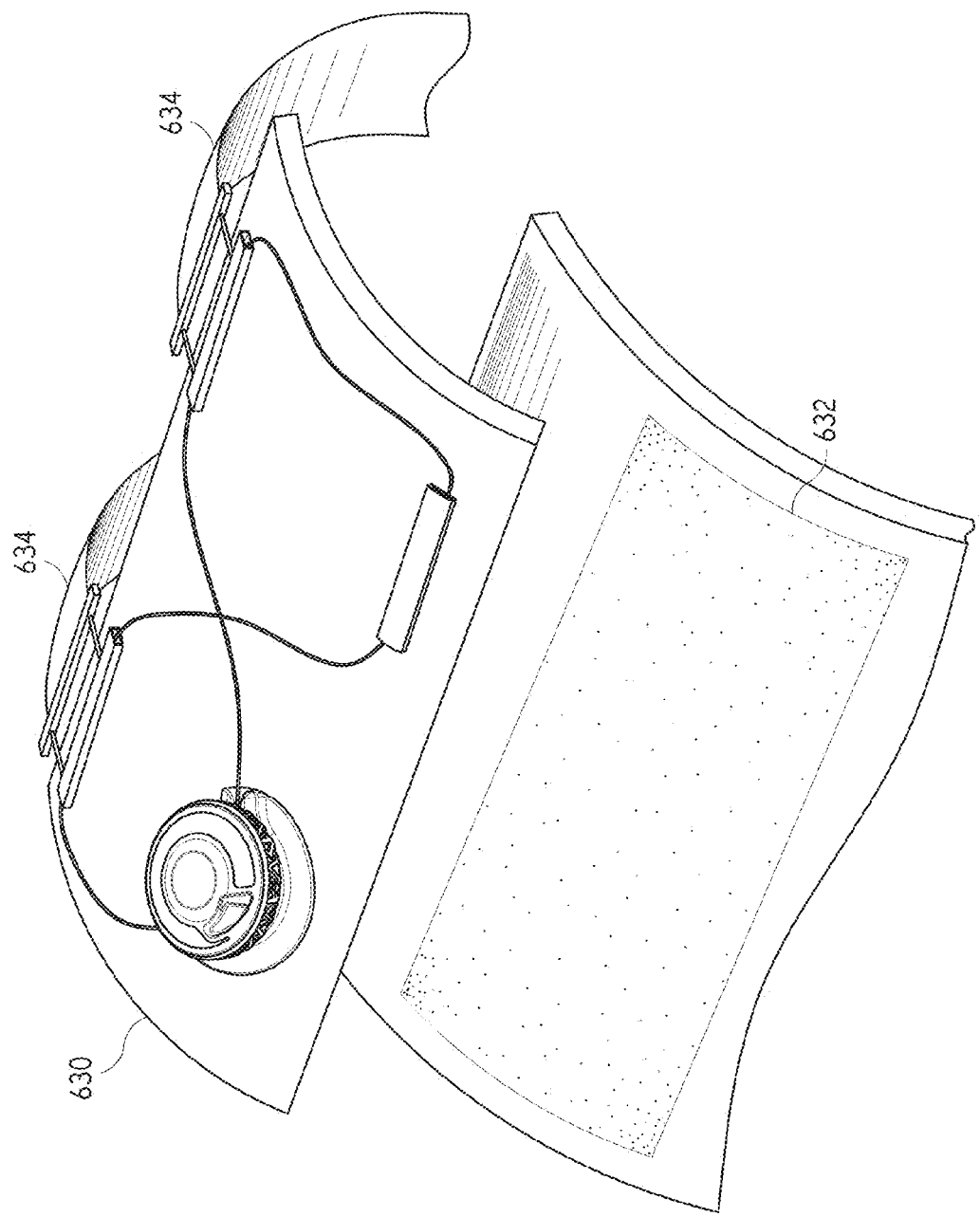

FIG. 6E illustrates another embodiment of a guide panel 630 that may be used to couple and uncouple opposing edges of a brace. The guide panel 630 includes Velcro® components on an undersurface that couple with corresponding Velcro® 632 positioned on a top surface of an opposite edge of the brace. Straps or laces 634 may be coupled with the guide panel 630 to allow the brace to be tightened via a tightening mechanism or reel assembly and a lace as described herein.

Figure 6F:
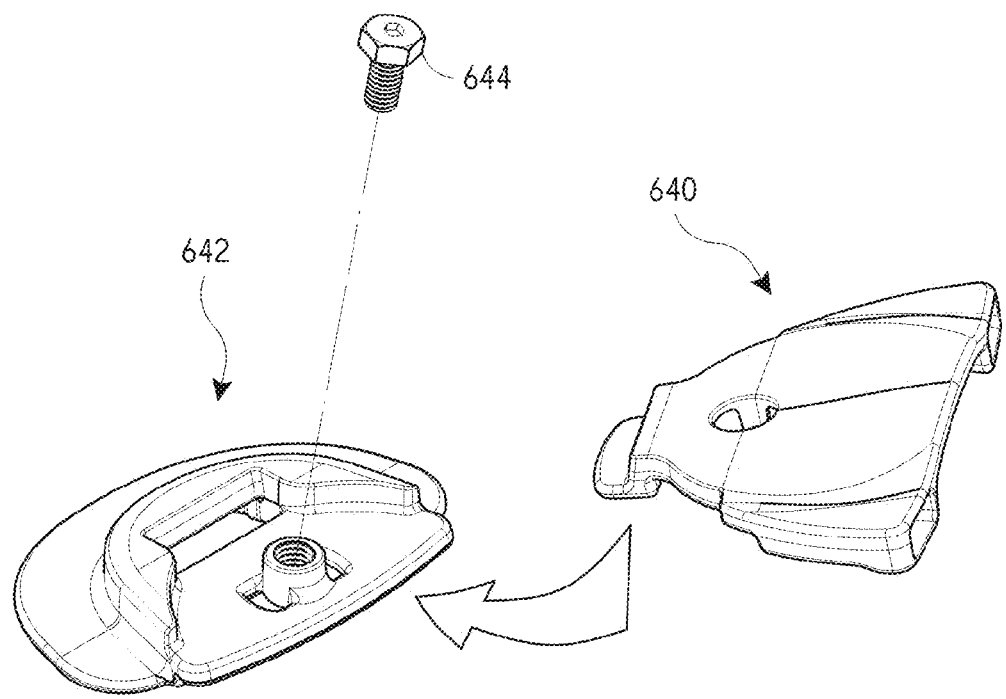
FIGS. 6F-6H illustrate various view of a lock mechanism that may be used to lock the male and female components of a closure device in a coupled engagement.
Figure 6G:
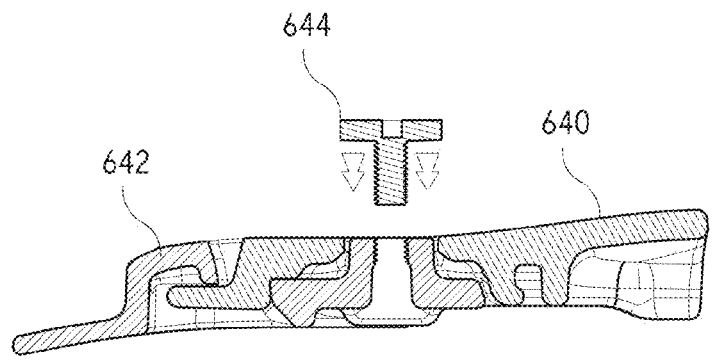
Figure 6H:
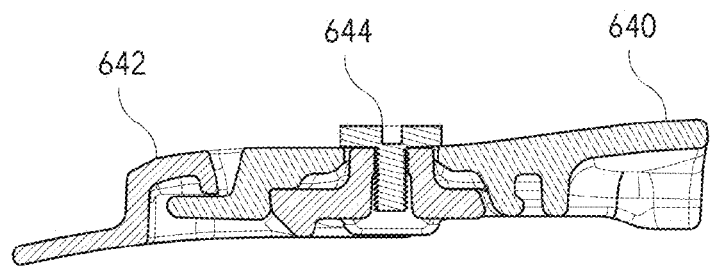
Figure 61:
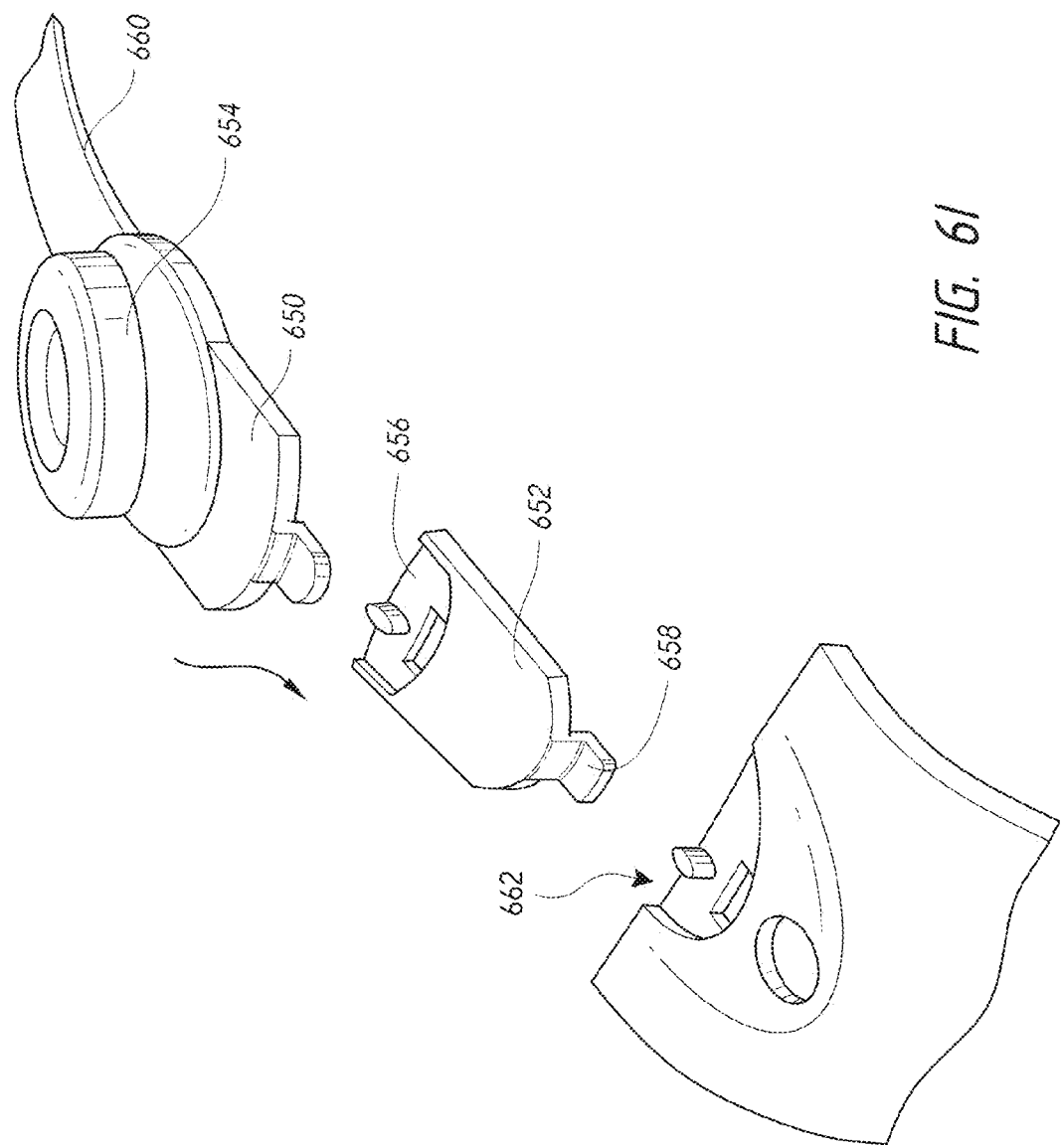

FIG. 6F-H illustrates a lock mechanism 644 (e.g., bolt and threaded boss) that may be used to lock the male component 640 within the female component 642. The lock mechanism 644 may be detachable from the male and female component and may be inserted into a threaded boss, aperture, or other feature of the coupled components to lock the components in the coupled configuration. In some embodiments, removal of the lock mechanism 644 may require a "key" or other device. The lock mechanism 644 may be useful when it is desired to limit or prevent removal of the brace. For example, a doctor or physician may place the brace over a body part and lock the coupled male and female components, 640 and 642, in place to prevent a patient from removing the brace. The patient may be able to tighten or loosen the brace via a reel assembly or other tightening mechanism, but would otherwise be unable to remove the brace. Upon sufficient recovery or therapy, the doctor could remove the lock mechanism 644 to allow the brace to be fully removed. In other embodiments, a range of lace motion for tightening and/or loosening of the lace could be provided to allow the patient to finely adjust the fit of the brace about the limb.

In some embodiments, the female component may have an arcuate configuration that corresponds to a shape of the brace or other article. In such embodiments, the male component may have a generally planar configuration. Tensioning or tightening of the male and female components (e.g., via lace and a reel assembly) may cause the male component to rotate into an increased engagement with the female component. For example, the rear surface of the tab (see 421 of FIG. 4E) may be pulled into increased engagement or contact with the distal surface of the lip of the coupling aperture, thereby increasing the engagement of the male and female components. In this manner, the locking engagement of the male and female components may be increased as the components are tensioned. In another embodiment, the recessed portion of the stepped recess may have an undercut region that the stepped protrusion's flange can rotate into as shown in FIGS. 6G and 6H. This may further increase the engagement of the two components.

FIG. 6I illustrates a modular component or link 652 that may be used as an extension piece for the male component 650. The modular component 652 includes a stepped recess 656 into which the stepped protrusion of the male component 650 is inserted, and also includes a stepped protrusion 658 that may be inserted into a stepped recess of another modular component or of a female component 662. A reel assembly or tightening mechanism 654 and lace 660 may be coupled with the male component 650 as described herein. Multiple modular components or links 652 may be snapped together to provide gross length adjustment, or to allow the brace to be fit to multiple different patient sizes.

FIG. 7 illustrates a brace 704 having a female component 702 that is integrated into the brace, such as by molding the female component 702 into the brace 704. In other embodiments, the female component 702 may be welded (e.g., sonic welded, radio frequency welded, heat welded, and the like), injection molded, riveted, and the like into brace 704, attached using adhesives, and the like. Although not shown, on an opposite surface 706, male components may be attached or integrally connected with brace 704 in a similar manner. Various straps (not shown), panels (not shown), and the like may couple the male component (not shown) with the opposite surface 706 of brace 704.

FIGS. 8A-8D illustrate various views of one embodiment of a female component 802 that includes an aperture 804 that allows the female component to be snapped, riveted, or bolted to a surface of a brace. The female component 802 may include the various features described herein, such as a stepped protrusion, a grooved post, and the like. Further, although not shown, in some embodiments, the female components described herein may be coupled with a tightening mechanism or reel assembly.

FIGS. 9A-9D illustrate various views of another embodiment of a female component 902 having a flange 904 that may be sewn into a surface of a brace. FIGS. 9A-9D illustrate the flange 904 extending from one side of female component 902. In other embodiments, the flange may extend partially or fully around the perimeter of female component 902. The female component 902 may include the various features described herein.

FIGS. 10A-10D illustrate various views of an embodiment of a male component 1004 having a d-ring or hook 1006 through which a strap may be inserted as described above. Male component 1004 also includes a grip surface 1008 that a user may grasp to facilitate insertion and removal of the stepped protrusion and stepped recess. FIG. 10C illustrates an enlarged view of the grip surface 1008, which may be a roughened surface that is molded into opposing edges of d-ring 1006. Male component 1004 may include the various feature described herein, such as the stepped protrusion, snap tabs or flanges, and the like.

FIGS. 11A-11E illustrate various views of another embodiment of a male component 1104 wherein lace (not shown) of a lacing system (not shown) are integrated or coupled with the male component 1104. Specifically, male component 1104 includes lace receiving portions or ports 1108 through which the lace is inserted. The lace receiving portions or ports 1108 are connected to guide slots or channels 1112 on an undersurface (or top surface) of male component 1104 that, in one embodiment, direct the laces to an opening 1110 on the top surface of male component 1104. A tightening mechanism or reel assembly (not shown) may be coupled with the top surface of male component 1104 so that the brace may be tightened by winding or operating the tightening mechanism/reel assembly to pull the lace through the lace receiving portions/ports 1108 and guide slots/channels 1112. In another embodiment, the guide slots/channels 1112 may be represent a single lumen through which the lace passes from one lace receiving portion/port 1108, through the male component 1104, and out the other lace receiving portion/port 1108. In such embodiment, the male component 1104 may include a single lace guide (i.e., the single lumen) having a smooth lace track that allows the lace to smoothly feed through the male component 1104.

In one embodiment, the single lumen lace guide (i.e., the combined lace guides 1112) may be constructed during a molding process by inserting a tooling (metal or other composition) through opening 1110 and into the lace track. A second tooling piece, or multiple tooling pieces, may be inserted in the opposite direction through guide tracks 1112 and into the lace track so as to mate or closely fit with the tooling inserted through opening 1110. This fit of the various tooling eliminates or greatly reduces the overflow of the injected material between the tooling parts. Conventional process that involve mating tooling only from an underside (or topside) of the piece often result in inconsistent mating of the tooling and flash or overflow between the tooling, which may create a relatively rough lace track that is difficult to feed lace through. The same process may be repeated at the lace receiving portions 1108 where the lace enters and exits the male component 1104 to provide a single smooth lace track through which the lace is inserted.

The male component 1104 also includes a raised portion 1106 that allows a user to position one or more fingers on an undersurface of male component 1104 and one or more fingers on a top surface of male component 1104 to grasp the male component 1104 and insert the stepped protrusion into the stepped recess or remove the stepped protrusion therefrom. The male component may also include the various other features described herein.

Figure 12:
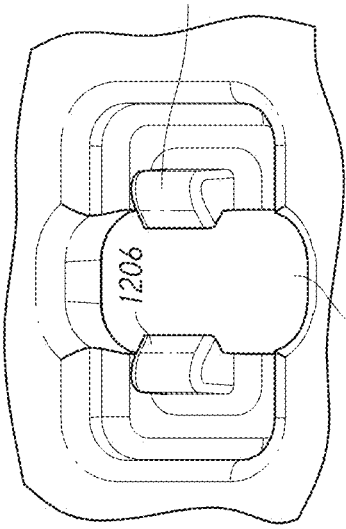
FIG. 12 illustrates an enlarged view of a pair of snap tabs of a male component of a closure device.
Figure 11D:
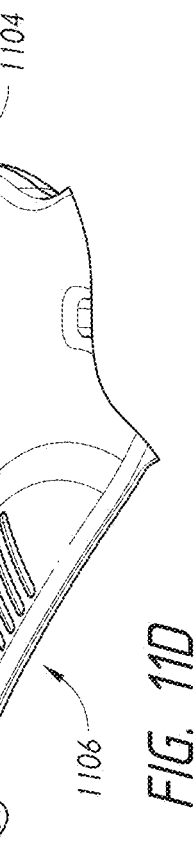
Figure 11E:
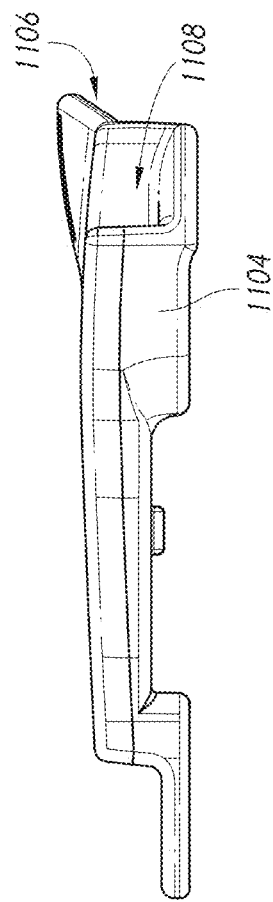

FIG. 12 illustrates an enlarged view of a pair of snap tabs 1202 according to one embodiment. The snap tabs 1202 are positioned on opposing sides of an aperture 1204 that is configured to receive a grooved post of a female component as described above. The snap tabs also include inward facing flanges or lips 1206 that are pressed over and around the grooved posts and that cause the snap tabs 1202 to snap into place to provide audible and tactile feedback as described herein.

Although not shown, in some embodiments when the male component is not coupled with the female component, the male component may be stowed on the brace to keep the male component free from catching onto surrounding objects. For example, the male component may couple with a strap, tightening mechanism or reel, or another object near to the component.

Figure 13A:
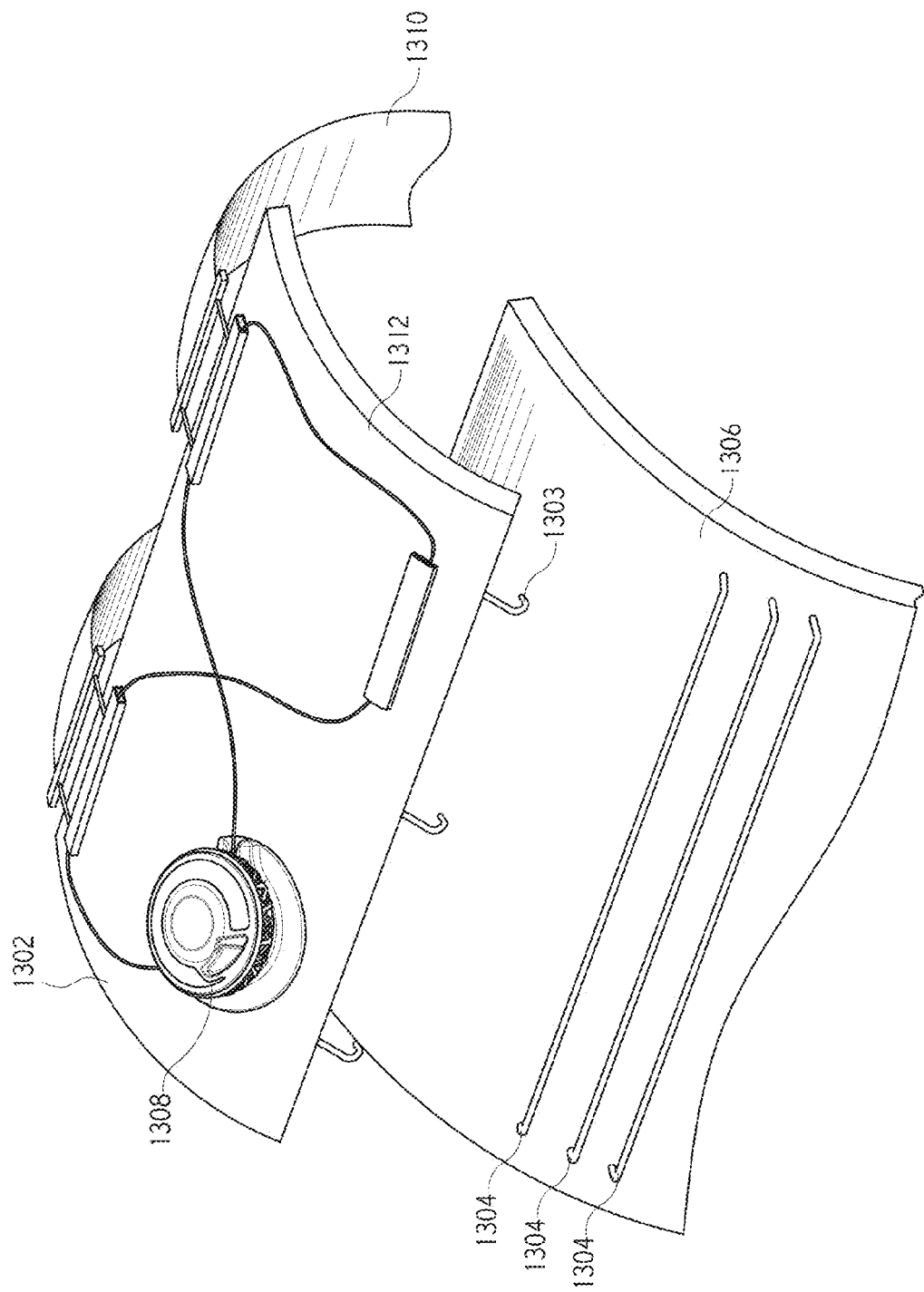
FIG. 13A illustrates a closure panel having hooked portions that engage with coupling bars positioned on an opposing side of an article.
Figure 13B:
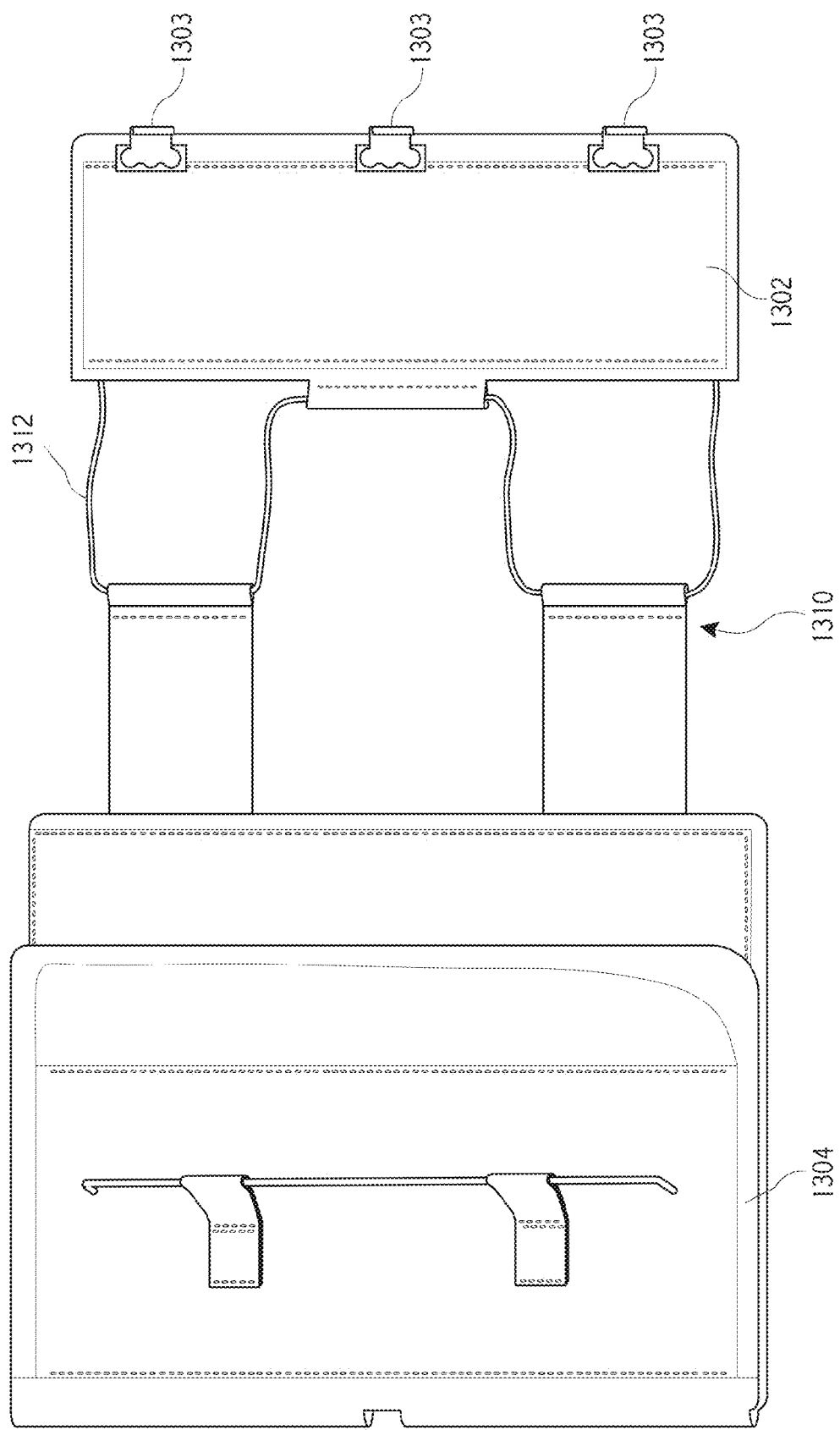
FIG. 13B illustrates a closure panel similar to the closure panel of FIG. 13A in an opened configuration.
Figure 13C:
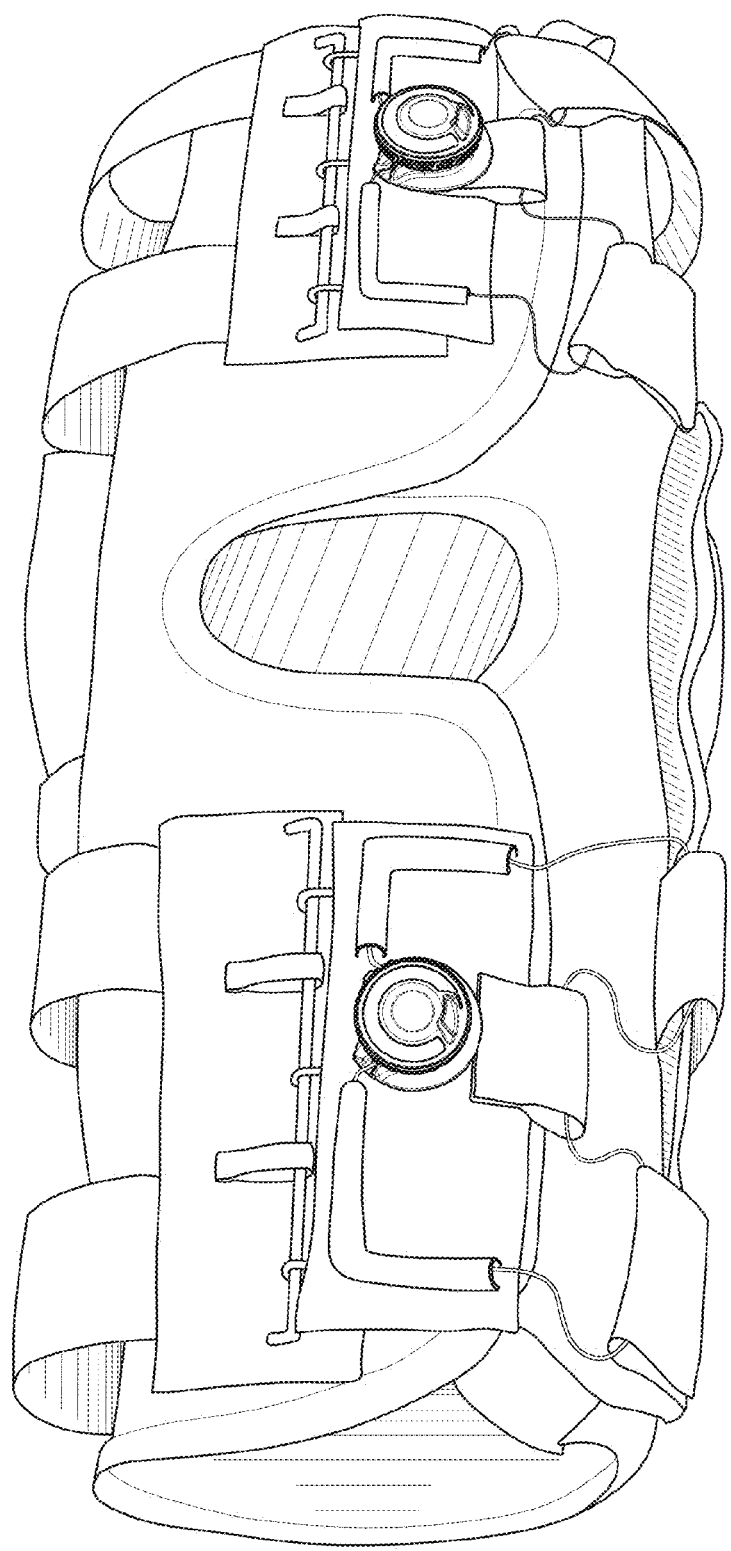
FIG. 13C illustrates a brace having a pair of closure panels that close a top and bottom portion of the brace about a limb.

FIGS. 13A-13C illustrate various views of another embodiment of a detachable device. The detachable device includes a panel 1302 having a plurality of hooks 1303 that attach to attachment bars or rods 1304 on an opposite surface 1306 of a brace. The attachment bars or rods 1304 are arranged in a ladder like or step configuration to allow the hooks 1303 and panel 1302 to be moved and tightened incrementally along the opposite surface 1306. The panel 1302 may thus be placed over the body and the hooks attached to one of the attachment bars for gross size adjustment. After gross adjustment, the brace may be tightened via a tightening mechanism or reel assembly 1308 and lacing system 1312. Additionally, the panel 1302 may be coupled with one or more straps 1310 that allow for additional adjustment of the brace. FIG. 13B shows the panel 1320 uncoupled from attachment bar 1304 in an open configuration while FIG. 13C shows two panels attached to attachment bars in a closed configuration.

Figure 14A:
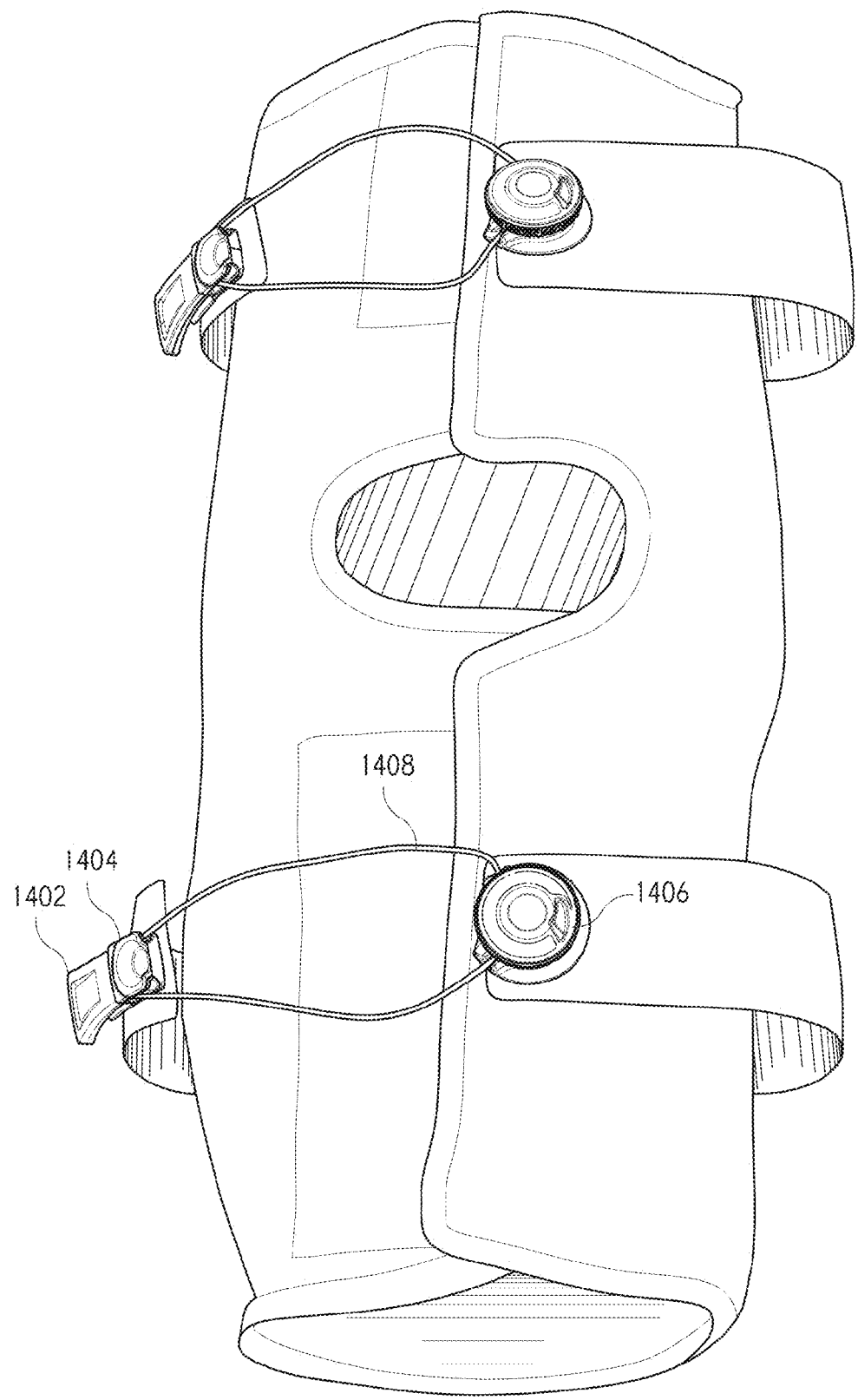
FIG. 14A-15 illustrate various embodiments of braces having closure devices that close the braces about a limb.
Figure 14B:
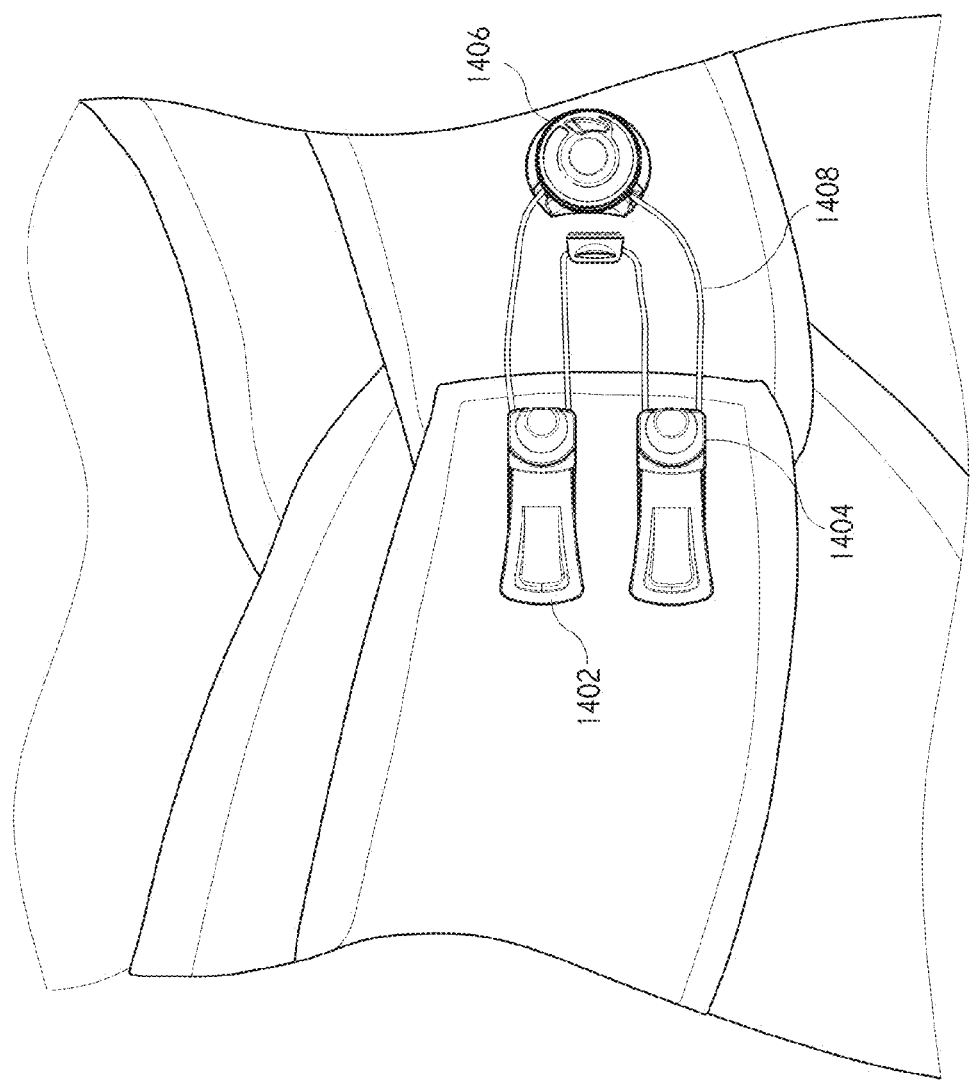

FIGS. 14A and 14B illustrate another embodiment of a detachable device that may be used to close braces or other devices. The detachable device includes a pull tab 1402 that is coupled with the lace 1408 and may act as a guide. The pull tab 1402 fits within a corresponding receptacle 1404 that includes a channel that receives an edge of the pull tab 1402. The pull tabs 1402 lie against the brace in a relatively flat configuration so as to avoid grabbing or catching objects near the brace. An opposite end of the lace 1408 may be coupled with a tightening mechanism or reel assembly 1406 to allow the lace to be tightened as described herein. In some embodiments, the pull tab 1402 may be stowed on the brace to keep the pull tab free from catching onto surrounding objects. For example, the pull tab 1402 may fit into a holding slot on a reel, strap, or other object.

Figure 15:
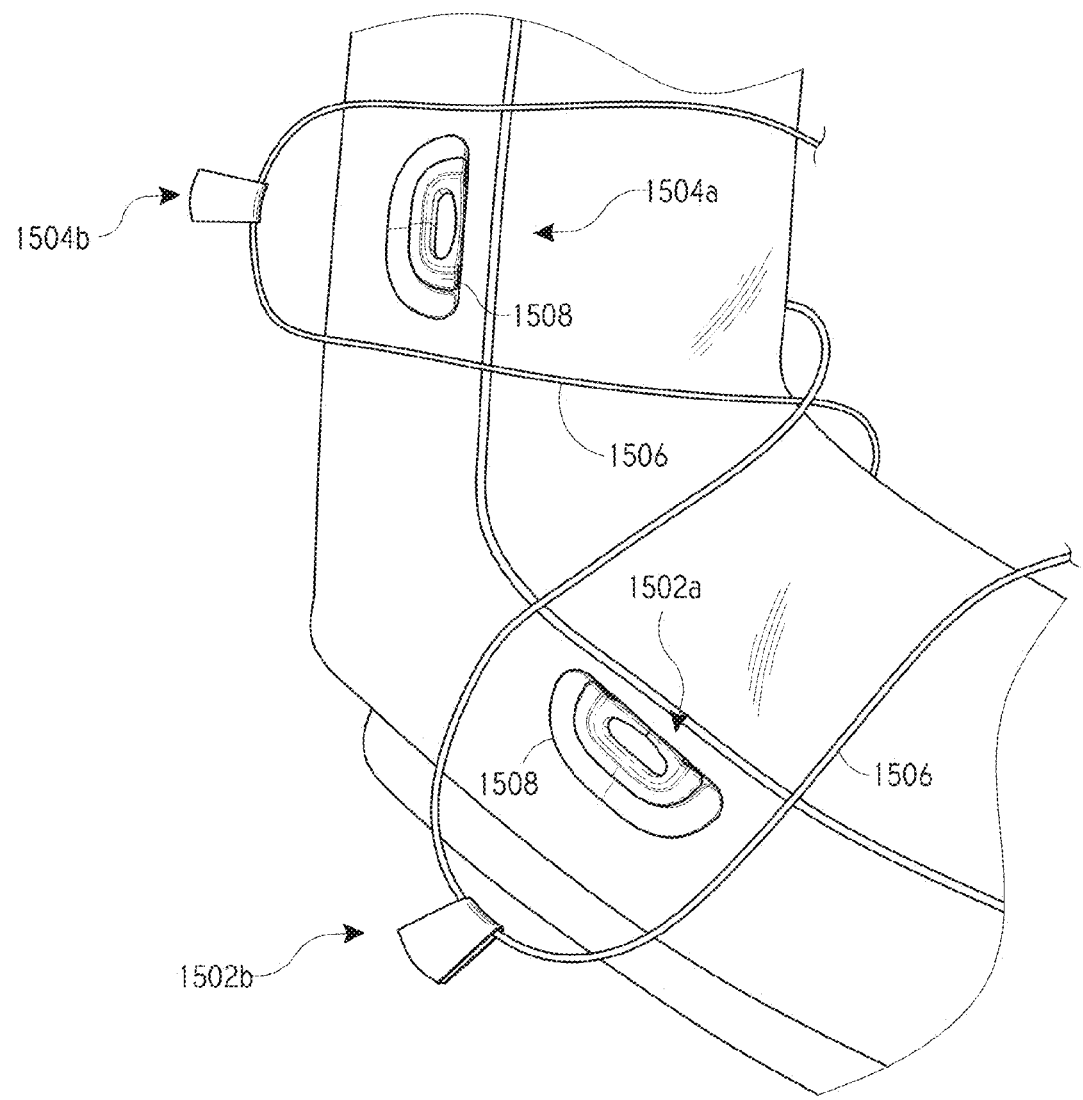

FIG. 15 illustrates another embodiment of a detachable device. The detachable device includes a pair of laces 1506 that may be removably placed within open ended guides 1508 and released therefrom to allow a brace or device to be opened and closed so that a user may don and doff the brace. When multiple open ended guides 1508 are used, each guide 1508 may be colored coordinated, or coordinated in some other way, with a corresponding lace to visually indicate how the laces should be threaded and thereby reduce cross coupling of the laces. For example a first guide 1502a and first pull tab 1502b may both be colored red to visually indicate the relationship of the first guide and pull tab, 1502a&b, while a second guide 1504a and second pull tab 1504b are both colored blue to visually indicate their relationship. In another embodiment, corresponding pairs may be designed so that a pull tab or connector is only able to couple with a corresponding guide or receptacle. For example, the pull tabs or connectors could have a circular, semi-circular, square, and the like configuration that only couples with a correspondingly shaped guide or receptacle.

Figure 16:
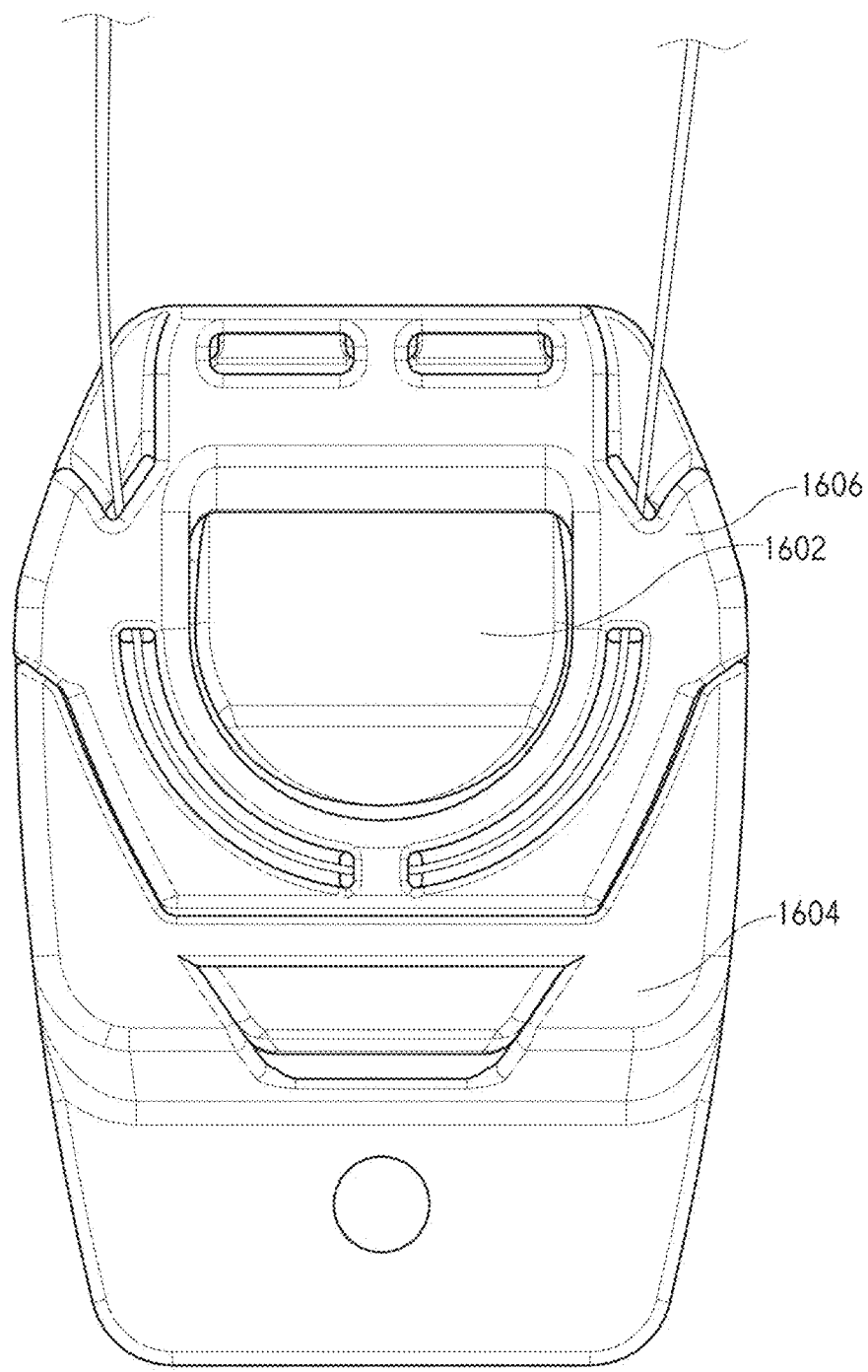
FIG. 16 illustrates a bottom view of a coupled male and female components of a closure device.
Figure 17A:
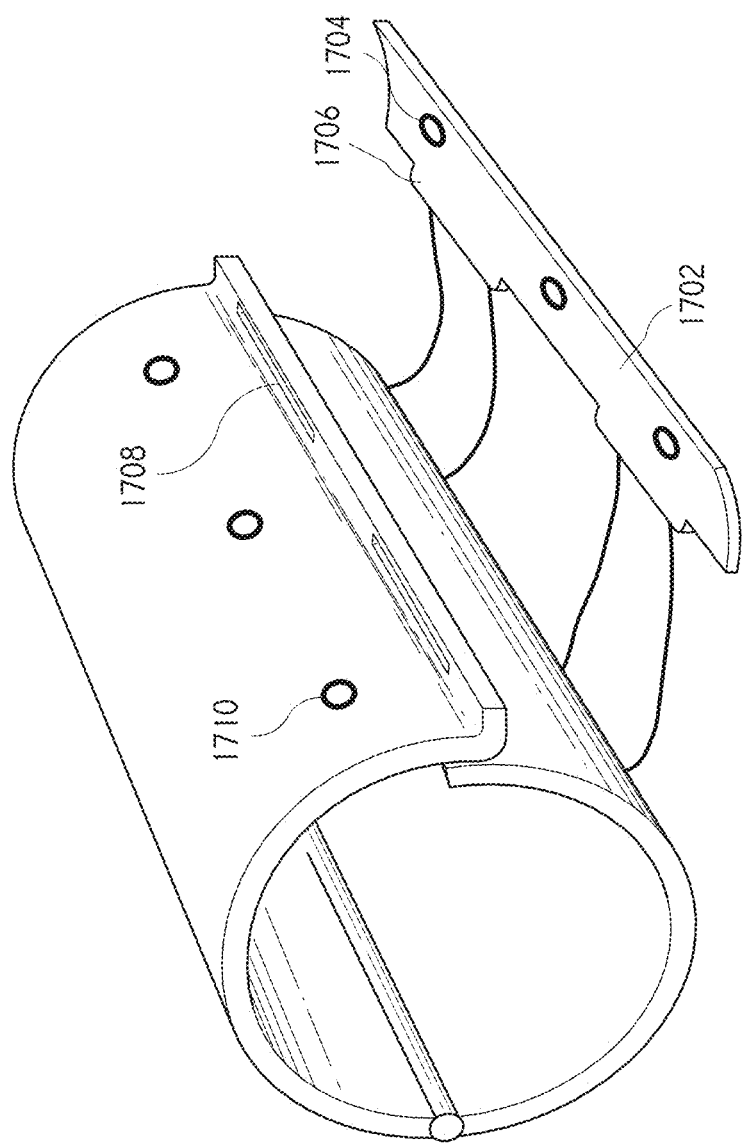
FIGS. 17A-18 illustrates other embodiments of closure devices that may be used to close an article, such as a brace.
Figure 17B:
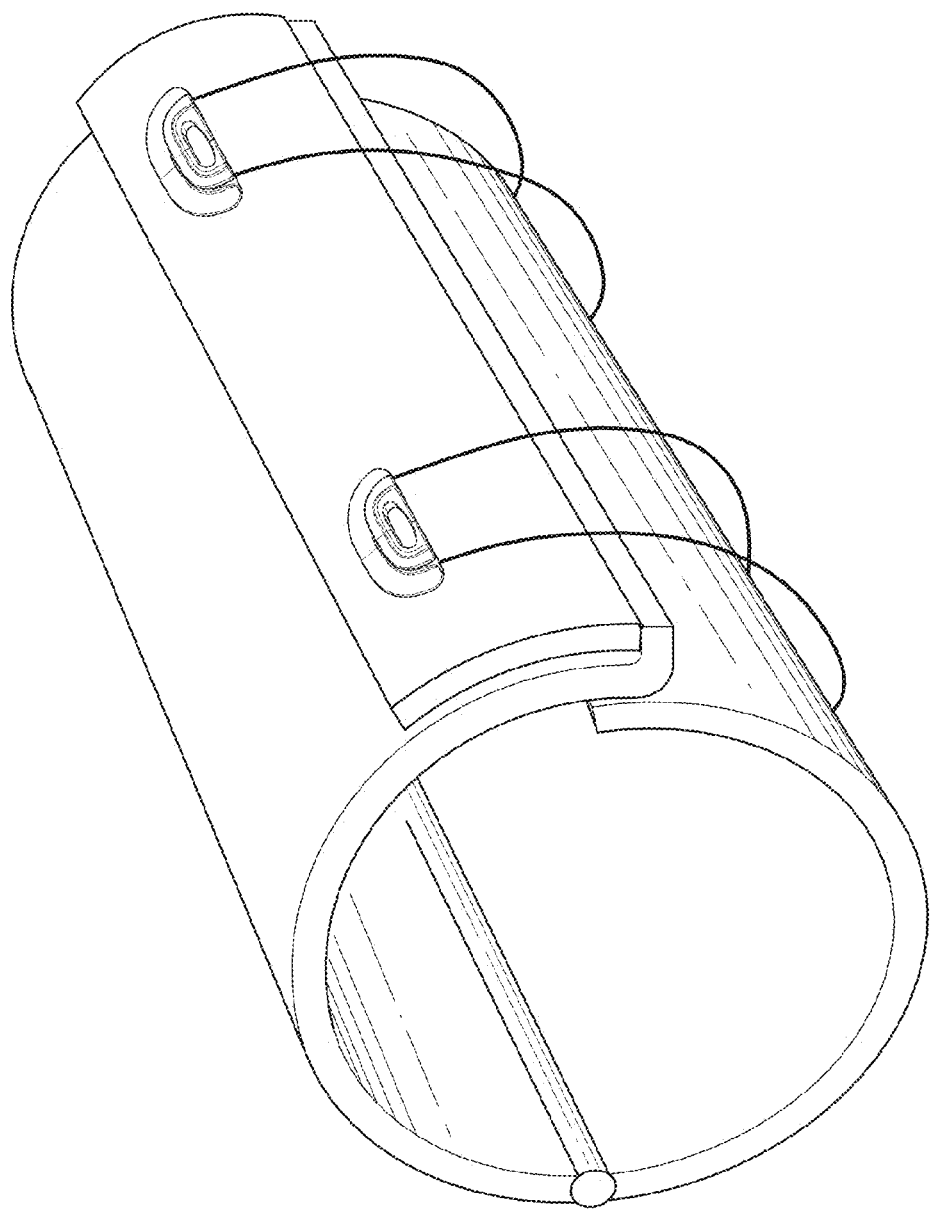

FIG. 16 illustrates another detachable device having a male component 1604 and a female component 1606 that couple together. A button 1602 may be used to decouple the male and female components, 1604 and 1606, such as by displacing a stepped protrusion or post from within a corresponding receptacle. FIGS. 17A and 17B illustrate yet another detachable device having a panel 1702 that includes a first set of tabs 1704 that couple with a post 1710 positioned on an opposite surface of the brace. The panel 1702 also includes a second set of tabs 1706 that fit within corresponding apertures 1708 positioned on the opposite surface of the brace. In some embodiments, tabs 1704 and post or aperture 1710 may be magnetic so that the tabs and posts magnetically attach.

Figure 18:
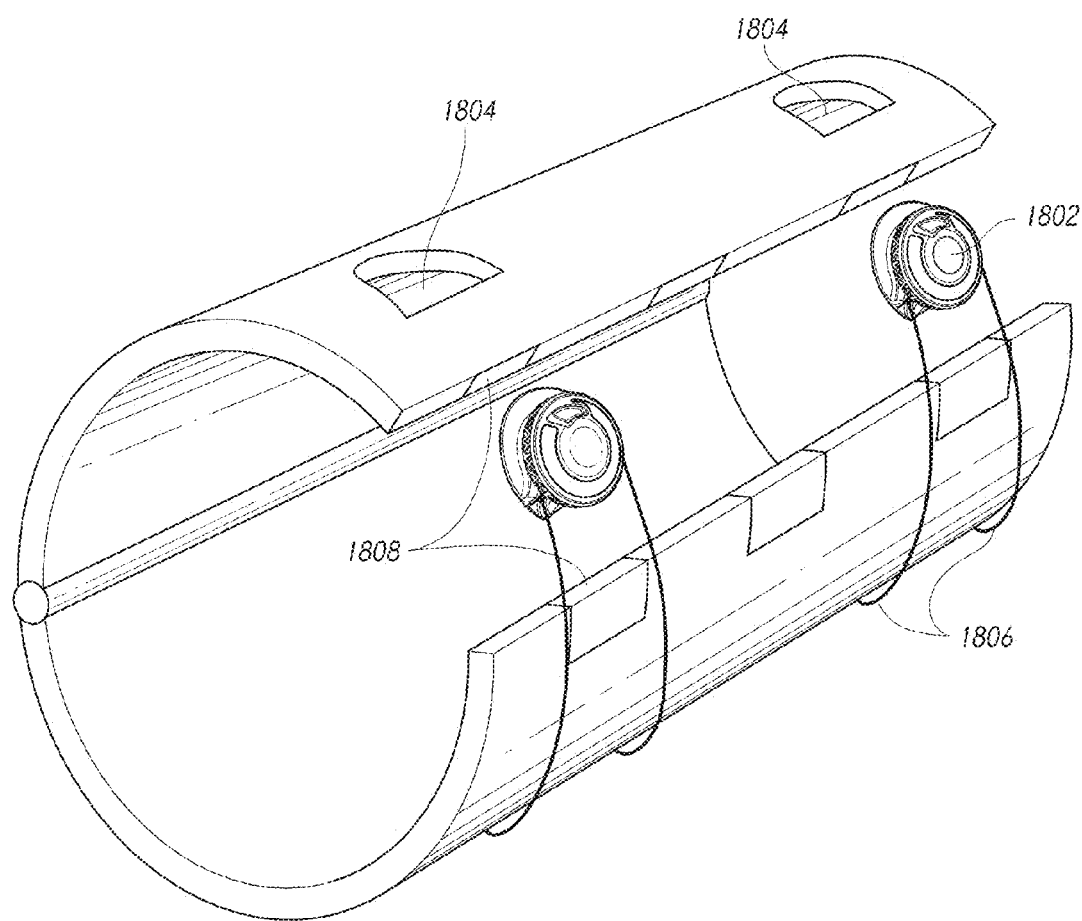

FIG. 18 illustrates yet another detachable device for a brace. The detachable device includes a male component and reel assembly 1802 that may be inserted over a body part and into a female receptacle 1804 as described herein to attach the brace about the body part. Reel assembly 1802 may be used to tighten lace 1806 about the body part after the male component is inserted into the female receptacle 1804. In some embodiments, opposing inner surfaces of the brace 1808 may include oppositely polarized magnets so that the inner surfaces may be attached.

In other detachable device embodiments, a reel assembly may climb or ratchet up a perforated strap to tighten a brace. For example, the strap may have a plurality of apertures spaced at even intervals. As the reel or other mechanism is operated, the reel assembly may ratchet up the apertures or pull the strap through the reel assembly. In some embodiments, guides may be positioned in the various apertures or ratchet up the aperture as the mechanism is tightened.

Figure 19:
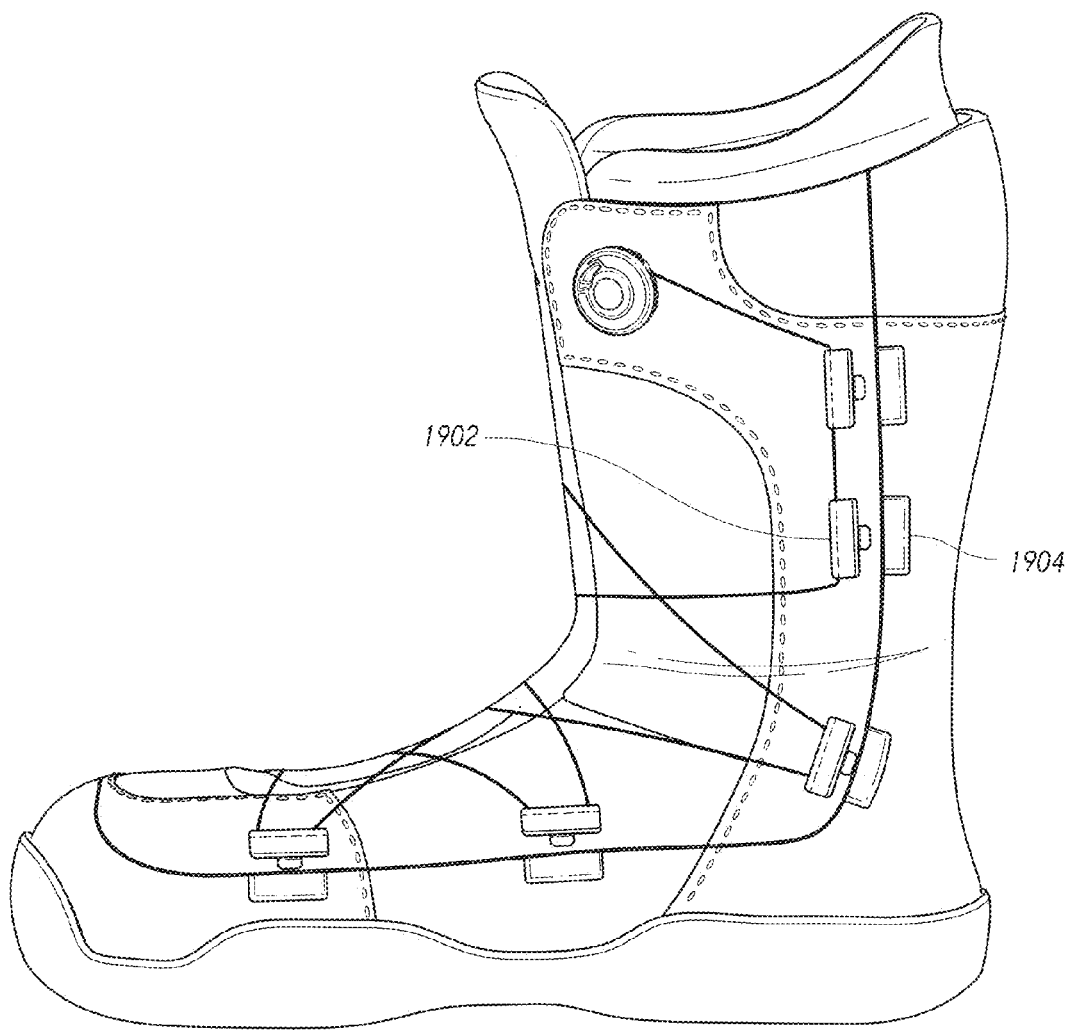
FIGS. 19-20 illustrate the closure device being used to close other articles, such as a boot or sandal.
Figure 20:
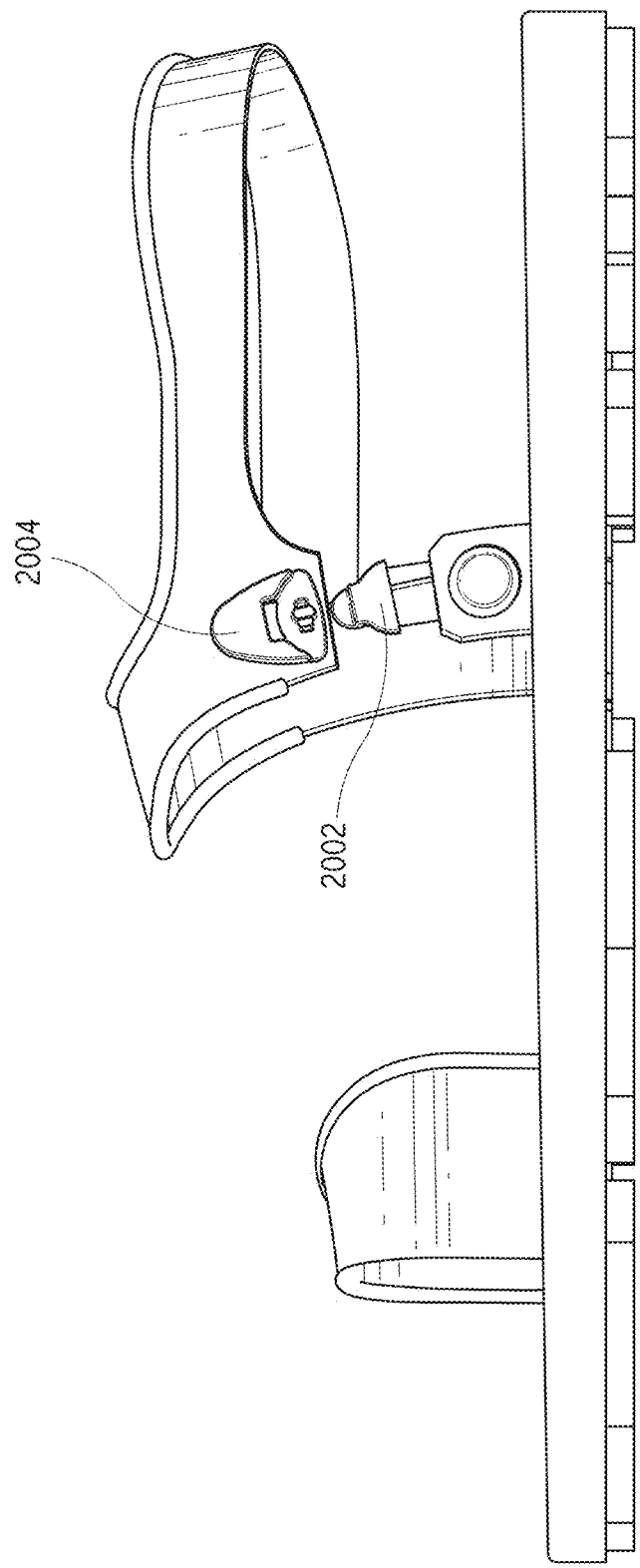

FIGS. 19 and 20 illustrate the detachable device described herein being used for purposes other than to close a brace. For example, FIG. 19 illustrates a detachable device having male components 1902 and female components 1904 being used to close a boot, which may be an orthotic boot, snowboard boot, work boot, outdoor boot, and the like. FIG. 20 illustrates a detachable device having male components 2002 and female components 2004 being used to close a sandal or shoe. It should be realized that the detachable devices described herein may be used for various other purposes and are not limited to the disclosure herein.

Figure 21:
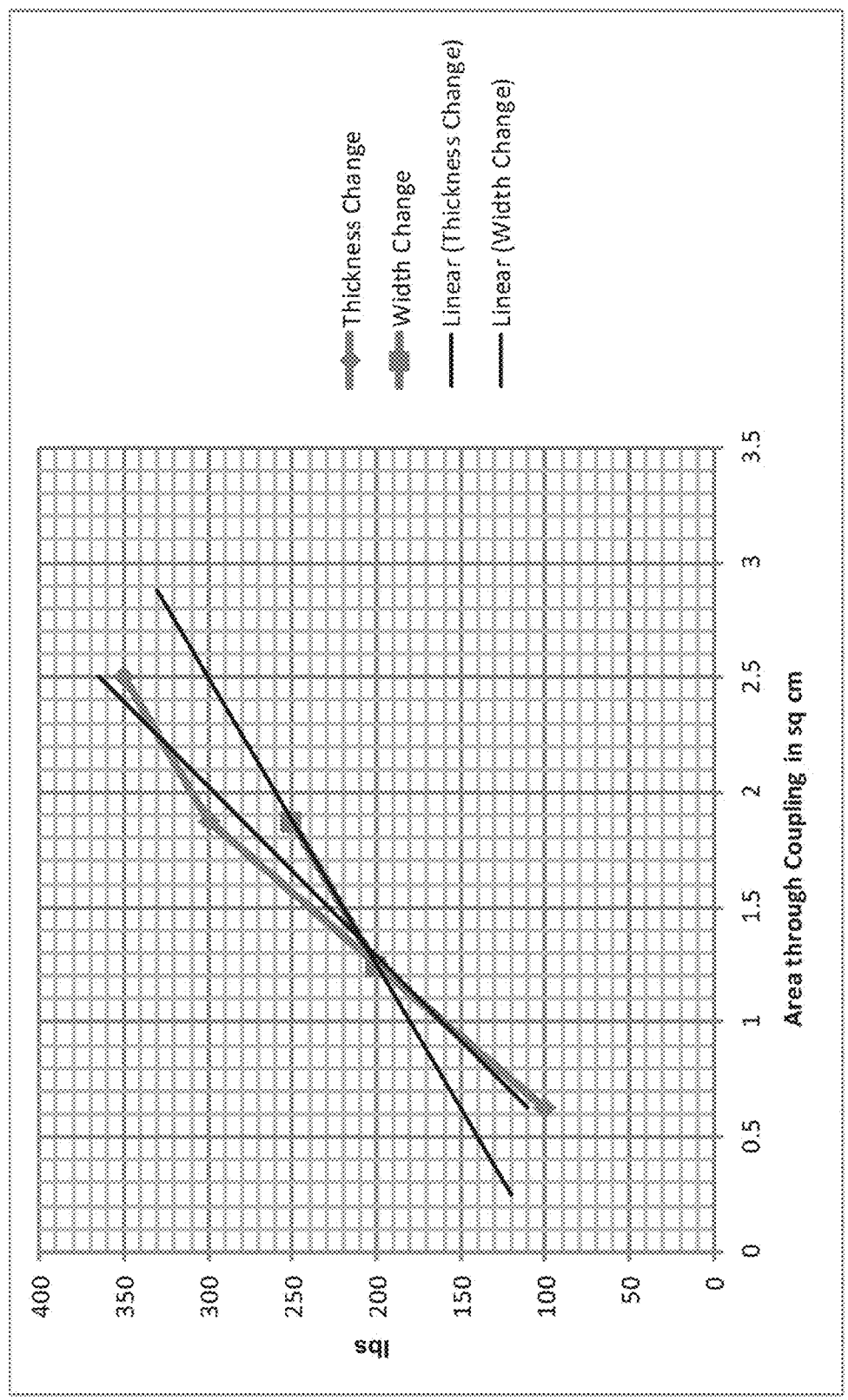
FIG. 21 illustrates a graph of failure or pull strength in lbs vs. cross sectional area in cm$^2$.

As described herein, the detachable guides are able to withstand relatively high tension loads before experiencing failure. One reason for this is the configuration of the stepped protrusion and stepped recess, which experience tension in shear rather than in bending. The configuration of the detachable guides provides tension member coupling components that have a small and low profile, yet achieve high failure strengths. For example, referring now to FIG. 21, illustrated is a graph that shows the failure or pull strengths of the detachable guides in lbs vs. a cross sectional area of the guides in square cm. The cross sectional area of the guides is calculated by determining the area of the coupled components relative to a plane that intersects the coupled components transversely at or near the stepped protrusion and stepped recess as shown in FIG. 4G.

As shown in FIG. 21 and after converting the strength to Newtons, the coupled components exhibit a failure strength of between about 560 N/cm$^2$ and 840 N/cm$^2$. In some embodiments, the coupled components exhibit a failure strength of between about 600 N/cm$^2$ and 800 N/cm$^2$, or a failure strength of between about 650 N/cm$^2$ and 750 N/cm$^2$. Table 1 below provides the raw data values of the graph of FIG. 21 and the conversion of the strength from lbs to Newtons. In obtaining the values below, a finite element analysis (FEA) program was performed on a detachable guide model having the height and width parameters defined in Table 1. As shown in Tale 1, the height or width of the detachable guide was varied and the FEA calculation performed to determine the effect of the design change on the failure strength of the component. As shown in Table 1, for each percentage change in thickness (i.e., height), the strength of the detachable guide changed by roughly an equivalent percentage. The calculated failure strength for the change in thickness was roughly about 712 N/cm$^2$. For each change in width, the calculated strength of the component changed at roughly ½ the rate of change in width. For example, an increase of 50% in width (i.e., 37.5 mm) resulted in a failure strength of roughly 593 N/cm$^2$, while a decrease of 50% in width (i.e., 12.5 mm) resulted in a failure strength of roughly 1067 N/cm$^2$.

To verify the results of the FEA calculations, a physical model of a detachable guide having a height of 5 mm and a width of 25 mm was constructed and the detachable guide was placed under 200 lb tension to measure the actual failure strength. The observed failure strength of the physical model closely corresponded to the calculated FEA value of roughly 712 N/cm$^2$. According to one embodiment, the failure or pull strength of the physical model was about 700 N/cm$^2$±20%. The ratio of failure strength to cross sectional area achieved by the detachable guides described herein are far greater than similar ratios achieved by conventional buckles or coupling components. As compared with other conventional side release buckles, the strength efficiency of the detachable guides, particularly for thickness, is more efficient because less bending stress is involved. As such, the detachable guides described herein exhibit a unique combination of reduced size and increased strength.

TABLE 1

Data Values of FIG. 21

| height mm | width mm | area in mm$^2$ | area in cm$^2$ | load in lbs | load in N | N/cm$^2$ |
|---|---|---|---|---|---|---|
| 5 | 25 | 125 | 1.25 | 200 | 889.6 | 711.7 |
| 2.5 | 25 | 62.5 | 0.625 | 100 | 444.8 | 711.7 |
| 7.5 | 25 | 187.5 | 1.875 | 300 | 1334.4 | 711.7 |
| 10 | 25 | 250 | 2.5 | 350 | 1556.8 | 622.7 |
| 5 | 37.5 | 187.5 | 1.875 | 250 | 1112 | 593.1 |
| 5 | 12.5 | 62.5 | 0.625 | 150 | 667 | 1067.2 |

As described herein, the detachable guides may be made of various materials. In one embodiment, the material may be a Nylon, Acetal, Polycarbonate (PC), and/or other material. In some embodiments, the material may be selected to provide a yield strength within the range of 50 to 90 MPa and/or a flexural modulus of 2,000 to 3,500 MPa. In other embodiments, the yield strength may be between about 60 and 85 MPa and the flexural modulus may be between about 2,600 and 3,000 MPa. Table 2 below provides various properties of materials that may be used for the detachable guides described herein. Specifically, the properties include the modulus and tensile strength of 3 materials: Polycarbonate (PC), Polyoxymethylene (POM)—an Acetal, and a Nylon material—i.e., Ultramid® A3K Uncolored Polyamide sold by BASF.

TABLE 2

Properties of Various Detachable Guide Materials

|  | A3K | POM | PC |
|---|---|---|---|
| Modulus (MPA) | 3000/1100 | 2900 | 2400 |
| Tensile Strength, Yield (MPA) | 85 (dry) | 64 | 66 |

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A coupling device for coupling opposing portions of an article, the coupling device comprising:
    a female component having:
        a main body portion; and
        a coupling aperture; and
    a male component having:
        a main body portion having an upper surface, a lower surface, a proximal end, and a distal end;
        a coupling member positioned on the distal end of the main body, the coupling member being
            insertable within the coupling aperture to couple the male and female components together;
        a tension member that is tensionable to tension the male and female components; and
        a reel assembly that is positioned atop and coupled with the upper surface of the male component and that is operationally coupled with the tension member to adjust a tension of the tension member upon operation of the reel assembly.

2. The coupling device of claim 1, further comprising a strap that is operationally coupled with the tension member such that tensioning of the tension member effects tensioning of the strap.

3. The coupling device of claim 1, wherein the article is a brace, and wherein the female component is coupled with one side of the brace and the male component is coupled with an opposing side of the brace so as to allow the brace to be opened and closed about a limb of a patient by coupling and uncoupling the male and female components.

4. The coupling device of claim 3, wherein the female component is coupled with the brace via:
    stitching a flange of the main body to the brace;
    inserting a rivet through an aperture of the main body and into the brace; or
    injection molding the female component into the brace.

5. The coupling device of claim 3, wherein when coupled together, the male and female components have a low profile about a surface of the brace so as to minimize contact between the male and female components and surrounding objects.

6. The coupling device of claim 3, wherein the male and female components are lockable in the coupled engagement to prevent uncoupling of the male and female components after tension is removed.

7. The coupling device of claim 1, wherein:
    the female component has an arcuate configuration that corresponds to a shape of the article;
    the male component has a generally planar configuration; and
    wherein tensioning the male and female components via the tension member causes the male component to rotate into an increased engagement with the female component.

8. The coupling device of claim 1, wherein the coupling device includes an audible feedback mechanism that provides audible feedback to the user that indicates coupling or uncoupling of the male and female components.

9. The coupling device of claim 8, wherein the audible feedback mechanism includes:
    a post that is coupled with the main body of the female component, and
    a flange member that is coupled with the main body of the male component, wherein the flange member snaps into engagement with the post to produce the audible feedback as the male and female components are coupled together.

10. The coupling device of claim 1, wherein the proximal end of the main body of the male component includes an arcuate recess that aids in gripping the male component during coupling or uncoupling of the male and female components.

11. A coupling device comprising:
    a female component including:
        a main body portion having a top surface and a bottom surface; and
        a coupling aperture that is accessible from the top surface of the main body; and
    a male component including:
        a main body portion having a top surface and a bottom surface; and
        a coupling member having a tab that extends downward from the bottom surface of the coupling member and a flange that extends distally from the tab;
    wherein the coupling aperture and the coupling member are configured such that coupling of the male component and the female component is achieved by insertion of the coupling member's flange within the coupling aperture while the male component is oriented at an angle relative to the female component and is further achieved by rotating the male component downward after the flange is inserted into the coupling aperture such that after rotation of the male component, the male component and the female component are roughly aligned;

wherein the coupled male and female components have a cross sectional area and wherein the coupled components exhibit a failure strength of between about 560 and 840 Newtons per square centimeter of cross sectional area.

12. The coupling device of claim 11, wherein the male and female components are tensionable via a tension member and are non-releasable by a user from a coupled engagement while under tension, and wherein the tension member is a lace and the proximal end of the male component's main body includes a channel throughwhich the lace is inserted, or the proximal end of the male component's main body includes a reel assembly that couples with the lace.

13. The coupling device of claim 11, wherein the coupling device is attached to a brace to allow the brace to be opened and closed about a limb of a patient by coupling and uncoupling the male and female components, and wherein the female component is coupled with a side of an opening of the brace and the male component is coupled with an opposing side of the opening of the brace.

14. The coupling device of claim 11, wherein the main body of the female component includes a post and the main body of the male component includes a flange member, the flange member being configured to snap into engagement with the post as the male and female components are coupled together to produce audible feedback.

15. A coupling device comprising:
a female component having:
  a main body portion having an upper surface, a lower surface, and opposing side surfaces; and
  a single coupling aperture positioned roughly equidistant from each side surface of the opposing side surfaces, the single coupling aperture being accessible from the upper surface of the main body portion; and
a male component having:
  a main body portion that includes a top surface and a bottom surface; and
  a single coupling member that extends from a distal end of the main body and that is mateable with the single coupling aperture of the female component to couple the male and female components together;
wherein the male and female components are non-releasable from a coupled engagement until after tension is released from a tension member, and wherein the coupled male and female components have a cross sectional area and exhibit a failure strength of between about 560 and 840 Newtons per square centimeter of cross sectional area.

16. The coupling device of claim 15, further comprising a reel assembly that is positioned atop the top surface of the male component.

* * * * *